US012629495B2

(12) United States Patent
Kapur et al.

(10) Patent No.: US 12,629,495 B2
(45) Date of Patent: May 19, 2026

(54) SHEATH AND CANNULA COMBINATION DEVICES FOR SELECTIVELY DIRECTING BLOOD FLOW AND ENABLING INTERVENTIONAL MEDICAL PROCEDURES

(71) Applicant: Tufts Medical Center, Inc., Boston, MA (US)

(72) Inventors: Navin K. Kapur, Hanover, MA (US); Richard H. Karas, Franklin, MA (US); William Gesler, Kalamazoo, MI (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

(21) Appl. No.: 19/183,407

(22) Filed: Apr. 18, 2025

(65) Prior Publication Data

US 2025/0325738 A1     Oct. 23, 2025

Related U.S. Application Data

(60) Provisional application No. 63/719,622, filed on Nov. 12, 2024, provisional application No. 63/690,058, (Continued)

(51) Int. Cl.
| | |
|---|---|
| *A61M 25/00* | (2006.01) |
| *A61M 39/06* | (2006.01) |

(Continued)

(52) U.S. Cl.
CPC ........ *A61M 25/0097* (2013.01); *A61M 39/06* (2013.01); *A61M 39/10* (2013.01);
(Continued)

(58) Field of Classification Search
CPC .... A61M 1/1698; A61M 1/32; A61M 1/3659; A61M 1/3666; A61M 2039/062;
(Continued)

(56) References Cited

U.S. PATENT DOCUMENTS

| | | |
|---|---|---|
| 4,287,892 A | 9/1981 | Schiff |
| 5,125,903 A | 6/1992 | McLaughlin et al. |
| | (Continued) | |

FOREIGN PATENT DOCUMENTS

| | | |
|---|---|---|
| CN | 210963550 U | 7/2020 |
| CN | 112755285 A | 5/2021 |
| | (Continued) | |

OTHER PUBLICATIONS

Pasrija, et al., A novel adaptor system enables endovascular access through extracorporeal life support circuits, The Journal of Thoracic and Cardiovascular Surgery, 158(5):1359-1366 (Nov. 2019).
(Continued)

*Primary Examiner* — Shefali D Patel
(74) *Attorney, Agent, or Firm* — Greenberg Traurig, LLP; Christopher C. Bolten; Albert K. Heng

(57) ABSTRACT

Systems are provided including a sheath and cannula combination device for permitting a user to select between directing blood flow through a first cannula portion of the combination device in a cannula mode and enabling an interventional medical procedure through a second sheath portion of the combination device in a sheath mode, or performing both the cannula mode and the sheath mode simultaneously. The combination device may include a connector hub configured to auto-washout stasis regions of blood within the first cannula portion. The systems may include a series of removable caps for temporarily sealing the first cannula portion and/or the second sheath portion of the combination device, such that the user may seamlessly select when to use the combination device in the cannula mode, the sheath mode, both the cannula mode and the sheath mode simultaneously, or neither the cannula mode nor the sheath mode.

30 Claims, 31 Drawing Sheets

Related U.S. Application Data filed on Sep. 3, 2024, provisional application No. 63/636,682, filed on Apr. 19, 2024.

(51) Int. Cl.

| | |
|---|---|
| *A61M 39/10* | (2006.01) |
| *A61M 39/20* | (2006.01) |
| A61M 39/22 | (2006.01) |

(52) U.S. Cl.
CPC ....... *A61M 39/20* (2013.01); *A61M 2039/062* (2013.01); *A61M 2039/0626* (2013.01); *A61M 2039/0646* (2013.01); *A61M 2039/229* (2013.01)

(58) Field of Classification Search
CPC .... A61M 2039/0626; A61M 2039/229; A61M 2202/0413; A61M 2210/12; A61M 25/0097; A61M 39/06; A61M 39/28; A61M 2025/0018; A61M 39/08; A61M 39/10; A61M 39/105; A61M 39/20; A61M 39/22; A61M 2039/1072
See application file for complete search history.

(56) References Cited

U.S. PATENT DOCUMENTS

| | | | |
|---|---|---|---|
| 5,195,980 A | | 3/1993 | Catlin |
| 5,254,097 A | * | 10/1993 | Schock ................. A61M 39/04 604/167.04 |
| 5,269,764 A | | 12/1993 | Vetter et al. |
| 5,395,349 A | * | 3/1995 | Quiachon .......... A61B 17/3462 604/167.03 |
| 5,911,710 A | | 6/1999 | Barry et al. |
| 6,083,198 A | | 7/2000 | Afzal |
| 6,183,443 B1 | | 2/2001 | Kratoska et al. |
| 6,210,365 B1 | | 4/2001 | Afzal |
| 6,241,666 B1 | | 6/2001 | Pomeranz et al. |
| 6,508,777 B1 | * | 1/2003 | Macoviak .......... A61M 25/1011 604/9 |
| 6,632,236 B2 | | 10/2003 | Hogendijk |
| 6,673,042 B1 | | 1/2004 | Samson et al. |
| 7,938,809 B2 | | 5/2011 | Lampropoulos et al. |
| 8,162,894 B2 | * | 4/2012 | Valaie ............... A61M 39/0613 604/167.03 |
| 8,523,757 B2 | * | 9/2013 | Taub ..................... A61M 1/367 604/4.01 |
| 8,996,095 B2 | | 3/2015 | Anderson et al. |
| 9,144,662 B2 | | 9/2015 | Di Caprio et al. |
| 10,322,275 B2 | * | 6/2019 | Kaczorowski ...... A61M 1/3655 |
| 10,328,240 B2 | | 6/2019 | Nardeo et al. |
| 10,485,956 B2 | | 11/2019 | O'Donovan |
| 11,331,421 B2 | * | 5/2022 | Kapur ................. A61M 1/3659 |
| 11,547,786 B2 | | 1/2023 | Kapur |
| 11,738,131 B2 | | 8/2023 | Kapur |
| 11,964,091 B1 | | 4/2024 | Fischell et al. |
| 12,186,469 B2 | | 1/2025 | Kapur |
| 2003/0088213 A1 | | 5/2003 | Schweikert et al. |
| 2004/0267084 A1 | | 12/2004 | Navia et al. |
| 2006/0047266 A1 | | 3/2006 | Elkins et al. |
| 2006/0079859 A1 | | 4/2006 | Elkins et al. |
| 2011/0190683 A1 | | 8/2011 | Gellman et al. |
| 2013/0274783 A1 | | 10/2013 | Wynberg |
| 2014/0012281 A1 | | 1/2014 | Wang et al. |
| 2014/0221964 A1 | | 8/2014 | Xiao et al. |
| 2016/0158489 A1 | | 6/2016 | Wu et al. |
| 2017/0080178 A1 | | 3/2017 | O'Connell et al. |
| 2017/0120034 A1 | | 5/2017 | Kaczorowski |
| 2017/0200347 A1 | | 7/2017 | Acres |
| 2017/0238951 A1 | | 8/2017 | Yang et al. |
| 2017/0252548 A1 | | 9/2017 | Krimsky |
| 2018/0099126 A1 | | 4/2018 | Rousu |
| 2018/0193026 A1 | | 7/2018 | Yang et al. |
| 2018/0207399 A1 | | 7/2018 | Chou et al. |
| 2018/0243004 A1 | | 8/2018 | Von Segesser |
| 2019/0160259 A1 | | 5/2019 | Cottone et al. |
| 2019/0247564 A1 | | 8/2019 | Lu et al. |
| 2019/0358434 A1 | | 11/2019 | Fuller et al. |
| 2020/0146852 A1 | | 5/2020 | Raychev et al. |
| 2020/0289794 A1 | | 9/2020 | Fantuzzi |
| 2021/0085923 A1 | | 3/2021 | Fantuzzi et al. |
| 2021/0178142 A1 | | 6/2021 | Sauer et al. |
| 2021/0308359 A1 | | 10/2021 | Kapur |
| 2021/0322729 A1 | | 10/2021 | Howell |
| 2022/0280709 A1 | | 9/2022 | Kapur |
| 2022/0313888 A1 | | 10/2022 | Kon et al. |
| 2023/0226335 A1 | | 7/2023 | Finck et al. |
| 2023/0233802 A1 | | 7/2023 | Finck et al. |
| 2023/0248939 A1 | | 8/2023 | Griffith et al. |
| 2025/0065028 A1 | | 2/2025 | Kapur |

FOREIGN PATENT DOCUMENTS

| | | | |
|---|---|---|---|
| CN | 214969916 U | | 12/2021 |
| CN | 115887807 A | | 4/2023 |
| EP | 2978372 A2 | | 2/2016 |
| JP | 2018510735 A | | 4/2018 |
| JP | 2019521820 A | | 8/2019 |
| WO | WO-2014160832 A2 | | 10/2014 |
| WO | WO-2017075521 A1 | | 5/2017 |
| WO | WO-2023220724 A1 | | 11/2023 |
| WO | WO-2025222139 A1 | | 10/2025 |

OTHER PUBLICATIONS

International Search Report & Written Opinion dated Sep. 13, 2021 in Int'l PCT Patent Appl. Serial No. PCT/US2021/025461.

International Search Report & Written Opinion dated Oct. 23, 2023 in Int'l PCT Patent Appl. No. PCT/US2023/066945.

Ng et al., "Clinical use of the venoarterial extracorporeal membrane oxygenation," Hong Kong Med. J., vol. 23:282-290 (May 2017).

Pavlushkov, et al, Cannulation Techniques for Extracorporeal life Support, Review Article on Extracorporeal Life Support, Annals of Translational Medicine, 5(4):70 (Feb. 2017).

Sulimov, M.D., et al., Rescue Peripheral Intervention Using a Peripheral ECMO-Cannula as Vascular Access, J. Amm. Golf. Cardial. Intv., Jan. 29, 2020 epublished 001:10.1016/j.jcin.2019.11.038.

Swain, et al., Transvalvular Ventricular Unloading Before Reperfusion in Acute Myocardial Infarction, Journal of the American College of Cardiology, 76(6):685-699 (Aug. 2020).

Wickramarachchi, et al., The Effect of Arterial Cannula Tip Position on Differential Hypoxemia During Venoarterial Extracorporeal Membrane Oxygenation, Physical and Engineering Sciences in Medicine, https://doi.org/10.1007/s13246-022-01203-6 , published online: Dec. 2, 2022.

International Search Report & Written Opinion dated Sep. 4, 2025 in Int'l PCT Patent Appl. Serial No. PCT/US2025/025400.

* cited by examiner

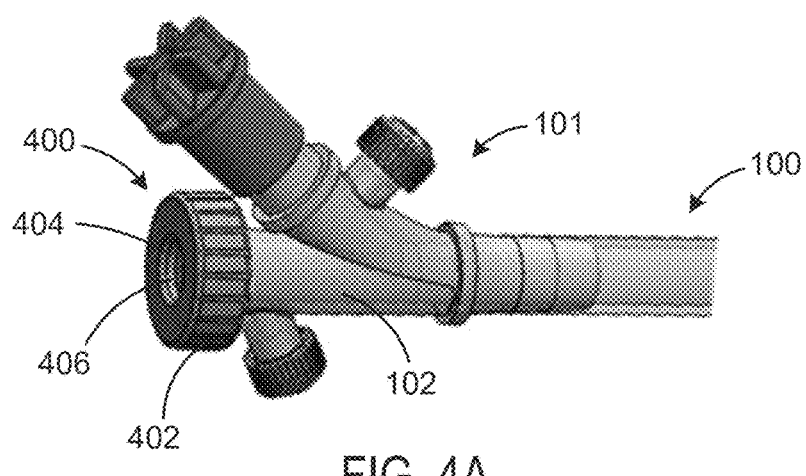
FIG. 4A
FIG. 4B
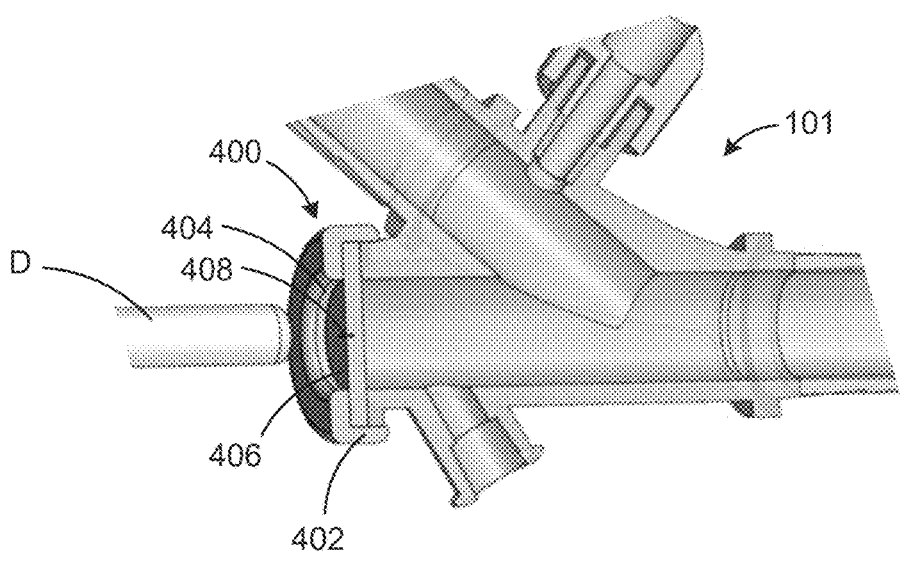
FIG. 4C

SHEATH AND CANNULA COMBINATION DEVICES FOR SELECTIVELY DIRECTING BLOOD FLOW AND ENABLING INTERVENTIONAL MEDICAL PROCEDURES

CROSS-REFERENCE TO RELATED APPLICATIONS

This application claims priority to U.S. Provisional Patent Application No. 63/719,622, filed Nov. 12, 2024, U.S. Provisional Patent Application No. 63/690,058, filed Sep. 3, 2024, and U.S. Provisional Patent Application No. 63/636,682, filed Apr. 19, 2024, the entire contents of each of which are incorporated herein by reference.

TECHNICAL FIELD

This technology relates to hybrid sheath/cannula systems for directing blood flow in a cardiopulmonary bypass system (e.g., during extracorporeal membrane oxygenation (ECMO) blood perfusion) in a cannula mode and enabling another medical procedure in a sheath mode, and methods of use thereof.

BACKGROUND

Nearly 700,000 individuals suffer cardiac arrest each year in the United States alone. Despite advances in cardiopulmonary resuscitation (CPR), up to 90% of patients with cardiac arrest will die. Recently, use of venous-arterial extracorporeal membrane oxygenation (ECMO) to assist CPR, known as E-CPR, has been shown to improve survival by 5-fold in patients with cardiac arrest. Contemporary data illustrates that nearly 50% of E-CPR cases occur in the peri-procedural setting where a patient is undergoing a complex medical procedure and develops cardiac arrest. Based on these findings, clinical care guidelines now support the use of ECMO in cardiac arrest and as a result, ECMO implementation has grown by nearly 11-fold in the United States and Europe over the past decade. However, implementing ECMO remains a technical challenge since most components of this technology were designed for use in the operating room as part of cardiopulmonary bypass (CPB) systems. Specifically, the cannulas used to direct blood flow into the body during ECMO were also designed to be implanted by surgeons requiring a surgical procedure, whereas the current and future application of ECMO is focused on insertion of the required cannulas by non-surgical personnel outside of the operating room. For these reasons, new approaches to enable safe, rapid, and effective deployment of ECMO outside of the operating room are needed.

Arterial perfusion to every major organ system, including the heart, kidneys and brain, is determined by arterial pressure, blood flow, vascular tone, and intra-organ vascular resistance. When a patient experiences low arterial perfusion due to heart failure, cardiopulmonary failure, and cardiogenic or septic shock, venous-arterial extracorporeal membrane oxygenation (VA-ECMO) systems may be used to provide both circulatory and gas exchange support by augmenting the flow of oxygenated blood. See, e.g., Pavlushkov E, Berman M, Valchanov K. Cannulation techniques for extracorporeal life support. Ann Transl Med 2017; 5(4):70. doi: 10.21037/atm.2016.11.47. Specifically, VA-ECMO drains blood from the venous system, oxygenates this blood outside of the patient, and then delivers oxygenated blood back to the arterial system, e.g., via the femoral artery. VA-ECMO is most commonly performed via large-bore cannulas placed in the femoral vein and femoral artery (known as peripheral VA-ECMO). VA-ECMO is an established strategy for cardiopulmonary support. ECMO may also be performed with alternative configurations from VA-ECMO such as VV-ECMO, VVA-ECMO, or VAV-ECMO. Large-bore ECMO cannulae for use in adult humans generally range in diameter from 15 Fr (5.0 mm) to 25 Fr (8.3 mm) and are used to deliver life-sustaining blood flow rates of between 3 and 8 liter/min.

Venous-venous extracorporeal membrane oxygenation (VV-ECMO), which drains blood from the venous system, oxygenates this blood outside of the patient, and then delivers oxygenated blood back to the venous system, is sometimes the treatment of choice for patients with respiratory failure refractory to optimal mechanical ventilation and conventional medical treatments. To mitigate the effects of heart or lung injury, concomitant devices such as intra-aortic balloon pumps and Impella® pumps (made available by Abiomed, Inc. of Danvers, Massachusetts) may be used concomitantly with VA-ECMO and/or VV-ECMO, and require additional vascular puncture. All of these complications are associated with increased mortality, long-term morbidity, length of stay in the hospital, and healthcare costs. New approaches to limit complications associated with VA-ECMO and VV-ECMO are required.

In contemporary practice, VA-ECMO is also used to support commonly performed life-saving procedures such as coronary angioplasty, aortic valvuloplasty, or aortic valve replacement. However, several critical barriers limit the ability to use VA-ECMO during complex interventional procedures. First, a major limitation is the need for additional vascular access to place vascular sheaths and/or catheters for required interventional equipment in addition to the existing VA-ECMO circuit. Conversely for patients undergoing a complex procedure who then become unstable, the emergent placement of cannulas to enable VA-ECMO can be prohibitive. For these reasons, a sheath that enables coupling to ECMO without the need for additional vascular access is a major advance. This can be prohibitive for patients who have peripheral vascular disease, concomitant vascular injury, or vessels occupied by other life-saving equipment. Second, to initiate VA-ECMO during an interventional procedure, a continuous wet-to-wet connection has to be made between the sheath and the VA-ECMO circuit to limit risk of air embolization. Current sheaths do not allow for wet-to-wet connections to the ⅜" tubing used with VA-ECMO. Third, to enable this wet-to-wet connection, a clamp is commonly placed across a cannula. If the cannula contains interventional equipment such as catheters, stents, or valves, these may be crushed during clamping. New approaches are needed to enable clamping and wet-to-wet coupling between a delivery sheath and ECMO circuit. Finally, under emergent conditions, placing additional vascular access can be challenging and increase risk of injury. For these reasons, any approach that overcomes these critical barriers will enable safer procedures and better outcomes for patients.

U.S. Pat. Nos. 5,125,903, 5,195,980, 5,269,764, and 7,938,809 describe percutaneous catheter introducers/connectors having hemostatic valves for permitting passage of elongated interventional devices into a patient's vasculature, and a side port for connection with, e.g., an outside source of perfusion, aspiration, contrast media, medicaments, etc. These systems are not designed for use with VA-ECMO. Moreover, no existing approach allows for simple and effective access to the VA-ECMO circuit for delivery of additional interventional equipment which can range in size from 5 Fr to 20 Fr in diameter. Current Y-connectors used to provide access to an ECMO circuit suffer from numerous disadvantages including reduction in the effective lumen of the ECMO return cannula creating an undesirable pressure gradient, difficult angulation requirements that prohibit introduction of additional catheters without risk of kinking or catheter disruption. Such previously known connectors require the introducer sheath to be inserted nearly 25 to 30 cm more distal than usual due to interposition connecting tubing, thereby limiting access to the thoracic aorta, aortic root, aortic valve or coronary vasculature for therapeutic interventions. Such connectors also pose a risk of bleeding during ECMO disconnection and reconnection, with increased risk of air embolism and contamination due to disconnection from the ECMO circuit. See, e.g., Dmitriy S. Sulimov, M D et al., "Rescue Peripheral Intervention Using a Peripheral ECMO-Cannula as Vascular Access," J Am Coll Cardiol Intv. 2020 Jan. 29. Epublished DOI: 10.1016/j.jcin.2019.11.038.

In view of the foregoing drawbacks of previously known systems and methods, there exists a need for a system that provides simple and effective access to a blood pump (e.g., an ECMO circuit) during delivery of interventional medical equipment, while reducing the number of vasculature punctures and injury to the patient. Improved systems are described in WO 2023/220724 A1 and U.S. Pat. Nos. 11,331,421, 11,547,786, and 11,738,131 to Kapur, the entire contents of each of which are incorporated herein by reference.

SUMMARY

This technology overcomes the drawbacks of previously-known systems and methods by providing a sheath and cannula combination device for selectively directing blood flow and enabling interventional medical procedures. For example, the sheath and cannula combination device may comprise an elongated shaft defining a longitudinal axis and comprising a distal region having a first outlet, a proximal region having a first inlet, and a first lumen extending between the first outlet and the first inlet along the longitudinal axis. The distal region may be configured to be in fluid communication with a patient's vasculature, and the first lumen may be sized and shaped to permit insertion of an interventional medical device therethrough in a sheath mode for performing the interventional medical procedure. For example, the distal region may be configured to be inserted into the patient's vasculature. The combination device further may include a connector hub at the proximal region of the elongated shaft, the connector hub comprising a collinear port configured to receive the interventional medical device therethrough, and a sidearm configured to be fluidically coupled to the first lumen at the proximal region of the elongated shaft, the sidearm angled relative to the longitudinal axis of the elongated shaft. The sidearm may define a second outlet, a second inlet, and a second lumen extending between the second inlet and the second outlet, the second lumen sized and shaped to direct blood flow from the sidearm into the first lumen of the elongated shaft and out the first outlet in a cannula mode. The elongated shaft may comprise a connection portion at the first outlet configured to be removably coupled to an inlet of a return cannula, e.g., an arterial cannula, configured to be positioned within the patient's vasculature to fluidically couple the first and second inlets and the patient's vasculature. In some embodiments, the connector hub may be configured to be removably coupled to the proximal region of the elongated shaft.

In addition, the combination device may comprise a first port fluidically coupled to the elongated shaft at the proximal region, the first port angled towards the collinear port to permit fluid flow therethrough to washout stasis regions of blood within the collinear port. Moreover, the combination device further may comprise a second port fluidically coupled to the second lumen of the sidearm. For example, the combination device further may comprise a tubing having a first end configured to be coupled to the second port, and a second end configured to be coupled to the first port, the tubing configured to redirect at least some blood flow from the second lumen through the tubing into the first lumen towards the collinear port to washout stasis regions of blood within the collinear port in the cannula mode. The first end of the tubing may be configured to be removably coupled to the second port, and the second end of the tubing may be configured to be removably coupled to the first port. In some embodiments, the second port may be configured to be coupled to a perfusion cannula configured to redirect at least some blood flow from the second lumen through the perfusion cannula for perfusion of the patient's distal extremities in the cannula mode. Additionally, the combination device may comprise a male-to-male connector having a first end configured to be fluidically coupled to the first port, and a second end configured to be fluidically coupled to a male end of a stopcock.

The first lumen may have a diameter between 12 Fr and 32 Fr. In addition, the second inlet of the sidearm may be configured to be fluidically coupled to a cardiopulmonary bypass system, e.g., an ECMO circuit. Moreover, the combination device further may include a hemostatic valve configured to be removably coupled to the first inlet, the hemostatic valve comprising a locking mechanism and configured to sealably receive the interventional medical device therethrough in the sheath mode. For example, the hemostatic valve may comprise one or more disc-shaped valve membranes. Alternatively, the hemostatic valve may comprise a duckbill valve membrane configured to seal the first inlet. For example, a distal end of the duckbill valve membrane may comprise a beveled geometry corresponding to a geometry of the second lumen such that the duckbill valve membrane does not obstruct fluid flow between the second lumen and the first lumen in the cannula mode. Additionally, the combination device may include a hemostatic valve cap configured to be removably coupled to the hemostatic valve to seal the hemostatic valve. The valve cap may contain a backup valve to provide additional hemostasis or support for catheter delivery through the collinear port. The hemostatic valve cap may be coupled to the collinear port via a lanyard.

Further, the combination device may include a collinear port cap configured to be removably coupled to the proximal end of the collinear port to seal the first inlet. The collinear port cap may comprise an obturator sized and shaped to be disposed within at least a portion of the first lumen to prevent pooling of blood within the at least the portion of the first lumen, and a distal end of the obturator may comprise a beveled geometry corresponding to a geometry of the second lumen of the sidearm such that the obturator does not obstruct blood flow between the second lumen and the first lumen in the cannula mode. Moreover, the collinear port cap may be configured to be removably coupled to the proximal end of the collinear port in a manner that auto-aligns the beveled geometry of the obturator with the second lumen of the sidearm. In addition, the combination device may include a sidearm cap configured to be removably coupled to the proximal end of the sidearm to seal the second inlet. The sidearm cap may comprise an obturator sized and shaped to be disposed within the second lumen to prevent pooling of blood within the second lumen, and a distal end of the obturator may comprise a beveled geometry corresponding to a geometry of the first lumen of the elongated shaft such that the obturator does not obstruct the first lumen in the sheath mode. Moreover, the sidearm cap may be configured to be removably coupled to the proximal end of the sidearm in a manner that auto-aligns the beveled geometry of the obturator with the first lumen of the elongated shaft.

The combination device further may include a sidearm extender having a proximal end comprising a third inlet configured to be fluidically coupled to a cardiopulmonary bypass system, e.g., an ECMO circuit, a distal end comprising a third outlet configured to be fluidically coupled to the second inlet of the sidearm, and a third lumen extending between the third inlet and the third outlet, the third lumen sized and shaped to direct blood flow from the sidearm extender through the sidearm and into the first lumen of the elongated shaft and out the first outlet in the cannula mode. The sidearm extender may comprise a one-way valve disposed within the third lumen. In some embodiments, the combination device may include an actuator operatively coupled to the one-way valve, the actuator configured to be actuated to transition the one-way valve between an open state where blood flow is permitted to flow through the third lumen in the cannula mode, and a closed state where blood flow through the third lumen is prevented. Moreover, the sidearm extender may comprise a clampable region disposed between the third inlet and the third outlet, the clampable region configured to be clamped to prevent blood flow through the third lumen. In some embodiments, the distal end of the sidearm extender may be configured to be removably coupled to the proximal end of the sidecarm. Further, the combination device may include a sidearm extender cap configured to be removably coupled to the proximal end of the sidearm extender to seal the third inlet. The sidearm extender cap may comprise an obturator sized and shaped to be disposed within the third and second lumens to prevent pooling of blood within the third and second lumens, and a distal end of the obturator comprising a beveled geometry corresponding to a geometry of the first lumen such that the obturator does not obstruct the first lumen in the cannula mode.

In addition, the combination device may include a collinear port delivery cap configured to be removably coupled to the proximal end of the collinear port to seal the first inlet. The collinear port delivery cap may comprise an obturator sized and shaped to be disposed within the first lumen such that a distal end of the obturator extends beyond the first outlet of the elongated shaft, the distal end of the obturator comprising an atraumatic tip. Moreover, the combination device may include a sidearm delivery cap configured to be removably coupled to the proximal end of the sidearm to seal the second inlet. The sidearm delivery cap may comprise a flexible obturator sized and shaped to be disposed within the second lumen and at least a portion of the first lumen such that a distal end of the flexible obturator extends beyond the first outlet of the elongated shaft, the distal end of the flexible obturator comprising an atraumatic tip. Moreover, the combination device may include a fixation pad configured to couple the sheath and cannula combination device to the patient's skin. The fixation pad may comprise one or more hooks configured to receive at least a portion of the sheath and cannula combination device therein. For example, the fixation pad may comprise an adhesive surface configured to adhere the fixation pad to the patient's skin. Additionally, or alternatively, the fixation pad may comprise one or more suture holes configured to receive one or more sutures for coupling the fixation pad to the patient's skin.

In some embodiments, the distal region of the elongated shaft may be configured to be inserted into an artery supplying blood to a distal limb of the patient. For example, the distal region of the elongated shaft may comprise a size between 4 Fr and 10 Fr, and the sidearm may comprise a Luer connector having a size between 8 Fr and 14 Fr. Moreover, the distal region of the elongated shaft may be sized and shaped to be inserted into an axillary artery, and the first lumen may be sized and shaped to permit insertion of a heart pump device, e.g., catheter-based heart pump device, therethrough.

In accordance with one aspect, a system for selectively directing blood flow and enabling an interventional medical procedure is provided. The system may include the sheath and cannula combination device described above, as well as an expandable extension cannula. The expandable extension cannula may comprise a proximal region comprising a return cannula configured to receive blood flow from an external pump, a distal region comprising a flexible conduit configured to transition between a collapsed insertion state and an expanded deployed state when in communication with a blood flow from the external pump, and a hypotube coupled to a distal end of the flexible conduit and configured to advance the flexible conduit through the collinear port of the connector hub into the first lumen of the elongated shaft and out of the first outlet of the elongated shaft. The flexible conduit may have a length selected so that when the first outlet of the elongated shaft is positioned in the aorta at a location proximal of the patient's renal vessels, one or more outflow vents of the flexible conduit extend beyond the patient's renal vessels.

The flexible conduit may comprise a biocompatible fabric. Further, a distal portion of the flexible conduit may comprise a tapered portion having a cross-sectional area that decreases towards the distal end of the flexible conduit, and the one or more outflow vents may be disposed on at least the tapered portion of the flexible conduit. Additionally, the one or more outflow vents may be arranged circumferentially around the tapered portion of the flexible conduit, and extending longitudinally along the tapered portion. In addition, a width of the one or more outflow vents may increase in a proximal direction. The one or more outflow vents of the flexible conduit further may comprise one or more pores disposed at a distal region of the flexible conduit. The distal end of the flexible conduit may comprise a tip coupled to a distal end of the hypotube. Accordingly, the hypotube may have a length selected so that the hypotube extends proximally from the tip through the internal lumen of the flexible conduit and beyond a proximal end of the flexible conduit.

Moreover, a proximal region of the return cannula may comprise a lumen collinear with a lumen of the hypotube, and the lumens of the proximal region of the return cannula and the hypotube may be sized and shaped to receive a guidewire therethrough. In addition, the tip may comprise one or more holes extending therethrough, the one or more holes sized and shaped to permit blood flow therethrough to mitigate formation of clots adjacent to the tip within the flexible conduit. The hypotube may be configured so that the blood flow from the external pump does not pass through the hypotube. Additionally, a proximal region of the flexible conduit may be configured to be fixedly coupled to the return cannula. The return cannula may comprise an inlet in fluid communication with the one or more outflow vents of the flexible conduit, the inlet extending laterally along an outer surface of the return cannula and configured to be aligned with the second outlet of the sidearm to fluidically couple the sidearm and the expandable extension cannula and form a continuation of the blood flow path through the second lumen of the sidearm.

The return cannula further may comprise a handle configured to selectively rotate the expandable extension cannula relative to the sheath and cannula combination device to vary a degree of alignment between the inlet of the return cannula and the second outlet of the sidearm to thereby vary an amount of blood flow through flexible conduit. For example, the return cannula may be configured such that, when the inlet of the return cannula and the second outlet of the sidearm are not completely aligned, at least a portion of blood flow through the sidearm is directed to a space within the first lumen of the elongated shaft between the outer surface of the return cannula and an inner surface of the elongated shaft, the space in fluid communication with the first outlet of the elongated shaft. Moreover, a distal portion of the return cannula may have an outer diameter that is smaller than a diameter of the first lumen of the elongated shaft. In addition, the distal portion of the return cannula may comprise one or more openings configured to fluidically couple a lumen of the return cannula with the space within the first lumen of the elongated shaft between an outer surface of the return cannula and an inner surface of the elongated shaft, the space in fluid communication with the first outlet of the elongated shaft. Further, a proximal portion of the return cannula may have an outer diameter that is substantially equal to a diameter of the first lumen of the elongated shaft.

In some embodiments, a proximal portion of the return cannula may comprise a clamping arm extending radially outward at an angle relative a longitudinal axis of the return cannula. The clamping arm may comprise a receiving channel sized and shaped to releasably engage the sidearm in a manner that aligns the inlet of the return cannula with the second outlet of the sidearm. The return cannula further may comprise an in-line connector having an inlet in fluid communication with the one or more outflow vents of the flexible conduit and configured to be removably coupled to an outlet of the external pump, and a side arm having a lumen in fluid communication with a lumen of the hypotube, the lumens of the side arm and the hypotube sized and shaped to receive a guidewire therethrough.

In accordance with another aspect, a system for selectively directing blood flow and enabling an interventional medical procedure is provided. The system may include the sheath and cannula combination device described above, further comprising a port fluidically coupled to the second lumen of the sidearm, as well as a distal perfusion sheath and cannula combination device. The distal perfusion sheath and cannula combination device may include a second elongated shaft comprising a distal region having a third outlet, a proximal region having a third inlet collinear with the third outlet, and a third lumen extending between the third inlet and the third outlet along a longitudinal axis of the second elongated shaft. The distal region may be configured to be inserted into an artery supplying blood to a distal limb of the patient, and the third lumen may comprise a diameter between 4 Fr and 10 Fr and configured to permit insertion of a second interventional medical device therethrough for performing an interventional medical procedure. The distal perfusion sheath and cannula combination device further may include a second sidearm comprising a Luer connector having a size between 8 Fr and 14 Fr, the second sidearm angled relative to the longitudinal axis of the second elongated shaft and defining a fourth inlet, a fourth outlet, and a fourth lumen extending between the fourth inlet and the fourth outlet. The fourth lumen may be fluidically coupled to the third lumen at the proximal region of the second elongated shaft.

In addition, the system may include a tubing having a first end configured to be coupled to the port, and a second end configured to be coupled to the Luer connector of the second sidearm, the tubing configured to redirect at least some blood flow from the second lumen through the tubing into the fourth lumen of the second sidearm and into the third lumen of the second elongated shaft and out the third outlet for perfusion of the patient's distal extremities. In addition, the distal perfusion sheath and cannula combination device may include a first port fluidically coupled to the third lumen at the proximal region of the second elongated shaft, the first port angled towards the third inlet to permit fluid flow therethrough to washout stasis regions of blood within the third lumen, and a second port fluidically coupled to the fourth lumen of the second sidearm.

In accordance with one aspect, a connector hub for selectively directing blood flow and enabling an interventional medical procedure is provided. The connector hub may comprise a first inlet, a first outlet, and a first lumen extending therebetween, a collinear port at the first inlet configured to receive an interventional medical device therethrough in a sheath mode for performing the interventional medical procedure, a sidearm defining a second inlet, a second outlet fluidically coupled to the first lumen, and a second lumen extending between the second inlet and the second outlet, the second lumen angled relative to a longitudinal axis of the first lumen and sized and shaped to direct blood flow from the second inlet into the first lumen and out the first outlet in a cannula mode, and a connection portion at the first outlet configured to be removably coupled to an inlet of a return cannula, to fluidically couple the first and second inlets and the return cannula.

The connector hub further may comprise a first port fluidically coupled to the first lumen, the first port angled towards the collinear port to permit fluid flow therethrough to washout stasis regions of blood within the collinear port. Moreover, the connector hub may comprise a male-to-male connector having a first end configured to be fluidically coupled to the first port, and a second end configured to be fluidically coupled to a male end of a stopcock. Further, the connector hub may comprise a second port fluidically coupled to the second lumen of the sidearm. For example, the second port may be configured to be coupled to a perfusion cannula configured to redirect at least some blood flow from the second lumen through the perfusion cannula for perfusion of the patient's distal extremities in the cannula mode.

Additionally, the connector hub may comprise a tubing having a first end configured to be coupled to the first port, and a second end configured to be coupled to the second port, the tubing configured to redirect at least some blood flow from the second lumen through the tubing into the first lumen towards the collinear port to washout stasis regions of blood within the collinear port in the cannula mode. For example, the first end of the tubing may be configured to be removably coupled to the first port, and the second end of the tubing may be configured to be removably coupled to the second port.

Moreover, when the connection portion is removably coupled to the inlet of the return cannula, the connection portion may be configured to form a fluid tight seal with the inlet of the return cannula. In addition, the first lumen may comprise a diameter between 12 Fr and 32 Fr. The second inlet of the sidearm may be configured to be fluidically coupled to a cardiopulmonary bypass system, e.g., an ECMO circuit. Additionally, the return cannula may comprise a distal region configured to be inserted into a patient's vasculature, such that, when the connection portion is removably coupled to the inlet of the return cannula, an outlet at the distal region of the return cannula is collinear with the first inlet of the connector hub. The connector hub further may comprise a hemostatic valve configured to be removably coupled to the first inlet, the hemostatic valve comprising a locking mechanism and configured to sealably receive the interventional medical device therethrough in the sheath mode.

BRIEF DESCRIPTION OF THE DRAWINGS

FIG. 4A illustrates an exemplary hemostatic valve cap of the hybrid system of FIG. 1A, FIG. 4B illustrates the valve membrane of the hemostatic valve cap of FIG. 4A, and FIG. 4C illustrates insertion of a medical device within the combination device via the hemostatic valve cap in accordance with some embodiments.

DETAILED DESCRIPTION

Figure 1A:
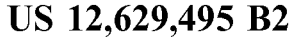
FIG. 1A illustrates an exemplary hybrid system having a sheath and cannula combination device with an angled sidearm to direct blood flow and a collinear port to enable a medical procedure, constructed in accordance with some embodiments.

Systems including a sheath and cannula combination device for permitting a user to select between directing blood flow through a first cannula portion of the combination device in a cannula mode and enabling an interventional medical procedure through a second sheath portion of the combination device in a sheath mode, or performing both simultaneously, are provided. For example, the sheath portion of the combination device may be dimensioned to receive a large bore interventional medical device, e.g., a catheter for coronary, peripheral, or cerebral vascular or valvular interventions (e.g., transcatheter heart valve repair/replacement including TAVR, TMVR, thrombectomy, annuloplasty rings, heart valve clips, etc.), an ECMO cannula, an endovascular catheter, and/or a pneumatic, rotary, or transvalvular flow pump, or venous intervention such as thrombectomy or electophysiologic procedure therethrough, e.g., via a hemostatic valve. Preferably, the inlet of the sheath portion is coaxial with the outlet of the combination device, such that the interventional medical devices may be inserted through the hemostatic valve linearly without having to bend as is the case with previous known connectors, as described above, thereby preventing kinking or catheter disruption, and permitting insertion of larger bore interventional medical devices. Moreover, the cannula portion of the combination device may be fluidically coupled to a cardiopulmonary bypass system, e.g., a conventional ECMO circuit, without interruption of the co-axial pathway for interventional equipment to direct blood flow out the outlet of the combination device for perfusion of the patient's vasculature during ECMO.

The system further may include a series of removable caps/plugs for temporarily sealing the cannula and/or sheath portions of the combination device, such that the user may seamlessly select when to use the combination device in the cannula mode, the sheath mode, both the cannula and sheath modes simultaneously, or neither the cannula mode nor the sheath mode. For example, when coupled to the combination device, the respective cap/plug may seal the respective portion of the combination device in manner that prevents pooling of blood within the combination device, while not interrupting operation of the combination device in the other mode via the unsealed portion of the combination device. Accordingly, the user may select to use the combination device in the sheath mode to deliver an interventional medical device through the hemostatic valve of the sheath portion of the combination device and into the patient's vasculature to a target location within the patient, and if/when ECMO is required, the user may select to connect the cannula portion of the combination device to a conventional ECMO circuit to direct blood flow therethrough in the cannula mode for perfusion via the patient's vasculature, without having to create an additional puncture in the patient, without having to remove the interventional medical device from the patient, and without the need to clamp across interventional equipment to enable a wet-to-wet connection with the ECMO circuit. Moreover, if the interventional medical device is no longer needed, it may be removed from the patient via the combination device without having to interrupt ECMO via the combination device, and optionally, the hemostatic valve may be capped or, alternatively replaced with a cap. Similarly, if ECMO is no longer needed, the combination device may be clamped, and the cannula portion of the combination device disconnected from the ECMO circuit and capped without interrupting operation of the combination device in the sheath mode.

Referring now to FIG. 1A, system 10 having sheath and cannula combination device 100 for selectively directing blood flow in a cannula mode, and enabling a large bore interventional medical procedure in a sheath mode is provided. Combination device 100 may include elongated shaft 110 having a proximal region having inlet 103, a distal region having outlet 111, e.g., at the distal end of elongated shaft 110, and a lumen extending therethrough along a longitudinal axis of elongated shaft 110 between inlet 103 and outlet 111, such that inlet 103 is in fluid communication with outlet 111. The distal region of elongated shaft 110 is configured to be in fluid communication with a patient's vasculature, e.g., an artery or vein, and outlet 111 may be disposed at a target location within the patient's vasculature. For example, the insertable distal region of elongated shaft 110 may have a length of between 10 cm to 55 cm, or preferably about 15 cm. Additionally, the outer surface of the insertable distal region of elongated shaft 110 may have a smaller diameter than the outer surface of the proximal region of elongated shaft 110, which remains external to the patient. Accordingly, elongated shaft 110 may include transition region 112, where the cross-sectional area of elongated shaft 110 transitions from the proximal region to the distal region. For example, the inserted distal portion of elongated shaft 110 may be inserted into the patient's vasculature and advanced until transition region 112 contacts the patient.

Moreover, the lumen of elongated shaft 110 may be dimensioned to receive a large bore interventional medical device, e.g., at least one of a catheter for coronary, peripheral, pulmonary, cerebral vascular or valvular interventions, or for placement of additional pump technologies within the left ventricle, such as a pneumatic or rotary flow pump inside the aorta, e.g., an intra-aortic balloon pump (IABPs), or trans-valvular rotary flow pump, e.g., Impella® pumps (made available by Abiomed, Inc. of Danvers, Massachusetts). For example, elongated shaft 110 may have a diameter between 8 Fr and 32 Fr, and preferably 12 Fr and 32 Fr. As shown in FIG. 1A, inlet 103 may be coaxial with outlet 111, such that the interventional medical device may be inserted through inlet 103 into the lumen of elongated shaft 110, and advanced towards and out of outlet 111 in the sheath mode without bending, thereby prevent undesirable bending and/or kinking of the large bore interventional medical device.

As shown in FIG. 1A, the proximal region of elongated shaft 110 may include connector hub 101, e.g., a multi-port connector, having collinear port 102 configured to receive the interventional medical device therethrough, and sidearm 104 fluidically coupled to the lumen of elongated shaft 110. For example, inlet 103 may be disposed at the proximal end of connector hub 101, such that the lumen of elongated shaft 110 extends from inlet 103 of collinear port 102 to outlet 111 at the distal end of the distal region of elongated shaft 110. As shown in FIG. 1A, sidearm 104 may be angled relative to the longitudinal axis of elongated shaft 110, e.g., ⅜″ angled, and may include sidearm inlet 105 configured to be removably coupled to cardiopulmonary bypass system, e.g., a conventional ECMO circuit, for directing blood flow from sidearm 104 into the lumen of elongated shaft 110, e.g., via an outlet of sidearm 104 in fluid communication with the lumen of elongated shaft 110, in a cannula mode. Preferably, sidearm 104 is angled relative to the longitudinal axis of elongated shaft 110 in a manner such that blood flows from sidearm 104 into the lumen of elongated shaft 110 and out outlet 111 smoothly.

In addition, connector hub 101 may include first port 108, e.g., a Luer port, having first port inlet 109 fluidically coupled to the proximal region of elongated shaft 110. As shown in FIG. 1A, first port 108 may be angled relative to the longitudinal axis of elongated shaft 110, such that first port 108 is angled towards collinear port 102 to permit fluid flow therethrough to washout stasis regions of blood within collinear port 102, e.g., during the cannula mode. For example, the flow path of first port 108 may be angled towards inlet 103, and accordingly, hemostatic valve 400, as described in further detail below. In addition, first port 108 may be configured for flushing and/or de-airing combination device 100 via collinear port 102. Moreover, connector hub 101 further may include second port 106, e.g., a Luer port 4 Fr to 12 Fr in diameter, having second port inlet/outlet 107, e.g., a Luer port 4 Fr to 12 Fr in diameter, fluidically coupled to sidearm 104. Accordingly, second port 106 may be configured to direct at least some blood flow from sidearm 104 and out outlet 107, e.g., for auto-washout of collinear port 102 via first port 108 or perfusion of the patient's distal extremities, as described in further detail below. Additionally, or alternatively, second port 106 may be configured for flushing and/or de-airing combination device 100 via sidearm 104. Connector hub 101 may be integrally formed with or permanently fixed to the proximal region of elongated shaft 110.

Figures 1B, 1C:
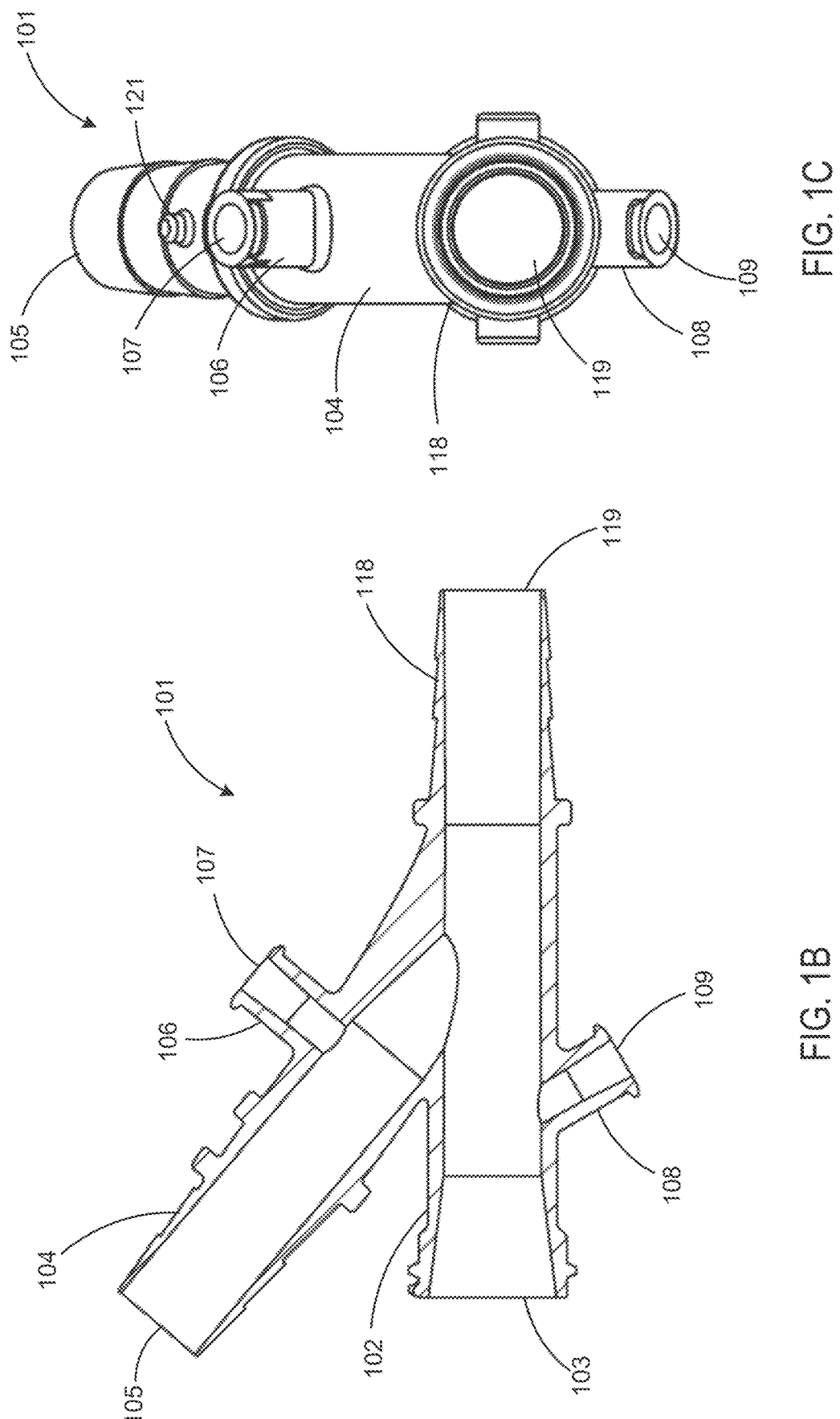
FIGS. 1B and 1C illustrate a universal connection hub of the hybrid system of FIG. 1A, constructed in accordance with some embodiments.

Alternatively, connector hub 101 may be configured to be removeably coupled to the proximal region of elongated shaft 110, such that connector hub 101 may be removably coupled to any standard arterial or venous return cannula, e.g., an ECMO cannula, and/or spliced into and out of any cardiopulmonary bypass (CPB) or VA/VV ECMO circuit via a short segment of standard tubing, e.g., a universal connector hub. For example, as shown in FIGS. 1B and 1C, the distal region of connector hub 101 may include an elongated shaft comprising connection portion 118 sized and shaped to be sealably and releasably coupled to the proximal region of any standard ECMO cannula and/or elongated shaft 110, to thereby fluidically couple inlet 103 of collinear port 102 with the outlet of the ECMO cannula, e.g., outlet 111 of elongated shaft 110, via outlet 119 at the distal end of connection portion 118. Connection portion 118 may have an outer diameter that is substantially equal to the inner diameter of the proximal end of the ECMO cannula, such that connection portion 118 may be releasably coupled to the ECMO cannula via insertion of connection portion 118 into the lumen of the ECMO cannula at the proximal end of the ECMO cannula, whereby a fluid tight seal is formed between the outer surface of connection portion 118 and the inner surface of the ECMO cannula. Alternatively, connection portion 118 may have an inner diameter that is substantially equal to the outer diameter of the proximal end of the ECMO cannula, such that connection portion 118 may be releasably coupled to the ECMO cannula via insertion of the proximal end of the ECMO cannula into the lumen of connection portion 118 via outlet 119, whereby a fluid tight seal is formed between the inner surface of connection portion 118 and the outer surface of the ECMO cannula.

Figure 1D:
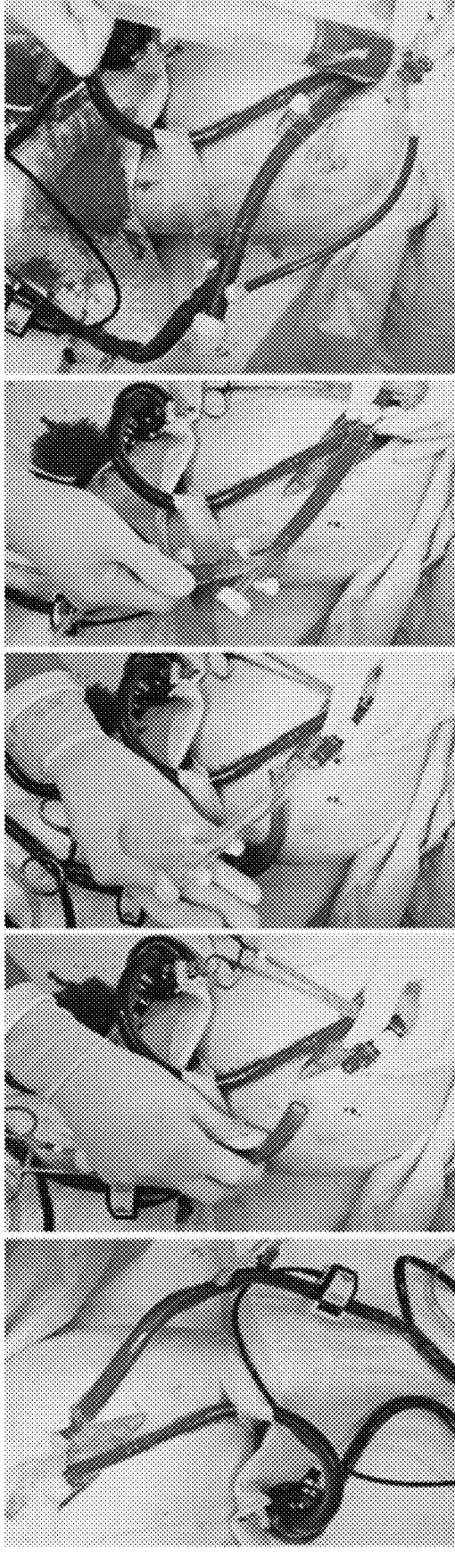
FIG. 1D illustrates splicing of the connection hub of the hybrid system into an existing ECMO circuit.

Accordingly, universal connector hub 101 provides clinical versatility by, for example, enabling single access Extracorporeal Membrane Oxygenation and use of a micro-axial flow pump such as an Impella, whereby an ECMO circuit may be used to deliver an Impella pump into the arterial or venous circulation. Arterial delivery of an Impella with ECMO allows for simultaneous activation of the Impella and ECMO, known as EC-Pella. Venous delivery enables OXY-RP by allowing for delivery of RP through a venous cannula and connecting to VV-ECMO, e.g., Breethe (made available by Abiomed, Inc. of Danvers, Massachusetts) if needed. Further, the universal connector hub enables use of a telescoping dual-lumen cannula, e.g., whereby a 15-19 Fr cannula may be delivered via connector hub 101 through a 24+ Fr venous cannula to convert a single lumen cannula into a dual-lumen cannula, e.g., Protek-Duo cannula (made available by LivaNova of London, United Kingdom), Spectrum cannula (made available by Spectrum Medical of Fairfax, Virginia), or Avalon cannula (made available by Getinge of Göteborg, Sweden). For example, FIG. 1D illustrates splicing connector hub 101 into an existing ECMO circuit. In addition, as shown in FIG. 1C, the outer surface of sidearm 104 may include notch 121 sized and shaped to be received by a corresponding channel of a sidearm extender to facilitate alignment of the sidearm extender relative to connector hub 101 when the sidearm extender is coupled to connector hub 101, as described in further detail below with regard to FIG. 12F.

Referring again to FIG. 1A, system 10 further may include first port cap 116 for releasably sealing inlet 109 of first port 108, second port cap 114 for releasably sealing outlet 107 of second port 106, tubing 120 for fluidically coupling first port 108 and second port 106, collinear port delivery cap 200 for releasably sealing collinear port 102, e.g., during insertion of the distal region of elongated shaft 110 into the patient, collinear port cap 300 for releasably sealing collinear port 102, e.g., when combination device 100 is not in the sheath mode, sidearm cap 310 for releasably sealing sidearm 104, e.g., when combination device 100 is not in the cannula mode, hemostatic valve 400 configured to be removably coupled to inlet 102, and male-to-male connector 902 configured to be removably coupled to inlet 109 of first port 108 to fluidically couple combination device 100 to, e.g., a stopcock, as described in further detail below. For example, first port cap 116 may comprise a threaded mating surface configured to releasably engage with a corresponding threaded mating surface at inlet 109 of first port 108, e.g., when first port 108 is not in use, and second port cap 114 may comprise a threaded mating surface configured to releasably engage with a corresponding threaded mating surface at outlet 107 of second port 106, e.g., when second port 106 is not in use. In some embodiments, first port cap 116 and second port cap 114 may be structurally identical, and accordingly, interchangeable. In addition, system 10 further may include one or more sensors, e.g., pressure, flow, and/or oximeter sensors, disposed on, e.g., elongated shaft 110. Accordingly, system 10 may include an external console configured to be operatively coupled to the one or more sensors for receiving data measured via the one or more sensors.

Figure 2A:
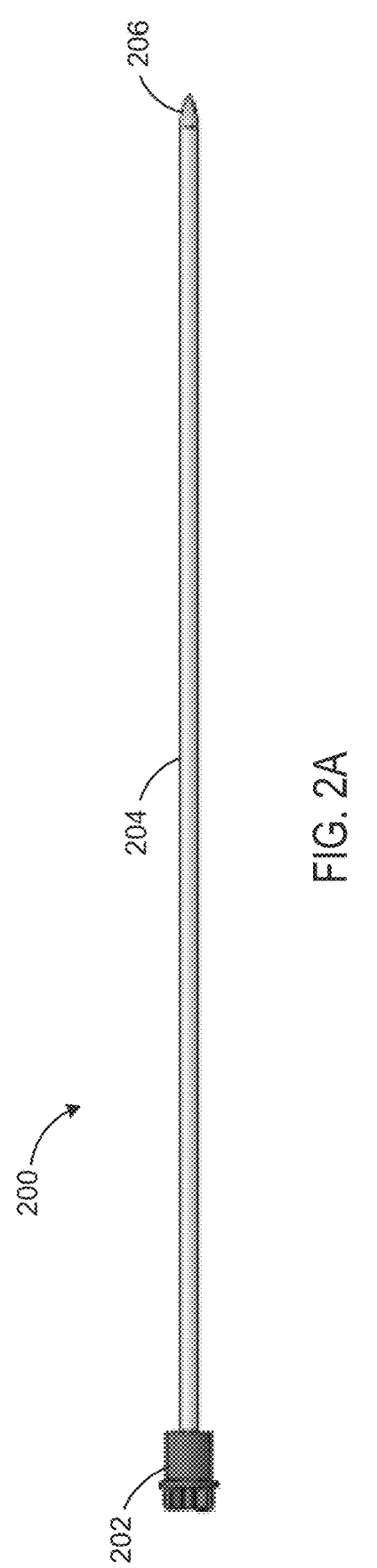
FIG. 2A illustrates an exemplary collinear port delivery obturator of the combination device of FIG. 1A.
Figure 2B:
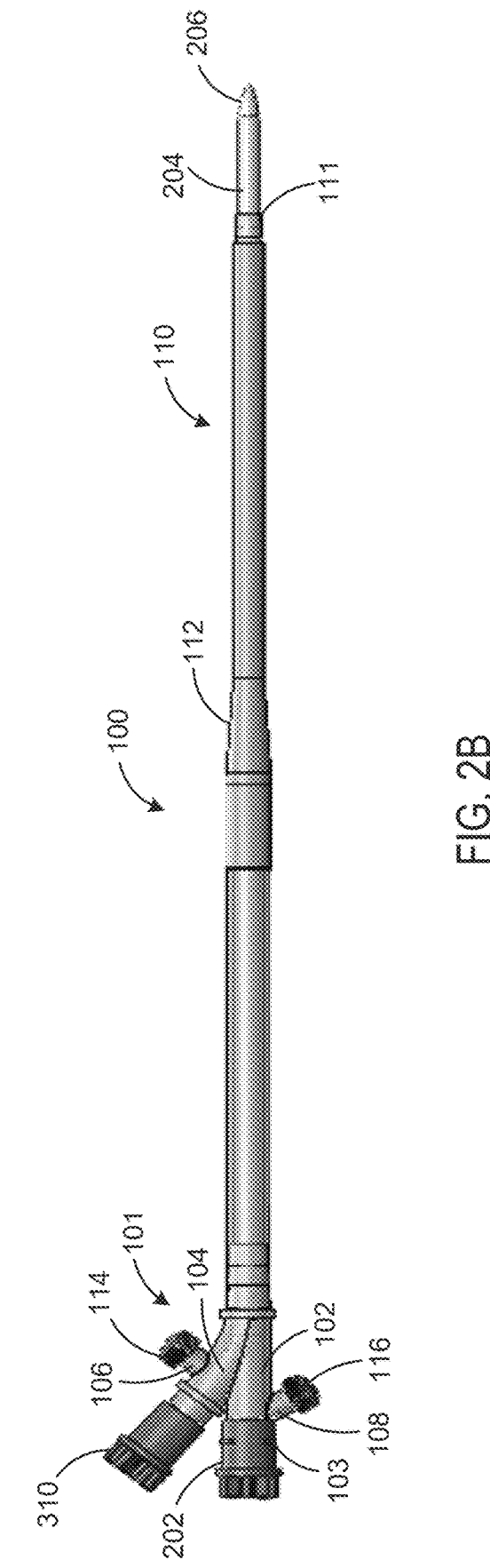
FIG. 2B illustrates the collinear port delivery obturator coupled to the combination device.

Referring now to FIGS. 2A and 2B, collinear port delivery cap 200 for releasably sealing collinear port 102 is provided. As shown in FIG. 2A, collinear port delivery cap 200 includes cap portion 202 configured to be removably coupled to inlet 103 of collinear port 102 to seal collinear port 102, e.g., during insertion of the distal region of elongated shaft 110 into the patient. For example, cap portion 202 may comprise a threaded mating surface configured to releasably engage with a corresponding threaded mating surface at inlet 103 of collinear port 102. Moreover, collinear port delivery cap 200 may include obturator 204 sized and shaped to be disposed within the lumen of elongated shaft 110, and having a length such that a distal end of obturator 204 extends beyond outlet 111 of elongated shaft 110, as shown in FIG. 2B, thereby providing additional stiffness to elongated shaft 110 as elongated shaft 110 is inserted into the patient's vasculature. As shown in FIGS. 2A and 2B, the distal end of obturator 204 may comprise atraumatic tip 206 configured to facilitate insertion of elongated shaft 110 into the patient's vasculature while minimizing/preventing injury to the patient's vasculature. In some embodiments, the same collinear port delivery cap may be configured to be removably coupled to inlet 105 of sidearm 104, such that obturator 204 is disposed within the lumen of sidearm 104 and at least a portion of the lumen of elongated shaft 110, e.g., during insertion of elongated shaft 110 into the patient's vasculature.

Figure 3A:
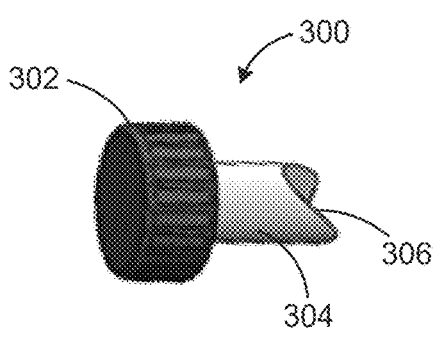
FIG. 3A illustrates an exemplary collinear port obturator cap of the hybrid system of FIG. 1A constructed in accordance with some embodiments.

Referring now to FIG. 3A, collinear port cap 300 for releasably sealing collinear port 102 is provided. As shown in FIG. 3A, collinear port cap 300 includes cap portion 302 configured to be removably coupled to inlet 103 of collinear port 102 to seal collinear port 102, e.g., when combination device 100 is not in the sheath mode. For example, cap portion 302 may comprise a threaded mating surface configured to releasably engage with a corresponding threaded mating surface at inlet 103 of collinear port 102. Moreover, collinear port cap 300 may include obturator 304 sized and shaped to be disposed within at least a portion of the lumen of elongated shaft 110 within collinear port 102 to thereby prevent pooling of blood within collinear port 102, e.g., during the cannula mode. In addition, obturator 304 may have a length such that a distal end of obturator 304 does not obstruct the blood flow path between the lumen of sidearm 104 and the lumen of elongated shaft 110, as shown in FIGS. 3E and 3F.

As shown in FIG. 3A, distal end 306 of obturator 304 may have a beveled geometry corresponding to a geometry of the lumen of sidearm 104, and further may be configured to facilitate smooth blood flow from sidearm 104 to the lumen of elongated shaft 110 in the cannula mode. For example, at least a portion of the edge of distal end 306 of obturator 304 may have a curved profile configured to align with the lumen of sidearm 104, and at least a portion of the surface of distal end 306 of obturator 304 may comprise a ramped and/or curved profile to facilitate smooth blood flow from the lumen of sidearm 104 into the lumen of elongated shaft 110. Moreover, collinear port cap 300 may be configured to be coupled to inlet 103 of collinear port 102 in a manner that automatically aligns beveled distal end 306 with the lumen of sidearm 104. For example, the threaded mating surface of cap portion 302 may be configured to permit collinear port cap 300 to be rotated to a final position, such that beveled distal end 306 is aligned with the lumen of sidearm 104.

Figure 3B:
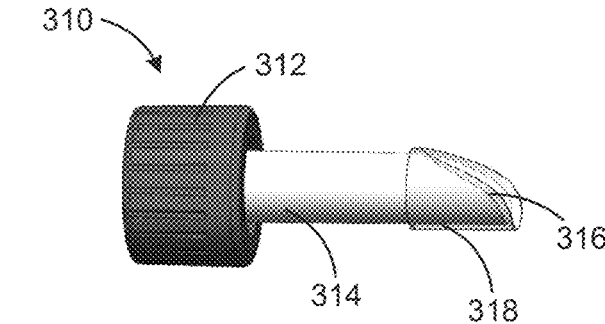
FIG. 3B illustrates an exemplary sidearm obturator cap of the hybrid system of FIG. 1A constructed in accordance with some embodiments.
Figure 3C:
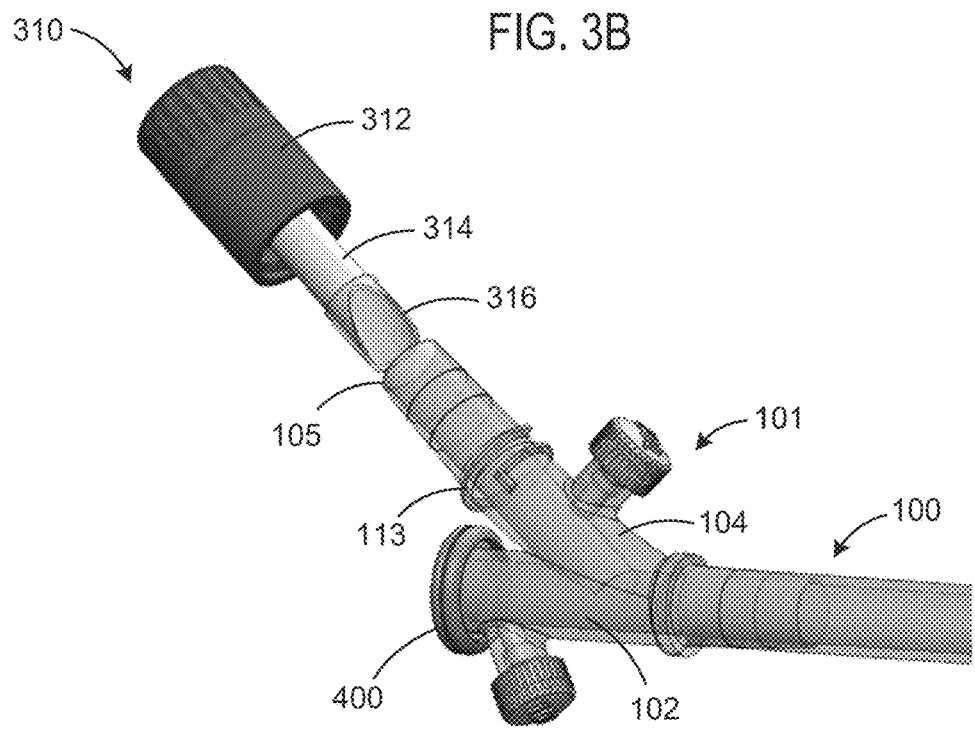
FIGS. 3C and 3D illustrates coupling of the sidearm obturator cap of FIG. 3B to the angled sidearm of the combination device.
Figure 3D:
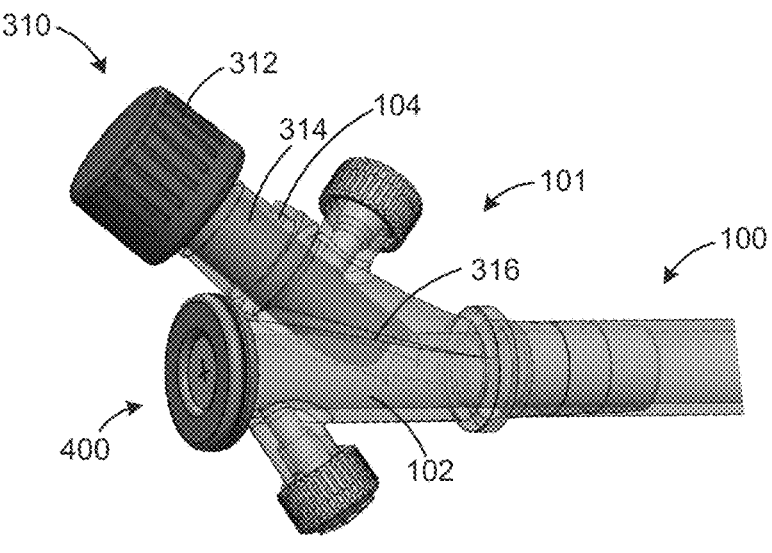
Figure 3E:
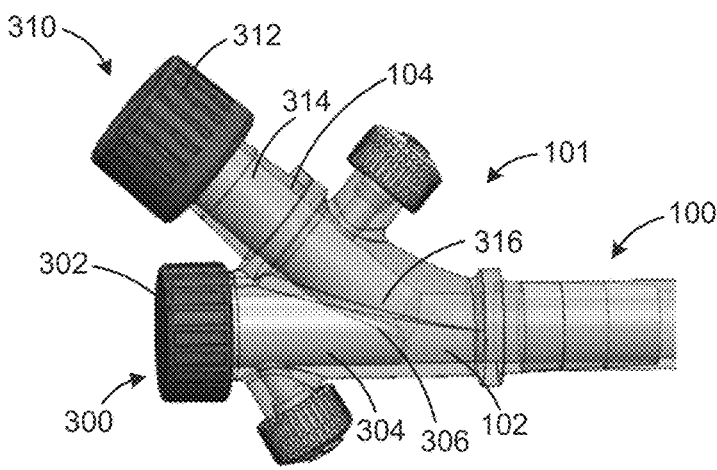
FIGS. 3E and 3F illustrate the collinear port obturator cap and the sidearm obturator cap coupled to the combination device.
Figure 3F:
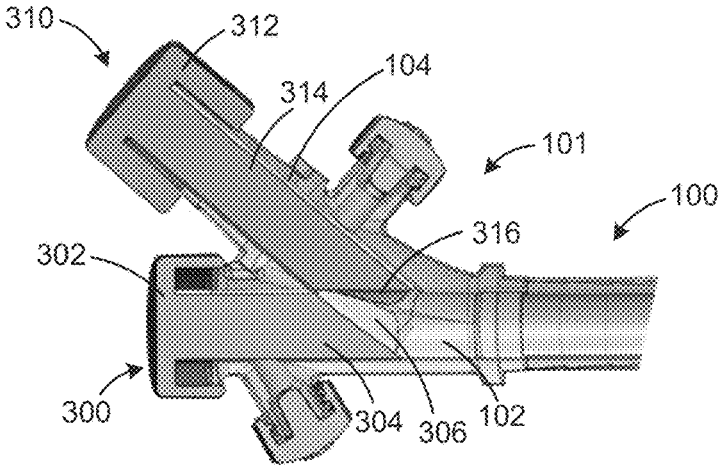

Referring now to FIG. 3B, sidearm cap 310 for releasably sealing sidearm 104 is provided. As shown in FIG. 3B, sidearm cap 310 includes cap portion 312 configured to be removably coupled to inlet 105 of sidearm 104 to seal sidearm 104, e.g., when combination device 100 is not in the cannula mode. For example, cap portion 312 may comprise a threaded mating surface configured to releasably engage with a corresponding threaded mating surface at inlet 105 of sidearm 104. Moreover, sidearm cap 310 may include obturator 314 sized and shaped to be disposed within the lumen of sidearm 104 to thereby prevent pooling of blood within sidearm 104, e.g., during the sheath mode. In addition, obturator 314 may have a length such that distal end 316 of obturator 314 does not obstruct the lumen of elongated shaft 110, as shown in FIG. 3C. As shown in FIG. 3B, distal end 316 of obturator 314 may have a beveled geometry corresponding to a geometry of the lumen of elongated shaft 110. For example, at least a portion of the surface of distal end 316 of obturator 314 may comprise a curved profile configured to align with and define the inner surface of the lumen of elongated shaft 110 when obturator 314 is disposed within the lumen of sidearm 104, as shown in FIG. 3D.

In addition, at least the distal region of obturator 314 may include hemostatic cover 318 configured to make sidearm 104 hemostatic when sidearm cap 310 is coupled to sidearm 104. For example, hemostatic cover 318 may be made of a biocompatible elastomer such as silicone or thermoplastic elastomer (TPE). As will be understood by a person having ordinary skill in the arm, the other obturator caps described herein, e.g., collinear port cap 300 and sidearm extender cap 1210 as described in further detail below with regard to FIG. 12A, may similarly include a hemostatic cover. As shown in FIG. 3C, sidearm cap 310 may be configured to be coupled to inlet 105 of sidearm 104 in a manner that automatically aligns beveled distal end 316 with the lumen of elongated shaft 110. For example, the threaded mating surface of sidearm 104, e.g., threaded surface 113, may be configured to permit sidearm cap 310 to be rotated to a final position, such that beveled distal end 316 is aligned with the lumen of elongated shaft 110. As will be understood by a person having ordinary skill in the arm, the other ports for receiving an obturator cap described herein, e.g., collinear port 102 and sidearm extenders 700, 800 as described in further detail below with regard to FIGS. 7A and 8, may similarly include a threaded surface configured to permit auto-alignment of the respective obturator caps. FIGS. 3E and 3F illustrate collinear port cap 300 and sidearm cap 310 coupled to collinear port 102 and sidearm 104, respectively.

Figure 4D:
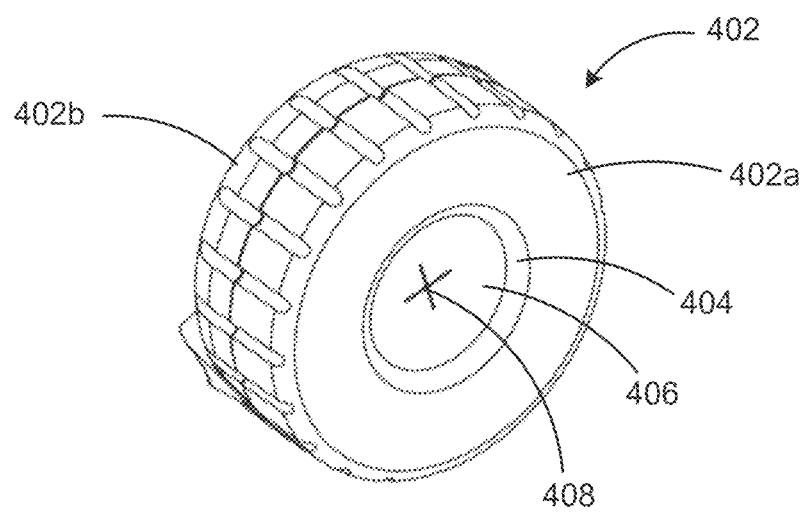
FIGS. 4D and 4E illustrates an alternative exemplary hemostatic valve cap of the hybrid system.

Referring now to FIGS. 4A to 4E, hemostatic valve 400 for preventing backflow of blood through elongated shaft 110, e.g., during insertion of an interventional medical device in the sheath mode is provided. As shown in FIG. 4A, hemostatic valve 400 may include cap portion 402 configured to be removably coupled to inlet 103 of collinear port 102 when combination device 100 is in the sheath mode. For example, cap portion 402 may comprise a threaded mating surface (e.g., threaded surface 410 shown in FIG. 4E) configured to releasably engage with a corresponding threaded mating surface at inlet 103 of collinear port 102. In addition, cap portion 402 may be configured to house hemostatic valve membrane 406. For example, hemostatic valve membrane 406 may be made of a biocompatible elastomer such as silicone or thermoplastic elastomer (TPE). As shown in FIG. 4B, hemostatic valve membrane 406 may comprise perforation 408 configured to permit insertion of a large bore interventional medical device therethrough, while preventing backflow of blood across hemostatic valve membrane 406. For example, hemostatic valve membrane 406 may comprise one or more flat, elastomer discs having or more perforations 408, e.g., a cross hair.

Figure 4E:
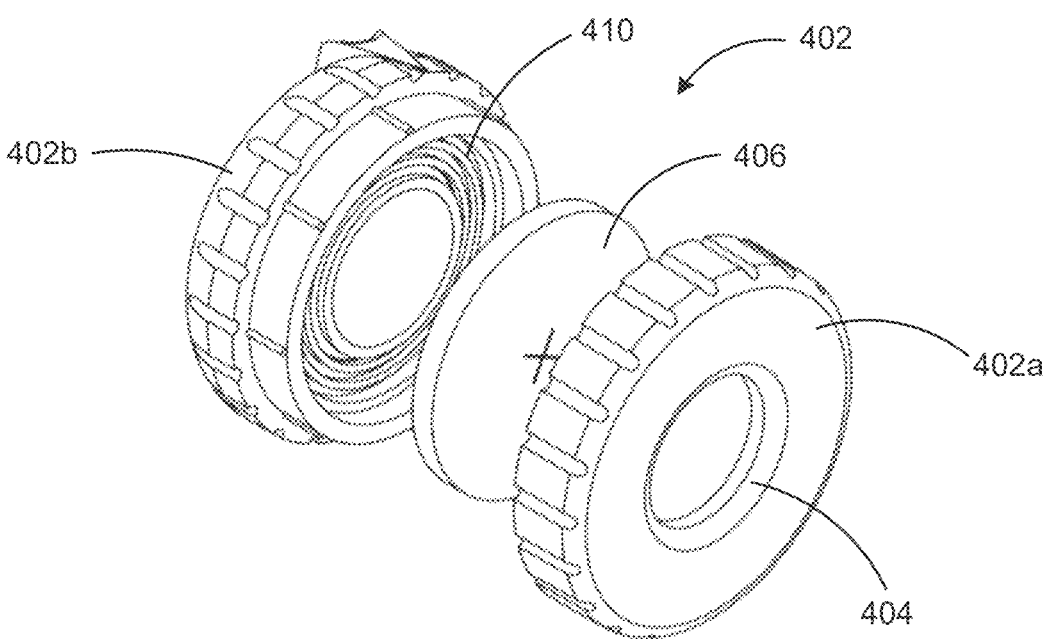

In some embodiments, two or three or more flat, elastomer discs may be layered/stacked to form hemostatic valve membrane 406. The two, three, or more discs may be stacked in a manner such that the respective perforations have different orientations relative to one another to optimize homeostasis. As shown in FIG. 4A, cap portion 402 may include opening 404 sized and shaped receive the interventional medical device therethrough, and to expose perforation 408 of hemostatic valve membrane 406. As shown in FIG. 4C, interventional medical device D may be inserted through perforation 408 of hemostatic valve membrane 406 via opening 404 of cap portion 402 of hemostatic valve 400 to perform an interventional medical procedure. In some embodiments, hemostatic valve 400 may be bonded to, or otherwise integrated with collinear port 102. The housing of cap portion 402 may be integrally formed as a single piece, or alternatively, cap portion 402 may be formed of first cap portion 402a having opening 404, and second cap portion 402b having threaded surface 410, as shown in FIGS. 4D and 4E, such that hemostatic valve membrane 406 may be disposed between first cap portion 402a and second cap portion 402b. Accordingly, first cap portion 402a and second cap portion 402b may be securely and/or releasably coupled together to enclose hemostatic valve membrane 406 therebetween.

In some embodiments, like collinear port cap 300, sidearm cap 310 may be decoupled from sidearm 104 and replaced with a hemostatic valve cap constructed similar to hemostatic valve 400 and configured to permit insertion of an interventional medical device, e.g., a micro-axial flow pump, therethrough into elongated shaft 110 via sidearm 104, while preventing backflow of blood through sidearm 104. For example, the sidearm hemostatic valve cap may be configured to permit insertion of, e.g., an Impella® pump (made available by Abiomed, Inc. of Danvers, Massachusetts), an ECMO cannula, and/or an endovascular catheter, therethrough. Accordingly, the sidearm hemostatic valve cap may include a cap portion configured to be removably coupled to inlet 105 of sidearm 104, and sized and shaped to house a hemostatic valve membrane. Moreover, the sidearm extender caps described herein, such as sidearm extender cap 1210 described in further detail below with regard to FIGS. 12A to 12E, may similarly be replaced with a hemostatic valve cap configured to permit insertion of an interventional medical device, e.g., a micro-axial flow pump, therethrough.

Figure 5A:
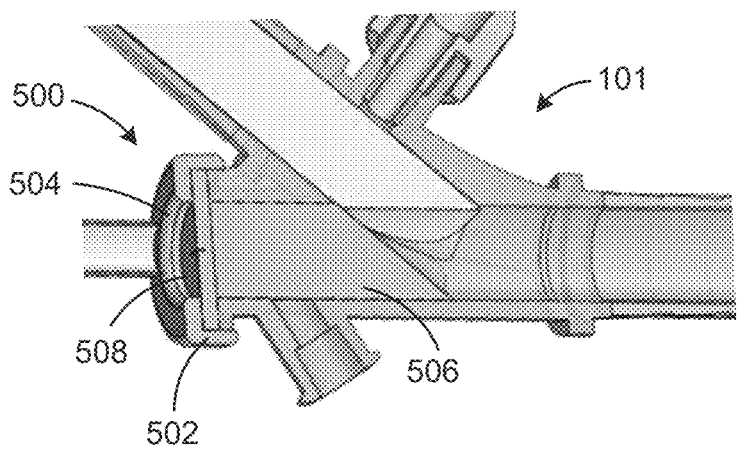
FIG. 5A illustrates an alternative exemplary hemostatic valve cap of the hybrid system having an obturator valve membrane.
Figure 5B:
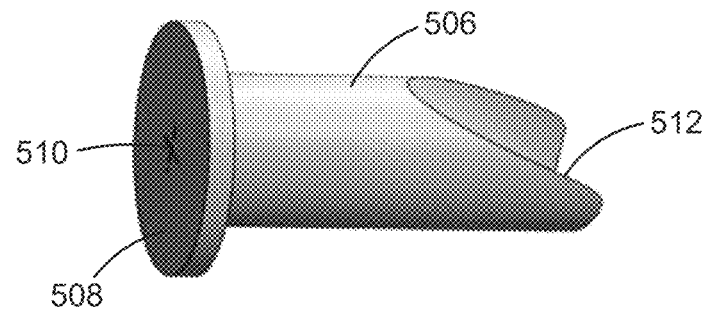
FIG. 5B illustrates the obturator valve membrane of the hemostatic valve cap of FIG. 5A.
Figure 5C:
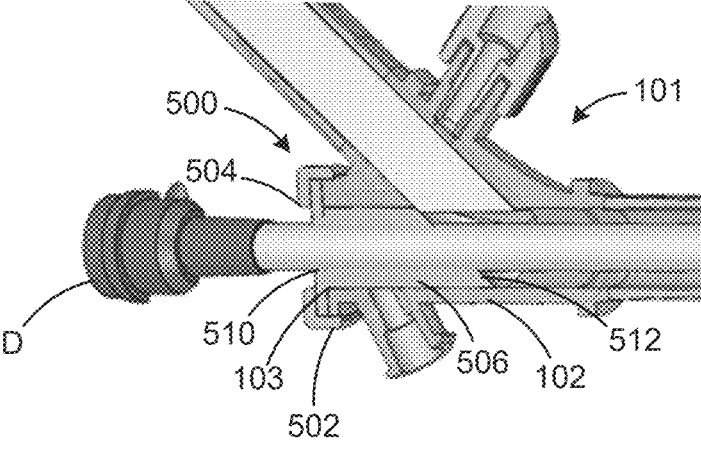
FIG. 5C illustrates insertion of a medical device within the combination device via the hemostatic valve cap of FIG. 5A in accordance with some embodiments.

Referring to FIGS. 5A to 5C, alternative exemplary hemostatic valve 500 for preventing backflow of blood through elongated shaft 110, e.g., during insertion of a large bore interventional medical device in the sheath mode is provided. Like hemostatic valve 400, hemostatic valve 500 may include cap portion 502 having opening 504 sized and shaped receive a large bore interventional medical device therethrough, and to expose the perforation of the hemostatic valve membrane housed within cap portion 502. Unlike hemostatic valve 400, the hemostatic valve membrane of hemostatic valve 500 may comprise duckbill valve membrane 508. For example, duckbill valve membrane 508 may be made of a biocompatible elastomer such as silicone or thermoplastic elastomer (TPE). As shown in FIG. 5B, duckbill valve membrane 508 may comprise obturator 506 having beveled distal end 512, and perforation 510 configured to permit insertion of a large bore interventional medical device therethrough, while preventing backflow of blood across duckbill valve membrane 508. As shown in FIG. 5C, interventional medical device D may be inserted through perforation 510 of duckbill valve membrane 508 via opening 504 of cap portion 502 of hemostatic valve 500 to perform an interventional medical procedure.

Moreover, like obturator 304 of collinear port cap 300, obturator 506 may be sized and shaped to be disposed within at least a portion of the lumen of elongated shaft 110 within collinear port 102 to thereby prevent pooling of blood within collinear port 102, e.g., during the cannula mode. Accordingly, the connector hub of the combination device may not require first port 108 fluidically coupled to the lumen of elongated shaft 110 for the purpose of auto-washout of collinear port 102 as described above. In addition, like obturator 304, obturator 506 may have a length such that a distal end of obturator 506 does not obstruct the blood flow path between the lumen of sidearm 104 and the lumen of elongated shaft 110, as shown in FIG. 5C.

Further, like beveled distal end 306 of obturator 304, beveled distal end 512 of obturator 506 may have a beveled geometry corresponding to a geometry of the lumen of sidearm 104, and further may be configured to facilitate smooth blood flow from sidearm 104 to the lumen of elongated shaft 110 in the cannula mode while combination device 100 is simultaneously in the sheath mode. For example, at least a portion of the edge of beveled distal end 512 of obturator 506 may have a curved profile configured to align with the lumen of sidearm 104, and at least a portion of the surface of beveled distal end 512 of obturator 506 may comprise a ramped and/or curved profile to facilitate smooth blood flow from the lumen of sidearm 104 into the lumen of elongated shaft 110. Moreover, hemostatic valve 500 may be configured to be coupled to inlet 103 of collinear port 102 in a manner that automatically aligns beveled distal end 512 with the lumen of sidearm 104. For example, the threaded mating surface of cap portion 502 may be configured to permit hemostatic valve 500 to be rotated to a final position, such that beveled distal end 512 is aligned with the lumen of sidearm 104.

Figure 6:
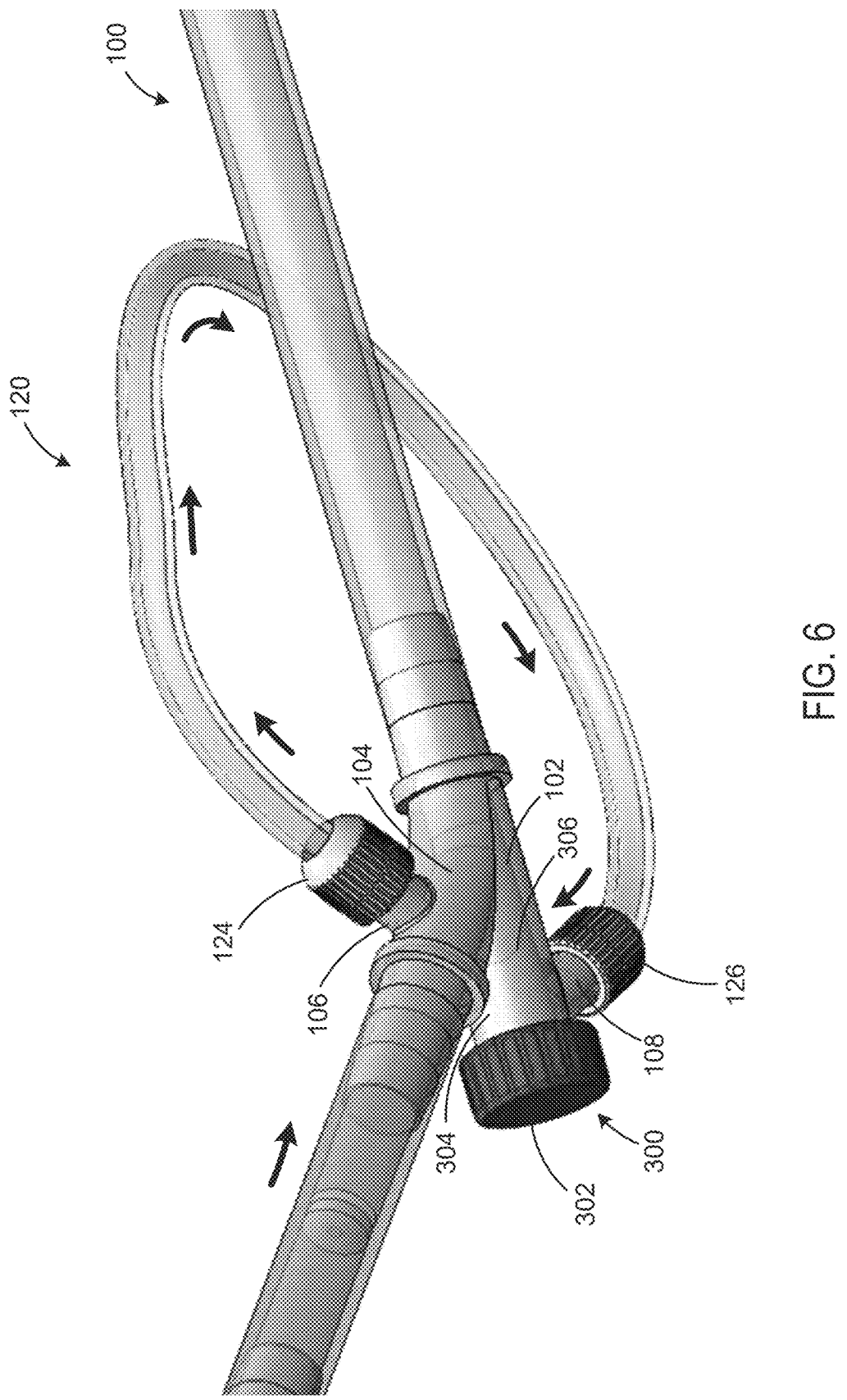
FIG. 6 illustrates an exemplary tubing fluidically coupled to a Luer port of the angled sidearm and an angled Luer port of the collinear port for washout to prevent stasis regions within the collinear port in accordance with some embodiments.

Referring now to FIG. 6, tubing 120 for auto-washing of collinear port 102 is provided. As shown in FIG. 6, a first end of tubing 120 may comprise first connector 124 configured to be removably coupled to second port 106, and a second end of tubing 120 may comprise second connector 126 configured to be removably coupled to first port 108, to thereby fluidically couple first port 108 and second port 106. Accordingly, during the cannula mode, at least some blood flow may be automatically directed from sidearm 104 into tubing 120 via second port 106 and first connector 124, and from tubing 120 into the lumen of elongated shaft 110 via first port 108 and second connector 126. As first port 108 is angled toward collinear port 102, such that the flow path of first port 108 is angled towards inlet 103 of elongated shaft 110, the redirected blood flow exiting tubing 120 into the lumen of elongated shaft 110 may automatically washout stasis regions of blood within collinear port 102 during the cannula mode. Moreover, each of first connector 124 and second connector 126 may include an extended portion, e.g., extended portion 122 of first connector 124 (FIG. 1A), sized and shaped to be disposed within and extend through at least a length of first port 106 and second port 108, respectively, when the first and second connector are coupled to first and second ports, respectively. Alternatively, one or both of first connector 124 and second connector 126 may not include an extended portion, to thereby preserve the largest flow path from connector hub 101 through tubing 120 via the first and second connectors.

Figure 7A:
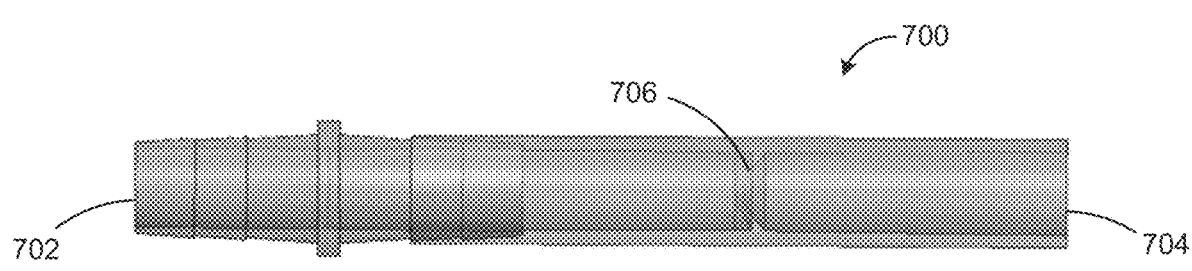
FIG. 7A illustrates an exemplary removable sidearm extender of the hybrid system.
Figure 7B:
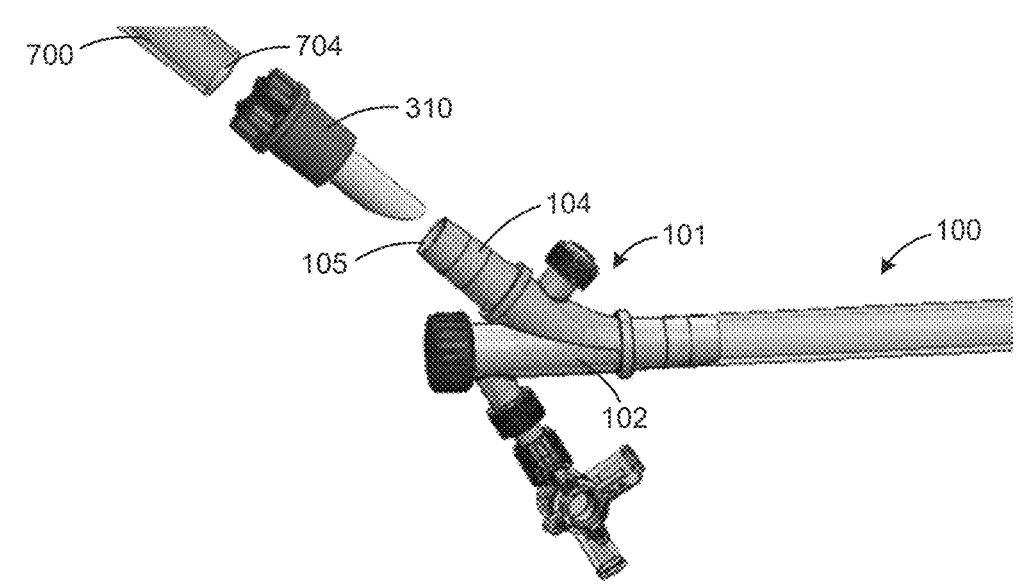
FIGS. 7B and 7C illustrate coupling of the removable sidearm extender to the angled sidearm of the combination device in accordance with some embodiments.
Figure 7C:
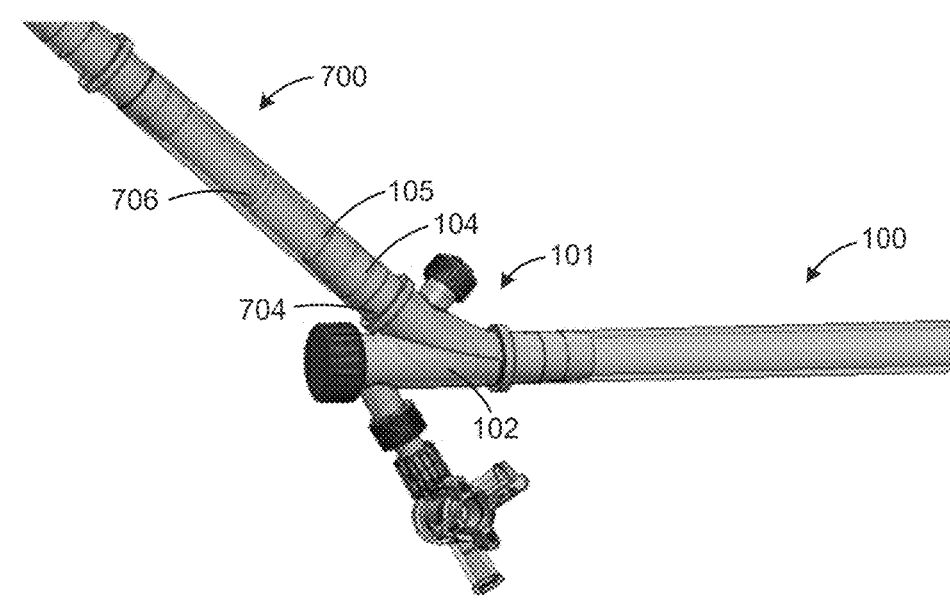

Referring now to FIGS. 7A to 7C, an exemplary sidearm extender for extending the effective length of sidearm 104 is provided. As shown in FIG. 7A, sidearm extender 700 may include sidearm extender inlet 702 configured to be removably coupled to a conventional ECMO circuit (e.g., in the same manner as inlet 105 of sidearm 104), sidearm extender outlet 704 configured to be fluidically coupled to inlet 105 of sidearm 104, and a lumen extending therethrough for directing blood flow from sidearm extender 700 into the lumen of elongated shaft 110 via sidearm 104 in the cannula mode. In addition, sidearm extender 700 may have one or more de-airing ports embedded therein. Moreover, sidearm extender 700 may include clamping portion 706 disposed between inlet 702 and outlet 704. Clamping portion 706 may be configured to be clamped, e.g., via an external clamping instrument, to stop blood flow through sidearm extender 700 during the cannula mode. Accordingly, rather than requiring the user to clamp the ECMO cannula, e.g., elongated shaft 110, as is the current practice to stop blood flow during ECMO, e.g., to connect/replace catheters fluidically coupled to the ECMO cannula and/or disconnect the ECMO cannula from the ECMO circuit, the user may clamp clamping portion 706. Specifically, it may be undesirable and/or impractical to clamp elongated shaft 110 to stop blood flow in the cannula mode while a large bore interventional medical device is disposed within the lumen of elongated shaft 110 in the sheath mode, as doing so may injure the interventional medical device.

As shown in FIG. 7B, sidearm extender 700 may be configured to be removably coupled to sidearm 104, such that the user may select to fluidically couple sidearm extender 700 to sidearm 104, e.g., when combination device 100 will need to be used in the sheath mode during the medical procedure in addition or in conjunction with the cannula mode, such that clamping of elongated shaft 110 would be undesirable and/or impractical as described above. For example, outlet 704 of sidearm extender 700 may comprise a threaded mating surface configured to releasably engage with a corresponding threaded mating surface at inlet 105 of sidearm 104. Accordingly, to couple sidearm extender 700 to sidearm 104, sidearm cap 310 (if used) may be decoupled from inlet 105 of sidearm 104, as shown in FIG. 7B, and then outlet 704 of sidearm extender 700 may be coupled to inlet 105 of sidearm 104, as shown in FIG. 7C. Accordingly, the sidearm cap may be configured to be removably coupled to the inlet of the integrated sidearm extender to seal the integrated sidearm extender, e.g., when the combination device is not in the cannula mode. In some embodiments, the sidearm extender may be formed integrally with or permanently fixed to the sidearm of combination device 100, e.g., sidearm extender 700 may be bonded to sidearm 400, as described in further detail below with regard to FIGS. 12A to 12F.

Figure 8A:
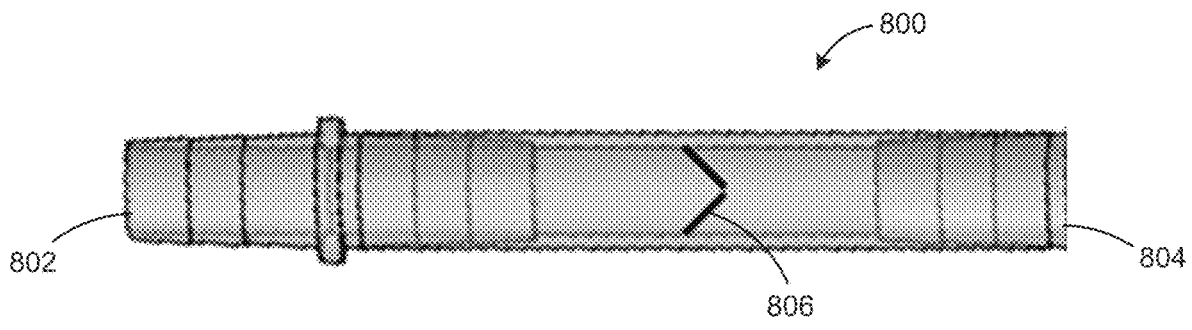
FIG. 8A illustrates an alternative exemplary sidearm extender of the hybrid system having a one-way valve.

Referring now to FIG. 8A, an alternative exemplary sidearm extender is provided. Sidearm extender 800 may be constructed similar to sidearm extender 700. For example, sidearm extender 800 may include sidearm extender inlet 802 configured to be removably coupled to a conventional ECMO circuit, sidearm extender outlet 804 configured to be fluidically coupled to inlet 105 of sidearm 104, and a lumen extending therethrough for directing blood flow from sidearm extender 800 into the lumen of elongated shaft 110 via sidearm 104 in the cannula mode. In addition, sidearm extender 800 may have one or more de-airing ports embedded therein. As shown in FIG. 8A, sidearm extender 800 may include valve 806 disposed within the lumen of sidearm extender 800, e.g., at a position between inlet 802 and outlet 804. For example, valve 806 may be a one-way directional valve configured to prevent backflow of blood through the lumen of sidearm extender 800. Combination device 100 may be used as an ECMO drainage cannula or an ECMO return cannula during the cannula mode. Accordingly, the direction of the one-way directional valve may be selected based on the desired direction of blood flow through sidearm extender 800. In some embodiments, valve 806 may be an actuatable valve operatively coupled to an external actuator configured to be actuated to transition valve 806 between an open state where blood flow through sidearm extender 800 is permitted, and a closed state where blood flow through sidearm extender 800 is prevented. Accordingly, rather than requiring the user to clamp the ECMO cannula, e.g., elongated shaft 110, valve 806 may be actuated to stop ECMO blood flow during the cannula mode. Like sidearm extender 700, sidearm extender 800 may be configured to be removably coupled to sidearm 104, or alternatively, may be integrally formed with sidearm 104.

Figure 8B:
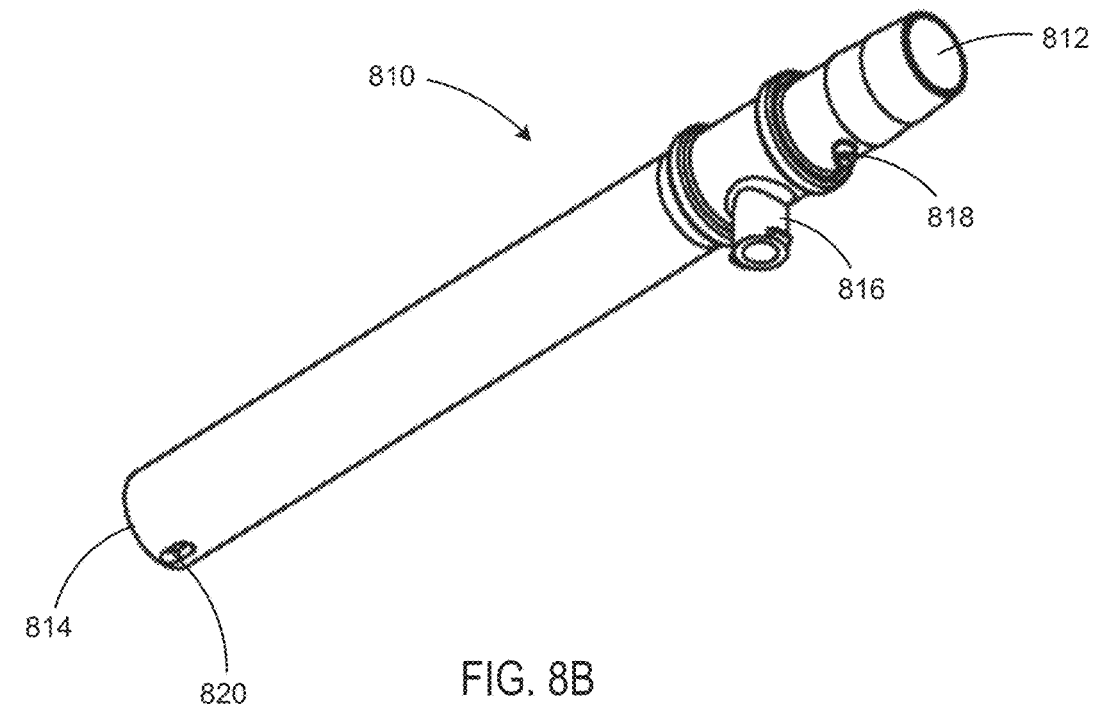
FIG. 8B illustrates an alternative exemplary sidearm extender of the hybrid system having a side port.

Referring now to FIG. 8B, another alternative exemplary sidearm extender is provided. Sidearm extender 810 may be constructed similar to sidearm extender 700. For example, sidearm extender 810 may include sidearm extender inlet 812 configured to be removably coupled to a conventional ECMO circuit, sidearm extender outlet 814 configured to be fluidically coupled to inlet 105 of sidearm 104, and a lumen extending therethrough for directing blood flow from sidearm extender 810 into the lumen of elongated shaft 110 via sidearm 104 in the cannula mode. As shown in FIG. 8B, sidearm extender 810 may include side port 816, e.g., a standard Luer connection. For example, side port 816 may be de-airing port. In addition, the outer surface of sidearm extender 810 at the proximal region of sidearm extender 810 may include notch 818 sized and shaped to be received by a corresponding channel of the corresponding obturator cap to thereby automatically align the beveled distal end of the corresponding obturator cap with the lumen of the elongated shaft such that flow is not disrupted through the elongated shaft, as described in further detail below with regard to FIG. 12F. Moreover, the distal region of sidearm extender 810 further may include opening 820 sized and shaped to receive notch 121 of connector hub 101 to facilitate alignment of sidearm extender 810 relative to connector hub 101 when sidearm extender 810 is coupled to connector hub 101, and accordingly, to ensure that the beveled distal end of the corresponding obturator cap is properly aligned with the lumen of the elongated shaft when the corresponding obturator cap is coupled to sidearm extender 810 via notch 818 and the corresponding channel of the corresponding obturator cap.

Figure 9A:
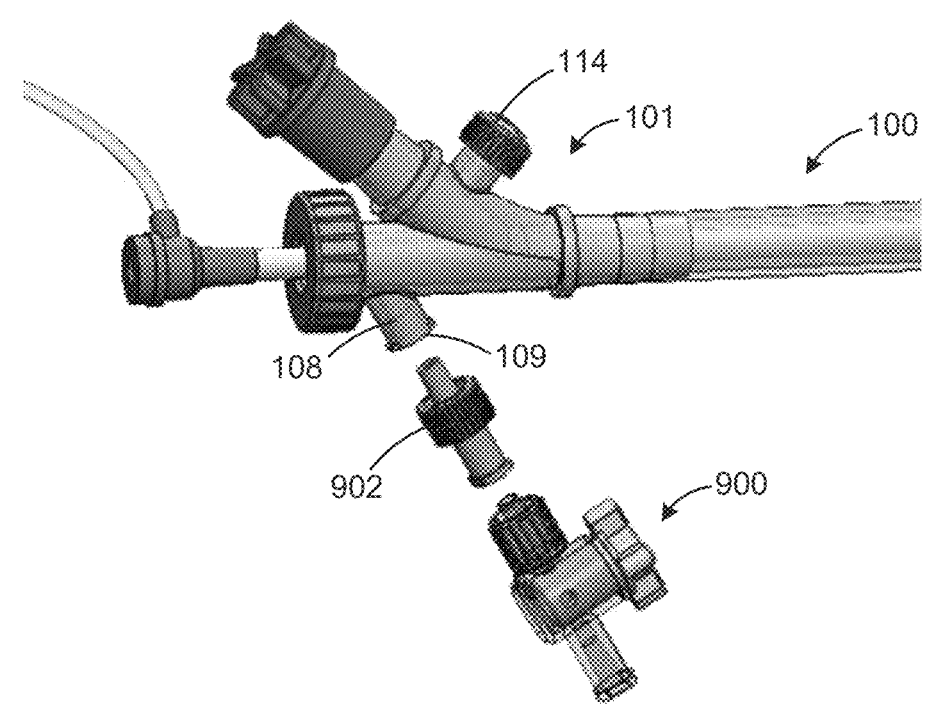
FIGS. 9A and 9B illustrate coupling of a stopcock to a Luer port of the combination device via a male-to-male connector in accordance with some embodiments.
Figure 9B:
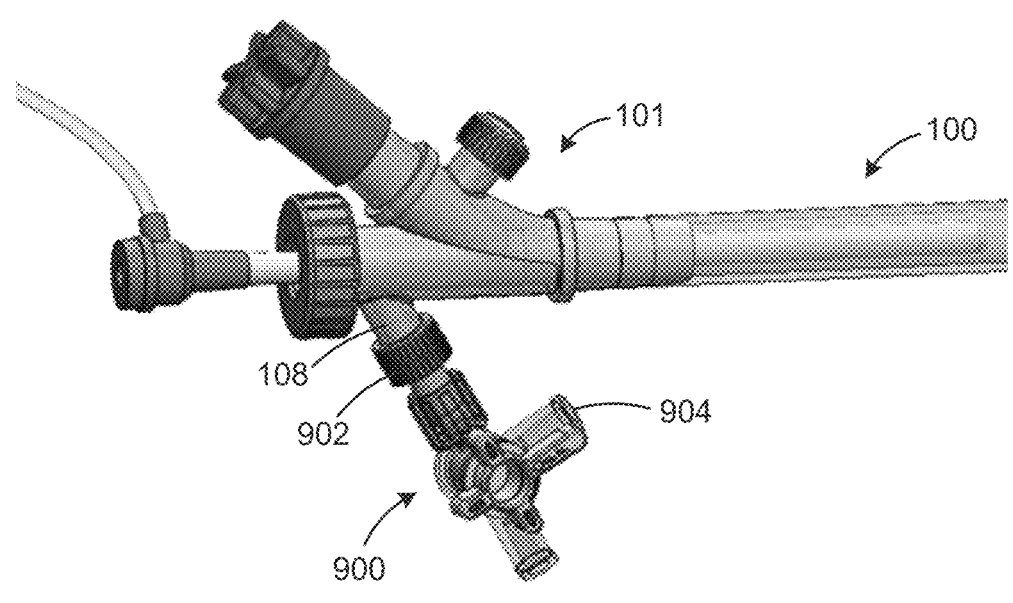

Referring now to FIGS. 9A and 9B, male-to-male connector 902 is provided. Connector 902 may be configured to be removably coupled to inlet 109 of first port 108 to enable fluidic coupling of combination device 100 to standard 2-, 3- or 4-way stopcocks, e.g., stopcock 900, via the 4 Fr to 12 Fr port. For example, a first male end of connector 902 may be configured to be removably coupled to inlet 109 of first port 108, e.g., a female end, and a second female end of connector 902 may be configured to be removably coupled to a male end of stopcock 900, to thereby fluidically coupled stopcock 900 to first port 108 of combination device 100.

Accordingly, stopcock 900 may fluidically couple combination device 100 to one or more instruments for, e.g., measuring pressure, sampling blood, infusing drugs, etc. As will be understood by a person having ordinary skill in the art, connector 900 may similarly be removably coupled to second port 106 to thereby fluidically coupled second port 106 to, e.g., stopcock 900. In addition, stopcock 900 may be coupled to second port 108 via connector 902 while first connector 124 of tubing 120 is coupled to side arm 104 and second connector 126 of tubing 120 is coupled to inlet 904 of stopcock 900, such that the combination device may have access to this blood flow for antegrade perfusion while also performing auto-washout via tubing 120.

Figure 10A:
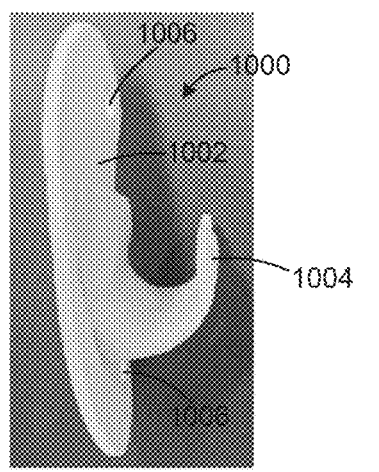
FIG. 10A illustrates an exemplary fixation pad for coupling the combination device to a patient.
Figure 10B:
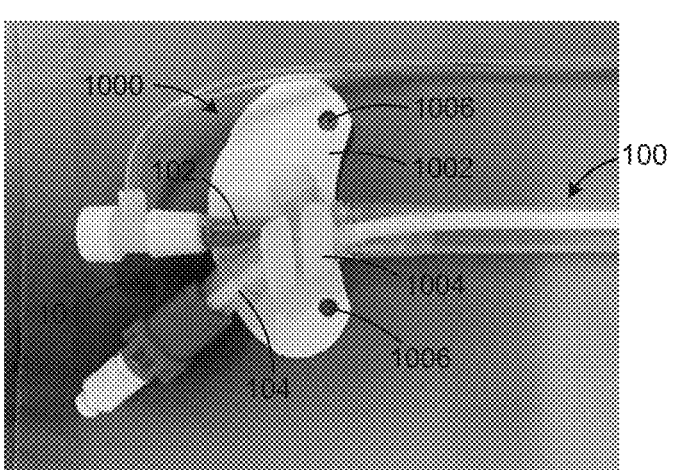
FIG. 10B illustrates the combination device coupled to the fixation pad of FIG. 10A.

Referring now to FIGS. 10A and 10B, system 10 further may include fixation pad 1000 configured to affix combination device 100 to the patient's skin. Fixation pad 1000 may include pad 1002 sized and shaped to be fixed to the patient's skin. For example, pad 1002 may include one or more suture holes 1006 configured to receive one or more sutures or zip ties for coupling fixation pad 1000 to the patient's skin. In addition, fixation pad 1000 may include one or more hooks 1004 configured to receive at least a portion of combination device 100, e.g., connector hub 101, therein to secure combination device 100 to fixation pad 1000, and accordingly to the patient's skin.

Figure 11:
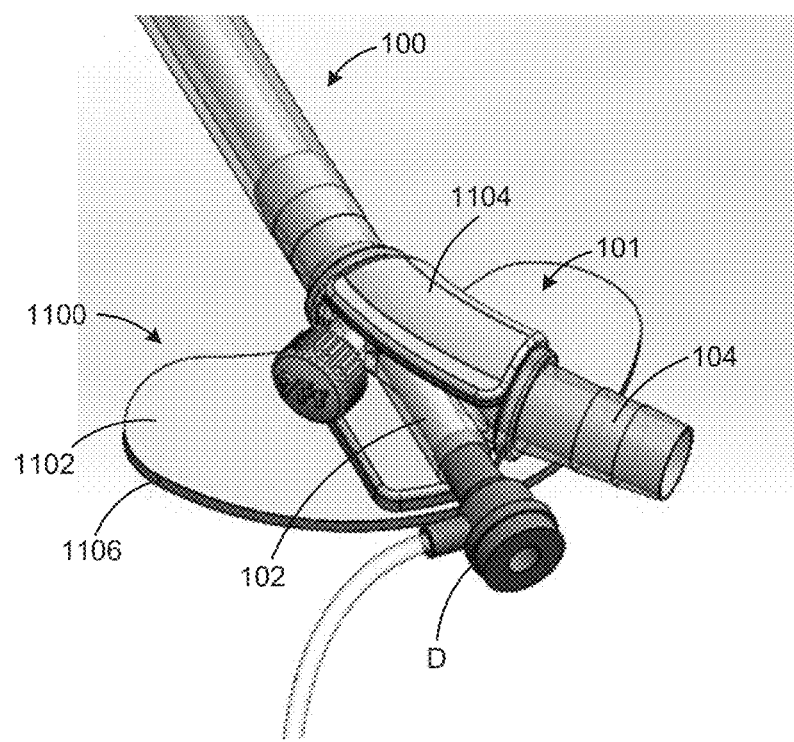
FIG. 11 illustrates an alternative exemplary fixation pad having an adhesive surface for coupling the combination device to a patient.

Referring now to FIG. 11, an alternative exemplary fixation pad is provided. Fixation pad 1100 may be constructed similar to fixation pad 1000. For example, fixation pad 1100 may include pad 1102 sized and shaped to be fixed to the patient's skin. In addition, fixation pad 1100 may include one or more hooks 1104 configured to receive at least a portion of combination device 100, e.g., connector hub 101, therein to secure combination device 100 to fixation pad 1100, and accordingly to the patient's skin. As shown in FIG. 11, the bottom surface of pad 1102 may include adhesive 1106 configured to adhere fixation pad 1100 to the patient's skin.

Figure 12A:
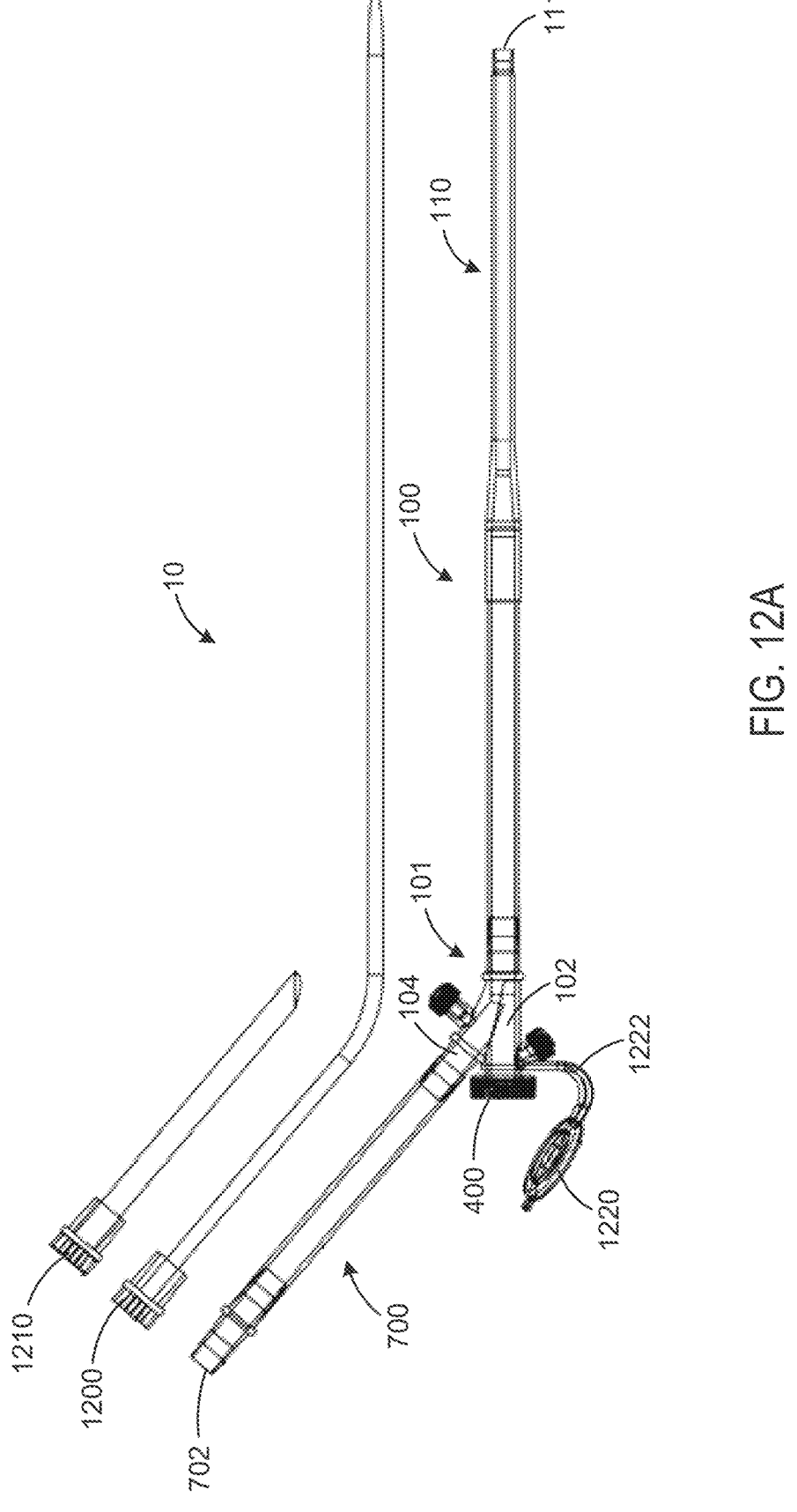
FIG. 12A illustrates an alternative exemplary hybrid system having a removable hemostatic cap for sealing a hemostatic valve of the combination device.

Referring now to FIGS. 12A to 12E, sheath and cannula combination device 100 having integrated sidearm extender 700, as described above, is provided. As shown in FIG. 12A, system 10 further may include hemostatic valve cap 1220 configured to be removably coupled to hemostatic valve 400 to seal hemostatic valve 400, e.g., when combination device 100 is not in the sheath mode, sidearm delivery cap 1200 for releasably sealing sidearm extender 700, e.g., during insertion of the distal region of elongated shaft 110 into the patient, and sidearm extender cap 1210 for releasably sealing integrated sidearm extender 700, and accordingly sidearm 104, e.g., when combination device 100 is not in the cannula mode. For example, hemostatic valve cap 1220 may be removably coupled to collinear port 102 via lanyard 1222, as shown in FIG. 12A. As will be understood by a person having ordinary skill in the art, hemostatic valve cap 1220 may be used with a combination device as described herein without an integrated sidearm extender.

Figures 12B, 12C:
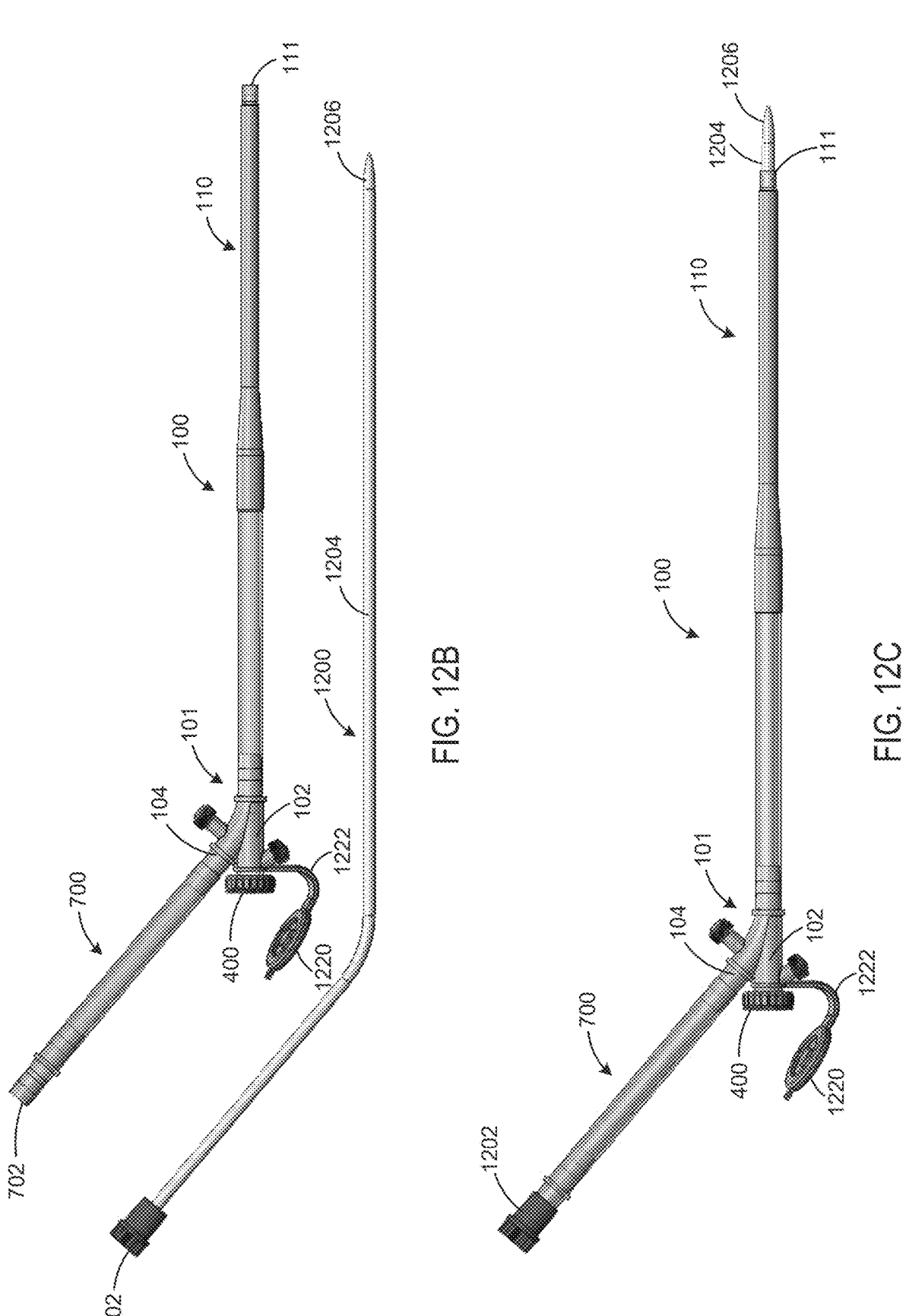
FIG. 12B illustrates an exemplary sidearm delivery obturator cap of the hybrid system of FIG. 12A.
FIG. 12C illustrates the sidearm delivery obturator cap coupled to the combination device of FIG. 12A.
Figure 12D:
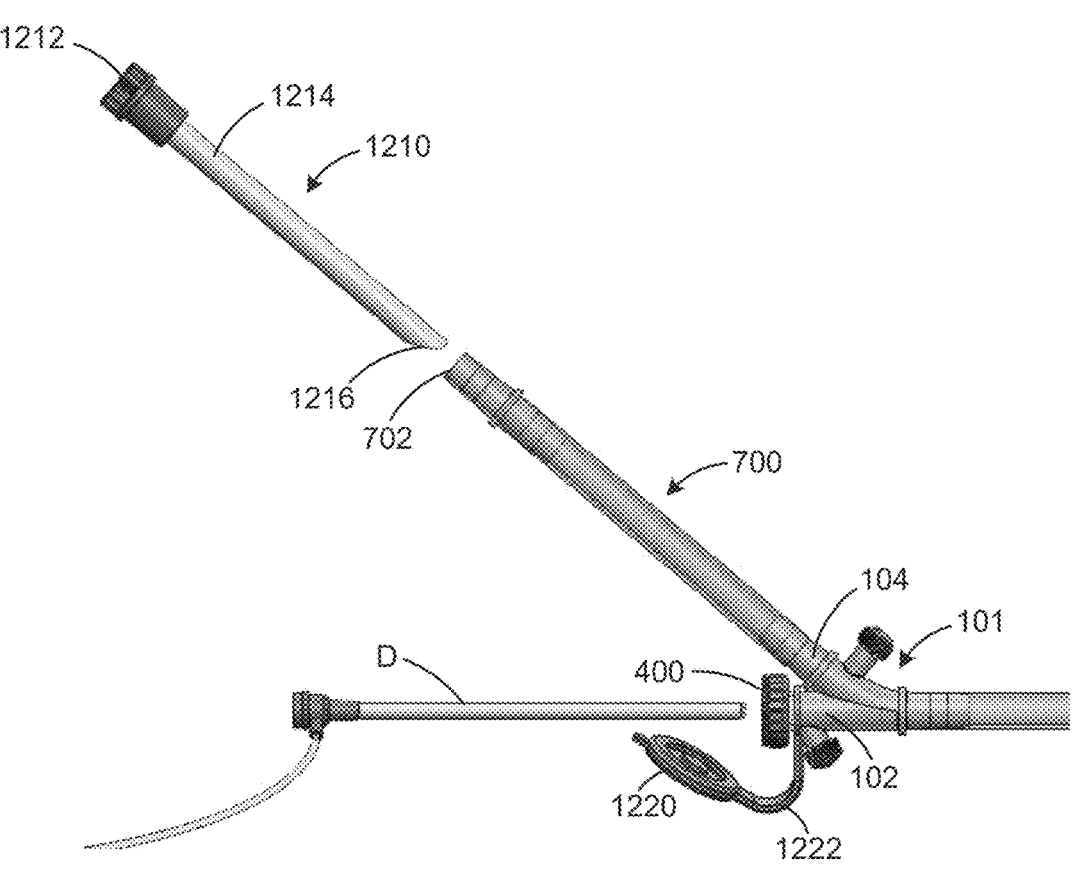
FIG. 12D illustrates an exemplary sidearm obturator cap of the hybrid system of FIG. 12A.

Sidearm extender delivery cap 1200 may be constructed similar to collinear port delivery cap 200. For example, as shown in FIG. 12D, sidearm extender delivery cap 1200 may include cap portion 1202 configured to be removably coupled to inlet 702 of sidearm extender 700 to seal sidearm extender 700, e.g., during insertion of the distal region of elongated shaft 110 into the patient, obturator 1204 sized and shaped to be disposed within the lumen of sidearm extender 700, sidearm 104, and at least the distal region of elongated shaft 110, and having a length such that a distal end of obturator 1204 extends beyond outlet 111 of elongated shaft 110, as shown in FIG. 12C, thereby providing additional stiffness to elongated shaft 110 as elongated shaft 110 is inserted into the patient's vasculature, and atraumatic tip 1206 configured to facilitate insertion of elongated shaft 110 into the patient's vasculature while minimizing/preventing injury to the patient's vasculature.

Figure 12E:
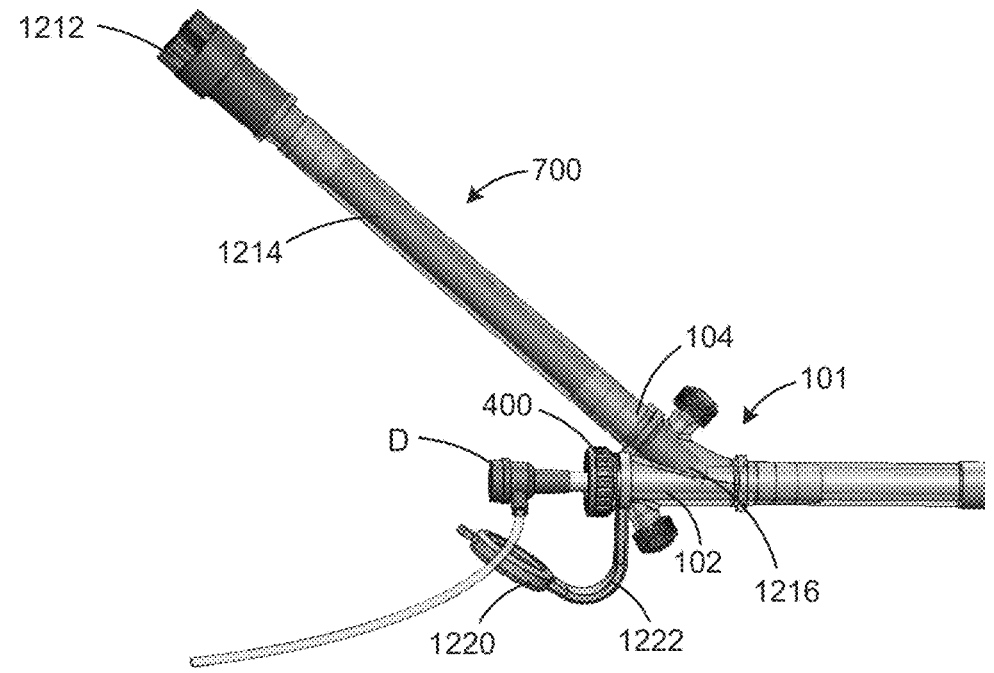
FIG. 12E illustrates the sidearm obturator cap coupled to the combination device of FIG. 12A.

Sidearm extender cap 1210 may be constructed similar to sidearm cap 310. For example, as shown in FIG. 12D, sidearm extender cap 1210 may include cap portion 1212 configured to be removably coupled to inlet 702 of sidearm extender 700 to seal sidearm extender 700, e.g., when combination device 100 is not in the cannula mode, obturator 1214 sized and shaped to be disposed within the lumen of integrated sidearm extender 700 and sidearm 104 to thereby prevent pooling of blood within sidearm extender 700 and sidearm 104, e.g., during the sheath mode, and beveled distal end 1216 having a beveled geometry corresponding to a geometry of the lumen of elongated shaft 110, e.g., a curved profile configured to align with and define the inner surface of the lumen of elongated shaft 110 when obturator 1214 is disposed within the lumen of sidearm extender 700 and sidearm 104. Like sidearm cap 310, sidearm extender cap 1210 may be configured to be coupled to inlet 702 of sidearm extender 700 in a manner that automatically aligns beveled distal end 1216 with the lumen of elongated shaft 110. In addition, obturator 1214 may have a length such that obturator 1214 extends through the lumen of sidearm extender 700 and sidearm 104, and distal end 1216 of obturator 1214 aligns with and does not obstruct the lumen of elongated shaft 110, as shown in FIG. 12E. As shown in FIG. 12E, interventional medical device D may be inserted through hemostatic valve 400 to perform an interventional medical procedure in the sheath mode while sidearm extender cap 1210 is coupled to integrated sidearm extender 700.

Figure 12F:
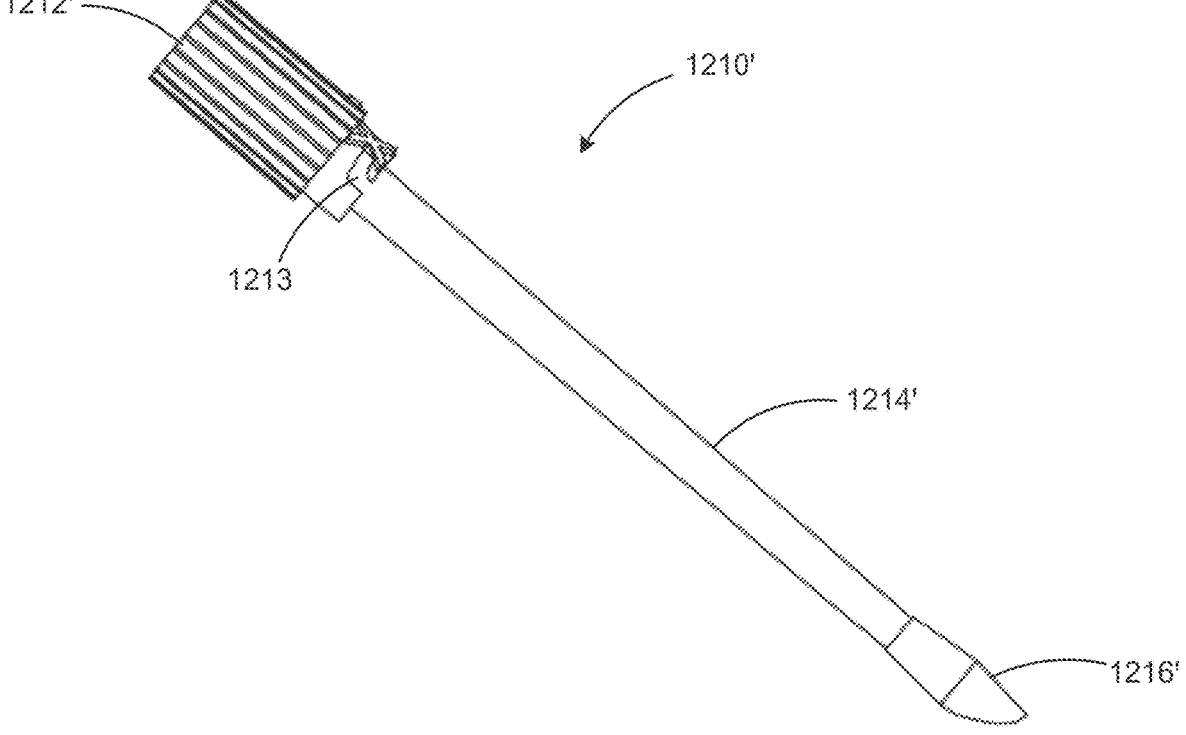
FIG. 12F illustrates an alternative exemplary sidearm obturator cap of the hybrid system.

Referring now to FIG. 12F, an alternative exemplary sidearm extender cap is provided. Sidearm extender cap 1210' may be constructed similar to sidearm extender cap 1210, with similar components having like-prime reference numerals. For example, cap portion 1212', obturator 1214', and beveled distal end 1216' correspond with cap portion 1212, obturator 1214, and beveled distal end 1216. Sidearm extender cap 1210' differs from sidearm extender cap 1210 in that beveled distal end 1216' may be formed of a bio-compatible elastomer such as silicone or thermoplastic elastomer (TPE), which may be coupled to the distal end of obturator 1214', e.g., disposed on or around the distal end of obturator 1214'. For example, beveled distal end 1216' may be molded on to or adhesively bonded to obturator 1214'. In addition, as shown in FIG. 12F, at least a portion of beveled distal end 1216', e.g., a middle portion, may have an outer diameter that is larger than the outer diameter of obturator 1214', to thereby form a fluid tight seal with the sidearm and prevent back-bleeding into the sidearm extender.

Moreover, like sidearm extender cap 1210, sidearm extender cap 1210' may be configured to be coupled to the inlet of the sidearm extender, e.g., sidearm extender 810, in a manner that automatically aligns beveled distal end 1216' with the lumen of the elongated shaft. For example, as shown in FIG. 12F, cap portion 1212' may include channel 1213 sized and shaped to receive a corresponding notch on the outer surface of the sidearm extender, e.g., notch 818 of sidearm extender 810, when obturator 1214' is disposed within the lumen of the sidearm extender to thereby automatically align beveled distal end 1216' with the lumen of the elongated shaft such that flow is not disrupted through the elongated shaft. As will be understood by a person having ordinary skill in the art, the beveled distal ends of any of the obturator removable caps/plugs described herein may be formed of a biocompatible elastomer such as silicone or TPE, and any of the obturator removable caps/plugs further may include a groove configured to receive a corresponding notch to thereby automatically align the beveled distal end with the lumen of the elongated shaft.

Figures 13A, 13B, 13C:
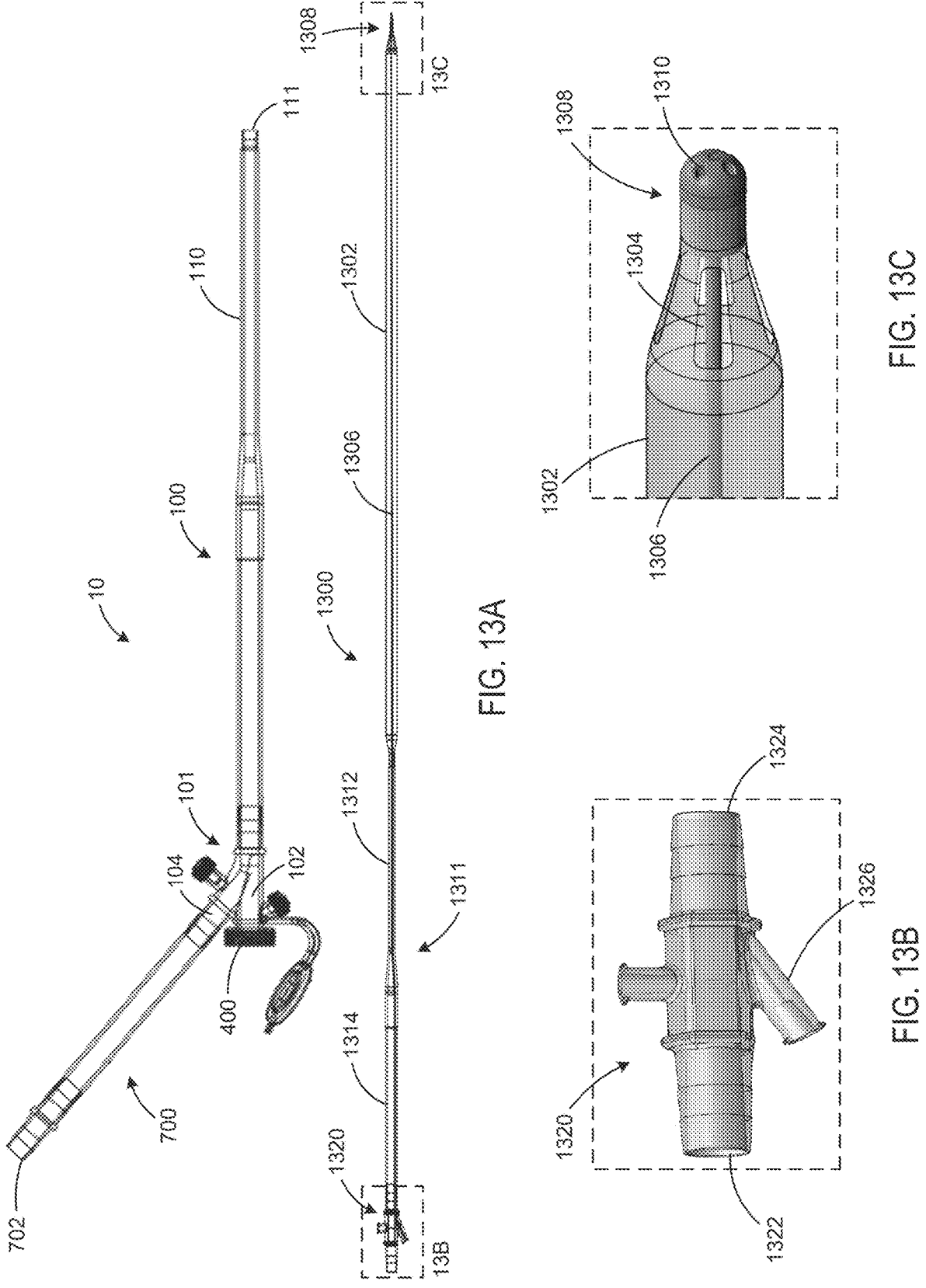
FIG. 13A illustrates an exemplary expandable ECMO extension cannula for use with the combination device of FIG. 1A in accordance with some embodiments.
FIG. 13B illustrates an exemplary connector of the expandable ECMO extension cannula of FIG. 13A.
FIG. 13C illustrates an exemplary distal region of the expandable ECMO extension cannula of FIG. 13A in accordance with some embodiments.

Referring now to FIGS. 13A to 13D, an exemplary expandable ECMO extension cannula for use with combination device 100 is provided. As shown in FIG. 13A, system 10 further may include expandable ECMO extension cannula 1300 configured to improve systemic perfusion and reduce complications during, e.g., venous-arterial extracorporeal membrane oxygenation (VA-ECMO), by delivering oxygenated blood directly to the abdominal or thoracic aorta. Extension cannula 1300 may be constructed as described in WO 2023/220724 A1 and U.S. Pat. Nos. 11,547,786 and 11,738,131 to Kapur, the entire contents of each of which is incorporated herein by reference. For example, extension cannula 1300 may include return cannula 1311 having distal portion 1312 configured for inserted within the patient's vascular and proximal portion 1314 that remains external to the patient, connector 1320 at the proximal region of return cannula 1311, expandable conduit 1302 coupled to and extending distally from the distal region of return cannula 1311, and elongated shaft 1306, e.g., a hypotube, coupled to tip 1308 at the distal region of extension cannula 1300 and extending proximally to connector 1320 at the proximal region of extension cannula 1300.

The proximal end of expandable conduit 1302 may be coupled to the distal region of return cannula 1311, e.g., to the inner surface of distal portion 1312 of return cannula 1311, via a coupling mechanism, e.g., an adhesive, heat sealing, 2-part polyurethane adhesive, and/or segmented polyurethane bonding. Accordingly, expandable conduit 1302 and distal portion 1312 of return cannula 1311 may be advanced together through combination device 100 and into the patient, e.g., by guiding tip 1308 of extension cannula 1300 via hypotube 1306, to position the outlet of expandable conduit 1302 in the vicinity of the aortic root, as described in further detail below. Alternatively, in some embodiments, the expandable conduit of extension cannula 1300 may include a self-expanding support structure, e.g., an anchoring stent such as a mesh, weave or braid formed of a shape-memory metal or stainless steel, at its proximal end such that the anchoring stent may transition from a collapsed insertion state and an expanded deployed state within the lumen of the conventional ECMO reperfusion cannula to thereby anchor the expandable conduit within the conventional ECMO reperfusion cannula, as described in WO 2023/220724 A1.

Expandable conduit 1302 is made of a soft flexible material, such as polyethylene, polyurethane, or nylon, and may include a lumen, an inlet at its proximal end, and an outlet, e.g., one or more outlet vents and/or pores, at its distal region that permit blood to perfuse through the material as the flow is directed through the lumen of expandable conduit 1302. The outlet of expandable conduit 1302 may be sized and shaped such that, as blood flows from the ECMO machine and through return cannula 1311 and the lumen of expandable conduit 1302, the blood flow exits expandable conduit 1302 via the outlet, while causing expandable conduit 1302 to fill with blood and transition from a collapsed delivery state to the expanded deployed state. Moreover, expandable conduit 1302 has a length sufficient to extend from the outlet of return cannula 1311 to a position above the patient's renal arteries, and more preferably, into the thoracic aorta, e.g., 15-120 cm, or preferably 20-80 cm or 30-50 cm. Notably, the lightweight sock-like structure provides advantages including, for example, case of deployment through tortuous or diseased aortas, as well as no impingement on the spinal cord as most patients are lying flat such that use of a rigid cannula may impinge on the spinal cord.

Hypotube 1306 is formed of a material, e.g., stainless steel rod, having sufficient rigidity to permit extension cannula 1300 to be advanced through hemostatic valve 400 of combination device 100 and through elongated shaft 110 so that the distal region of expandable conduit 1302 may be disposed with its outlet, e.g., outlet vents 1304, extending beyond a patient's renal arteries, and preferably extending in a patient's ascending aorta or in the vicinity of the aortic arch. For example, hypotube 1306 may have a lumen sized and shaped to receive a guidewire therethrough, such that extension cannula 1300 may be advanced through combination device 100 to the target location over a guidewire via the lumen of hypotube 1306. For example, hypotube 1306 may be sized and shaped to receive a guidewire having a size ranging between 0.018" to 0.038". In some embodiments, hypotube 1306 may include an anti-thrombolytic coating. Hypotube 1306 does not form part of the blood flow path through the lumen of expandable conduit 1302.

As shown in FIG. 13B, connector 1320 may have inlet 1322 configured to be coupled to an outlet of a conventional ECMO machine for receiving oxygenated blood from an ECMO circuit, sidearm 1326 extending at an angle from a side of connector 1320, and outlet 1324 configured to be coupled to, or integrally formed with, the proximal end of return cannula 1311. Inlet 1322 is in fluid communication with outlet 1324, and may optionally include a hemostatic valve. The fluid pathway extending between inlet 1322 and outlet 1324 thus permits oxygenated blood received from an ECMO circuit to flow to through the conventional ECMO cannula and expandable conduit 1302. As shown in FIG. 13B, inlet 1322 may be co-linear with outlet 1324. Moreover, sidearm 1326 is in fluid communication with the lumen of hypotube 1306, and also may have an optional hemostatic valve welded therein. Accordingly, sidearm 1326 may have a lumen sized and shaped to receive a guidewire therethrough. In addition, sidearm 1326 and hypotube 1306 may be sized and shaped to receive a stylet therein, the stylet configured to be inserted through sidearm 1326 and hypotube 1306 to preserve the lumens of sidearm 1326 and hypotube 1306 during operation and prevent clotting therein. Accordingly, the proximal end of the stylet may be configured to releasably engage with sidearm 1326 when the stylet is disposed therethrough, to thereby secure the stylet within sidearm 1326, e.g., via a threaded engagement. Additionally, upon removal of the stylet, the guidewire may be reinserted through sidearm 1326 and hypotube 1306 for removal of extension cannula 1300. In addition to a guidewire/stylet lumen, sidearm 1326 and hypotube 1306 may have another separate lumen extending therethrough, sized and shaped to receive electrical wires for measuring pressure, flow, and/or oxygen levels for blood sampling to quantify metabolites such as circulating lactate levels of inflammatory markers. In some embodiments, sidearm 1326 may be connected to a fluid filled monitor for pressure sensing.

As shown in FIG. 13C, the distal end of hypotube 1306 may include atraumatic tip 1308, which may be coupled to the distal region of expandable conduit 1302 via a connection structure, e.g., one or more umbrella-like struts, as described in WO 2023/220724 A1, such that hypotube 1306 extends proximally from tip 1308, e.g., along a central longitudinal axis of expandable conduit 1302. The distal region of expandable conduit 1302 may include one or more outflow vents 1304 disposed on at least the tapered portion of expandable conduit 1302, e.g., the portion of expandable conduit 1302 where its cross-sectional area decreases in the distal direction towards tip 1308, and sized and shaped to permit blood flow therethrough, e.g., from within the lumen of expandable conduit 1302 and into the patient's vasculature. As shown in FIG. 13C, outflow vents 1304 may be arranged circumferentially around the tapered portion of expandable conduit 1302, and extend longitudinally along the tapered portion having a slit-like geometry. As will be understood by a person having ordinary skill in the art, although FIG. 13C shows outflow vents 1304 having a trapezoidal/rectangular shape, outflow vents 1304 may have other longitudinally extending shapes, e.g., ovals, rectangles, triangles, etc. Preferably, the width of outflow vents 1304 increases in the proximal direction from tip 1308 to improve flow therethrough.

In addition, extension cannula 1300 may include one or more holes 1310 extending through tip 1308, and sized and shaped to permit blood flow therethrough, e.g., from within the lumen of expandable conduit 1302 and into the patient's vasculature. For example, holes 1310 may be formed by drilling through tip 1308. By permitting blood flow through holes 1310, flow may be maintained, and stasis removed from that region, thereby preventing and/or reducing clot formation within the distal end of expandable conduit 1302, e.g., between the distal end of outflow vents 1304 and the interior surface of tip 1308. As described above, expandable conduit 1302 may include a plurality of pores (not shown) disposed on at least the distal region of expandable conduit 1302, the pores sized and shaped to permit blood flow therethrough to thereby avoid blood stasis or clotting along the length of the cannula and to more evenly distribute flow in the aorta, thereby also avoiding loading of the left ventricle. The pores may be disposed on the distal region of expandable conduit 1302 proximal to outflow vents 1304 and/or on the tapered portion, e.g., between adjacent outflow vents 1304.

Figure 13D:
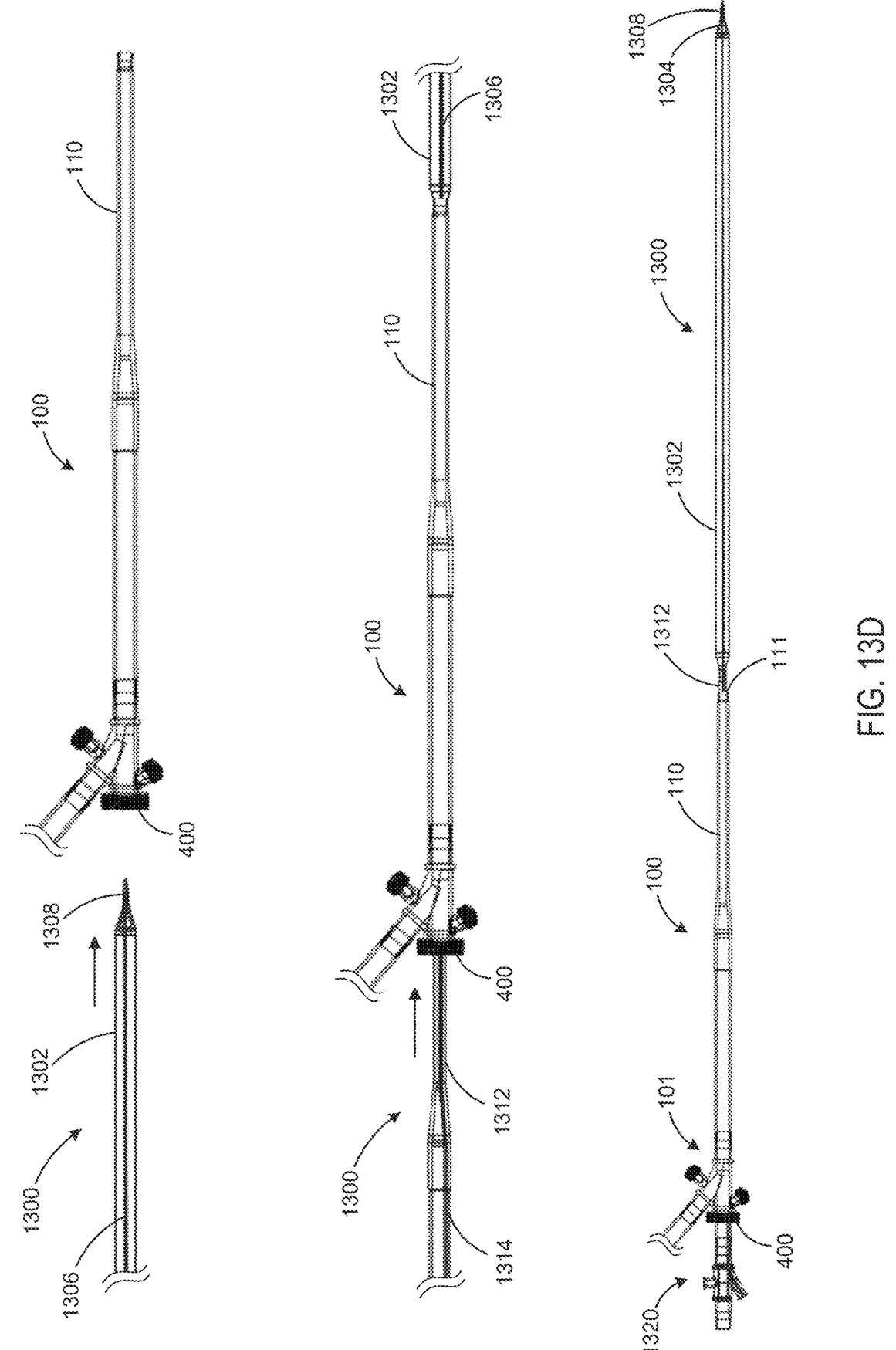
FIG. 13D illustrates insertion of the expandable ECMO extension cannula of FIG. 13A within the combination device.

FIG. 13D illustrates insertion of extension cannula 1300 through combination device 100, e.g., to thereby position outlet vents 1304 of expandable conduit 1302 in the vicinity of the aortic root while outlet 111 is disposed within the patient's vasculature below the renal vessels. For example, tip 1308 of extension cannula 1300 may be guided through hemostatic valve 400 of combination device 100 via hypotube 1306, e.g., over a guidewire preinserted through combination device 100, and through the lumen of elongated shaft 110 and out outlet 111 of elongated shaft 110 such that distal portion 1312 of return cannula 1311 is disposed at least partially within the distal region of elongated shaft 110, e.g., within the patient's vasculature, and outlet vents 1304 are disposed in the vicinity of the aortic root. In some embodiments, combination device 100 may be used to drain blood out of the patient's vasculature, e.g., out of the aorta, via outlet 111 and into an ECMO circuit, which then directs blood from the ECMO circuit into inlet 1322 of extension cannula 1300 and out outflow vents 1304 directly to the abdominal or thoracic aorta. Accordingly, combination device 100 and extension cannula 1300 together may be used to both receive and deliver flow from an ECMO circuit without requiring a separate venous drainage cannula.

Figures 14A, 14B, 14C:
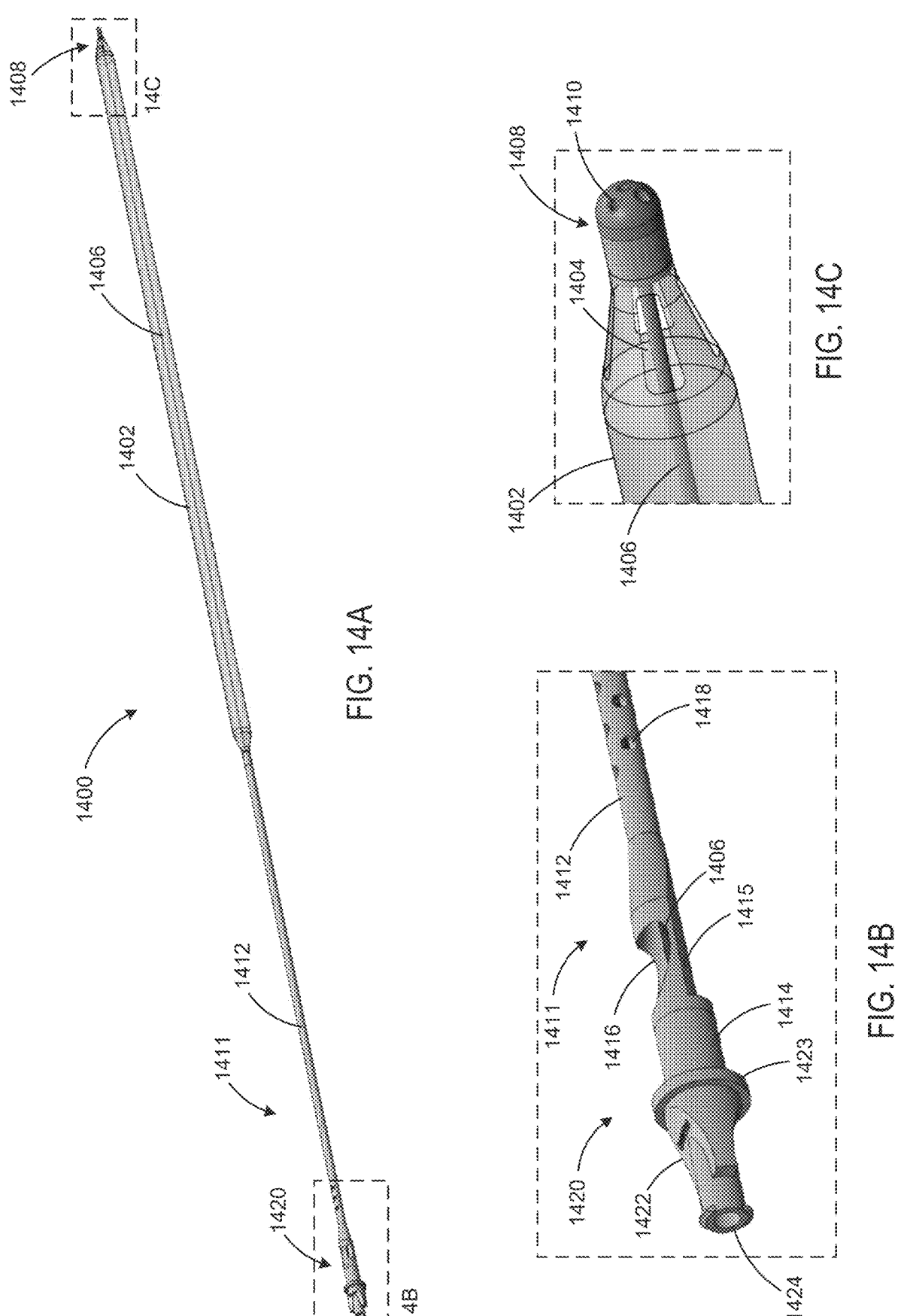
FIG. 14A illustrates an alternative exemplary expandable ECMO extension cannula for use with the combination device of FIG. 1A in accordance with some embodiments.
FIG. 14B illustrates an exemplary proximal region of the expandable ECMO extension cannula of FIG. 14A.
FIG. 14C illustrates an exemplary distal region of the expandable ECMO extension cannula of FIG. 14A in accordance with some embodiments.

Referring now to FIGS. 14A to 14C, another exemplary expandable ECMO extension cannula for use with combination device 100 is provided. Extension cannula 1400 may be constructed similar to extension cannula 1300. For example, extension cannula 1400 may include return cannula 1411, expandable conduit 1402 coupled to and extending distally from the distal region of return cannula 1411, and elongated shaft 1406, e.g., a hypotube, coupled to tip 1408 at the distal region of extension cannula 1400 and extending proximally to the proximal region of return cannula 1411. Extension cannula 1400 differs from extension cannula 1300 in that instead of connector 1320, extension cannula 1400 comprises proximal region 1420 configured to receive oxygenated blood from an ECMO circuit via sidearm 104 of combination device 100, as described in further detail below with regard to FIG. 14B. In addition, return cannula 1411 includes distal portion 1412 having an outer diameter that is smaller than the lumen extending through elongated shaft 110 of combination device 100, e.g., smaller than the lumen extending through both the distal portion of elongated shaft 110 that is inserted within the patient's vasculature and the proximal portion of elongated shaft 110 that remains external to the patient, and proximal portion 1414 (FIG. 14B) having an outer diameter that is substantially equal to the inner diameter of the portion of the lumen extending through the proximal portion of elongated shaft 110 of combination device 100. For example, distal portion 1412 may have a diameter between 10 Fr and 24 Fr. Accordingly, when extension cannula 1400 is completely inserted within combination device 100, a space is formed within the lumen of elongated shaft 110 between the outer surface of distal portion 1412 of return cannula 1411 and the inner surface of elongated shaft 110, and proximal portion 1414 is fitted within the lumen of elongated shaft 110 adjacent to hemostatic valve 400 to thereby prevent pooling of blood therein.

As shown in FIG. 14B, a proximal region of return cannula 1411 may include inlet 1416 extending laterally along an outer surface of return cannula 1411 and configured to be aligned with the outlet of sidearm 104 of combination device 100 when extension cannula 1400 is completely inserted within combination device 100 to fluidically couple the lumen of sidearm 104 with the lumen of return cannula 1411 extending from inlet 1416 through distal portion 1412 to the outlet of distal portion 1412. Accordingly, when inlet 1416 is aligned with the outlet of sidearm 104, a continuation of the blood flow path from sidearm 104 is formed at least partially through return cannula 1411 and expandable conduit 1402 and out the outlet of expandable conduit 1402, e.g., at the distal region of expandable conduit 1402. As shown in FIG. 14B, inlet 1416 may be disposed between proximal portion 1414 and distal portion 1412 of return cannula 1411. The outer surface of return cannula 1411 where inlet 1416 is formed may be parallel and coincident to the outer surface of proximal portion 1414 such that it engages the inner surface of elongated shaft 110 when inlet 1416 is aligned with the outlet of sidearm 104 to thereby direct blood flow received from sidearm 104 only through inlet 1416.

As shown in FIG. 14B, the lateral side of return cannula 1411 opposite to inlet 1416 may include gap 1415, such that the outer surface of return cannula 1411 defining gap 1415 is spaced apart from and does not contact the inner surface of elongated shaft 110. For example, the outer surface of return cannula 1411 defining gap 1415 may be parallel and coincident with the outer surface of distal portion 1412 of return cannula 1411. Accordingly, the outer surface of return cannula 1411 defining gap 1415 may extend from the distal end of proximal portion 1414 across the portion of return cannula 1411 comprising inlet 1416 and across the transition zone from the portion of return cannula 1411 comprising inlet 1416 to distal portion 1412, e.g., the portion of return cannula 1411 where the cross-sectional area decreases. The outer surface of return cannula 1411 defining gap 1415 may be flat, as shown in FIG. 14B, or alternatively, curved, or some combination thereof. Accordingly, upon rotation of extension cannula 1400 relative to combination device 100, e.g., via handle portion 1422, the degree of alignment between inlet 1416 and the outlet of sidearm 104 may be adjusted, such that at least a portion of blood flow received from sidearm 104 will be directed through the portion of inlet 1416 that is aligned with the outlet of sidearm 104, and at least a portion of blood flow received from sidearm 104 will be directed into gap 1415 and the space defined by the outer surface of distal portion 1412 of return cannula 1411 and the inner surface of elongated shaft 110, as described in further detail below with regard to FIGS. 15H and 15I.

Referring again to FIG. 14B, at least a proximal region of distal portion 1412 of return cannula 1411 may include a plurality of openings 1418 extending through the wall of distal portion 1412, such that blood flow is permitted between the lumen of distal portion 1412 and the space defined by the outer surface of distal portion 1412 of return cannula 1411 and the inner surface of elongated shaft 110 through openings 1418, e.g., to maintain cannula patency when combination device 1400 is oriented to direct a majority of blood flow to expandable conduit 1402. The plurality of openings 1418 may be distributed laterally and/or circumferentially along distal portion 1412, e.g., in a symmetric manner, to promote steady and consistent blood flow through the space between the outer surface of distal portion 1412 and the inner surface of elongated shaft 110 and out outlet 111 of elongated shaft 110. Alternatively, in some embodiments, return cannula 1411 may not include any openings 1418, such that blood only flows through the space between the outer surface of distal portion 1412 and the inner surface of elongated shaft 110 when extension cannula 1400 is rotated relative to combination device 100 to fluidically couple the sidearm 104 and gap 1415, as described above.

Moreover, as shown in FIG. 14B, hypotube 1406 may extend from distal tip 1408 proximally through the lumen of return cannula 1411 such that hypotube 1406 is in fluid communication with opening 1424 at the proximal end of extension cannula 1400. Accordingly, opening 1424 may be sized and shaped to receive a guidewire therethrough. In some embodiments, opening 1424 and hypotube 1406 may be sized and shaped to receive a stylet therein, the stylet configured to be inserted through opening 1424 and hypotube 1406 to preserve the lumen of hypotube 1406 during operation and prevent clotting therein. In addition, extension cannula 1400 may include a stop, e.g., lip 1423 extending radially outward from a longitudinal axis of extension cannula 1400, and disposed between handle portion 1422 and proximal portion 1414 of return cannula 1411. Lip 1423 may be sized and shaped such that it is too large to be inserted through hemostatic valve 400 to thereby prevent further advancement of extension cannula 1400 into combination device 100. In addition, opening 1424 may be configured to releasably receive a cap, e.g., cap 1430 shown in FIG. 15D below. For example, the proximal end region of extension cannula 1400 may include a lumen sized and shaped to releasably receive a protrusion of cap 1430, e.g., via an interference fit. Alternatively, the proximal end region of extension cannula 1400 may include an engagement mechanism for releasably engaging with cap 1430, e.g., a threaded engagement.

Expandable conduit 1402 may be constructed similar to expandable conduit 1302. For example, as shown in FIG.

14C, the distal end of hypotube 1406 may include atraumatic tip 1408, which may be coupled to the distal region of expandable conduit 1402, such that hypotube 1406 extends proximally from tip 1408, e.g., along a central longitudinal axis of expandable conduit 1402. In addition, extension cannula 1400 may include one or more holes 1410 extending through tip 1408, and sized and shaped to permit blood flow therethrough, such that flow may be maintained, and stasis removed from that region, thereby preventing and/or reducing clot formation within the distal end of expandable conduit 1402. Moreover, expandable conduit 1402 may include a plurality of pores (not shown) disposed on at least the distal region of expandable conduit 1402, and sized and shaped to permit blood flow therethrough to thereby avoid blood stasis or clotting along the length of the cannula and to more evenly distribute blood flow. As blood flows from the ECMO machine through return cannula 1411 and the lumen of expandable conduit 1402 and out the outlet of expandable conduit 1402, the blood flow causes expandable conduit 1402 to fill with blood and transition from a collapsed delivery state to the expanded deployed state. In its expanded state, expandable conduit 1402 may have a diameter between 14 Fr and 40 Fr. Moreover, expandable conduit 1402 has a length sufficient to extend from the return cannula 1411 to a position above the patient's renal arteries, and more preferably, into the abdominal or thoracic aorta, e.g., 10-120 cm, or preferably 10-60 cm.

Figures 15A, 15B, 15C, 15D:
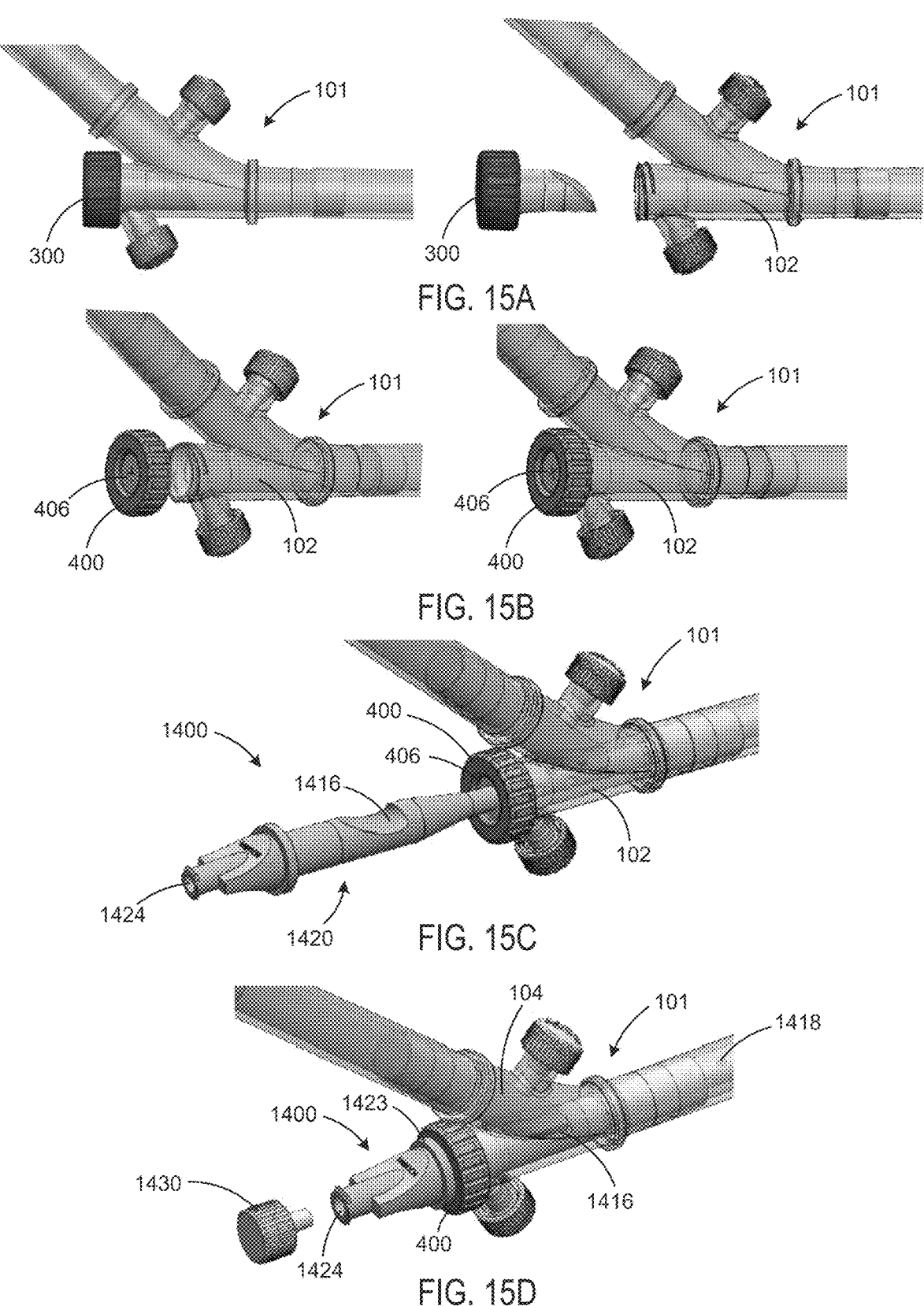
FIGS. 15A to 15D illustrate insertion of the expandable ECMO extension cannula of FIG. 14A within the combination device.

Referring now to FIGS. 15A to 15I, insertion of extension cannula 1400 into combination device 100 and blood flow therethrough is provided. As shown in FIGS. 15A and 15B, collinear port cap 300 may first be removed from collinear port 102 of connector hub 101 of combination device 100, and hemostatic valve 400 having hemostatic valve membrane 406 may be removably coupled to collinear port 102. A guidewire may be inserted through hemostatic valve membrane 406 of hemostatic valve 400, through the lumen of elongated shaft 110, and out outlet 111 of elongated shaft 110 to the target location, e.g., the aortic root. Extension cannula 1400 may then be inserted into combination device 100 by advancing distal tip 1408, followed by expandable conduit 1402 and return cannula 1411, through hemostatic valve membrane 406 of hemostatic valve 400 and into the lumen of elongated shaft 110, e.g., via hypotube 1406 over the guidewire, as shown in FIGS. 15C and 15D. As shown in FIG. 15D, when extension cannula 1400 is completely inserted within combination device 100, e.g., when lip 1423 abuts hemostatic valve 400, the guidewire may be removed from hypotube 1406, and cap 1430 may be removably inserted into opening 1424. Extension cannula 1400 may be rotated relative to combination device 100, e.g., by rotating handle portion 1422, to ensure that the desirable degree of alignment between the outlet of sidearm 104 and inlet 1416 is achieved. Handle portion 1422 may be sized and shaped and/or include markings to facilitate complete alignment of the outlet of sidearm 104 and inlet 1416.

Figure 15E:
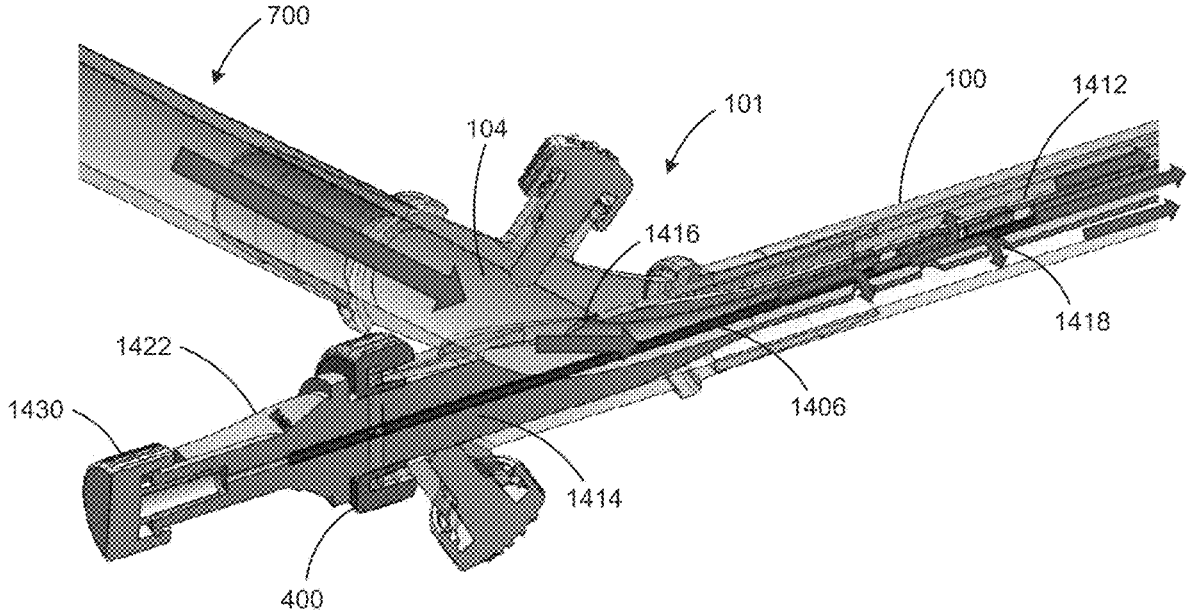
FIGS. 15E to 15G illustrate blood flow through the combination device with the expandable ECMO extension cannula of FIG. 14A coupled thereto in accordance with some embodiments.
Figure 15F:
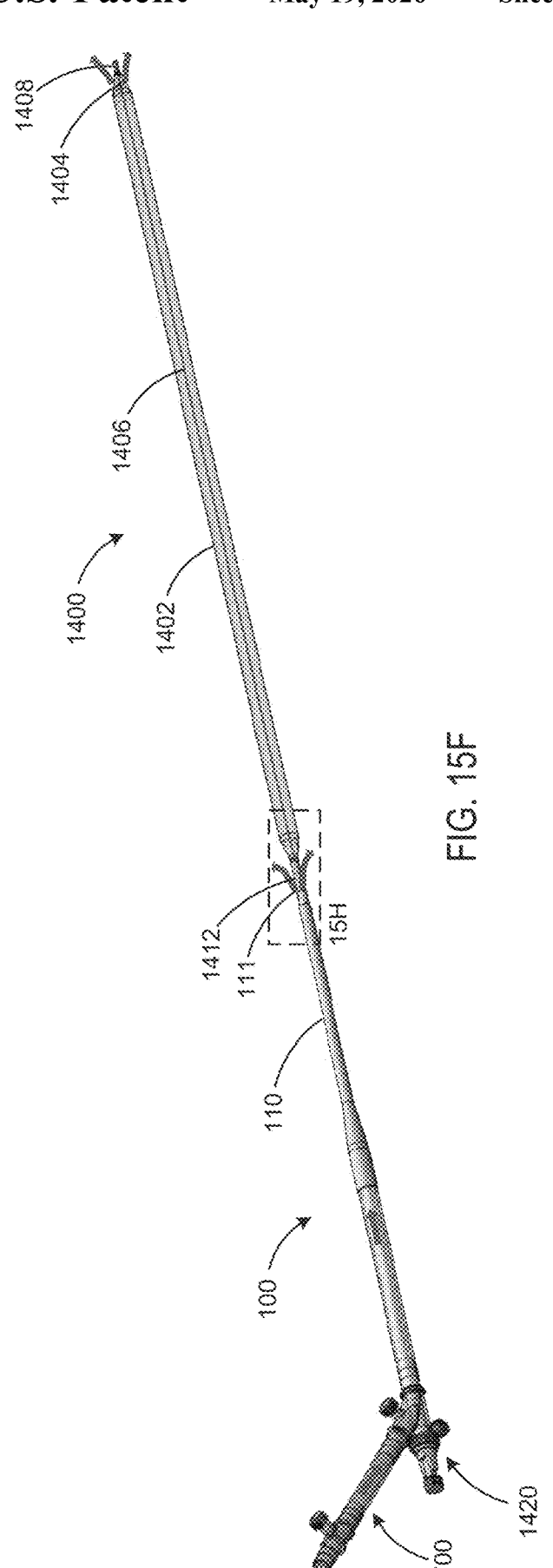
Figure 15G:
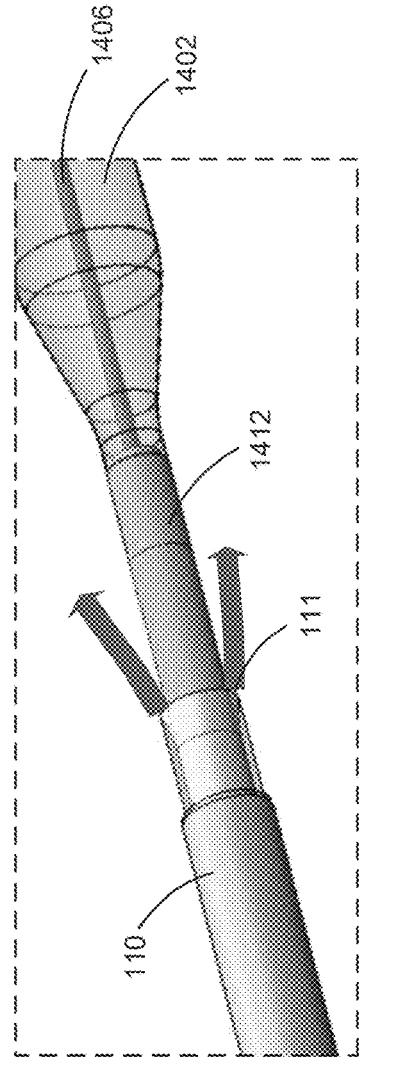

FIGS. 15E to 15G illustrate blood flow through combination device 100 and extension cannula 1400 when the outlet of sidearm 104 and inlet 1416 are completely aligned, such that blood flow through sidearm 104, e.g., via optional sidearm extender 700 coupled to the inlet of sidearm 104, is only directed through inlet 1416 of return cannula 1411 and into the lumen of return cannula 1411. As shown in FIG. 15E, proximal portion 1414 fills the space within the lumen of elongated shaft 110 proximal to inlet 1416, to thereby prevent pooling of blood therein. As described above, blood is permitted to flow into the space between the outer surface of distal portion 1412 and the inner surface of elongated shaft 110 via openings 1418. Accordingly, a portion of the blood received from sidearm 104 may flow out of outlet vents 1404 at the distal region of expandable conduit 1402, e.g., for distal perfusion above the patient's renal vessels, and the remaining portion of the blood received from sidearm 104 may flow out of outlet 111 of elongated shaft 110 of combination device 100, e.g., for systemic perfusion, in the cannula mode, as shown in FIG. 15F. As shown in FIG. 15G, return cannula 1411 may have a length such that at least a portion of the distal region of distal portion 1412 of return cannula 1411 extends distally beyond outlet 111 of elongated shaft 110 when extension cannula 1400 is completely inserted within combination device 100 to ensure blood is able to flow out outlet 111, e.g., outlet 111 is not blocked by expandable conduit 1402 expanded against the distal edge of outlet 111. For example, distal portion 1412 may have a length between 10 cm and 60 cm.

Figure 15H:
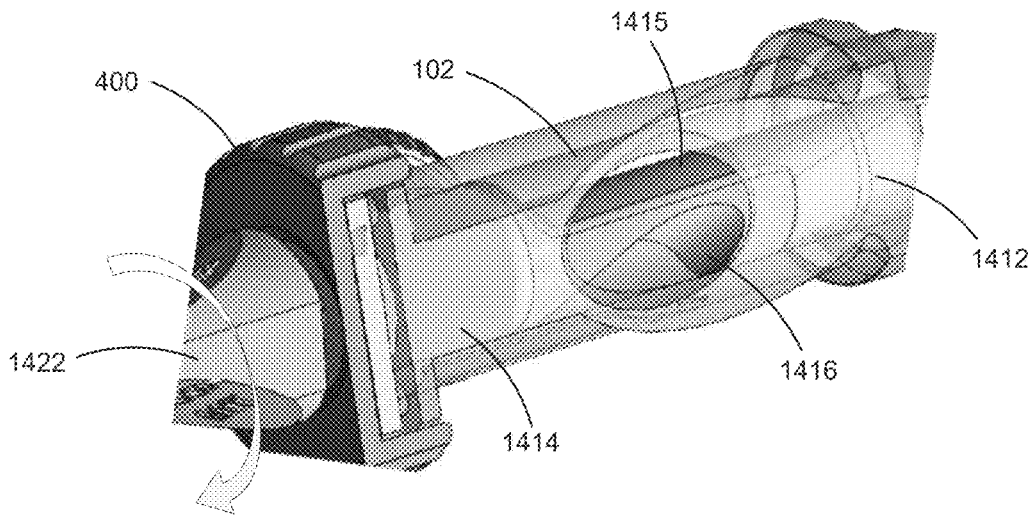
FIGS. 15H and 15I illustrate rotation of the expandable ECMO extension cannula of FIG. 14A within the combination device to adjust blood flow through the combination device in accordance with some embodiments.
Figure 15I:
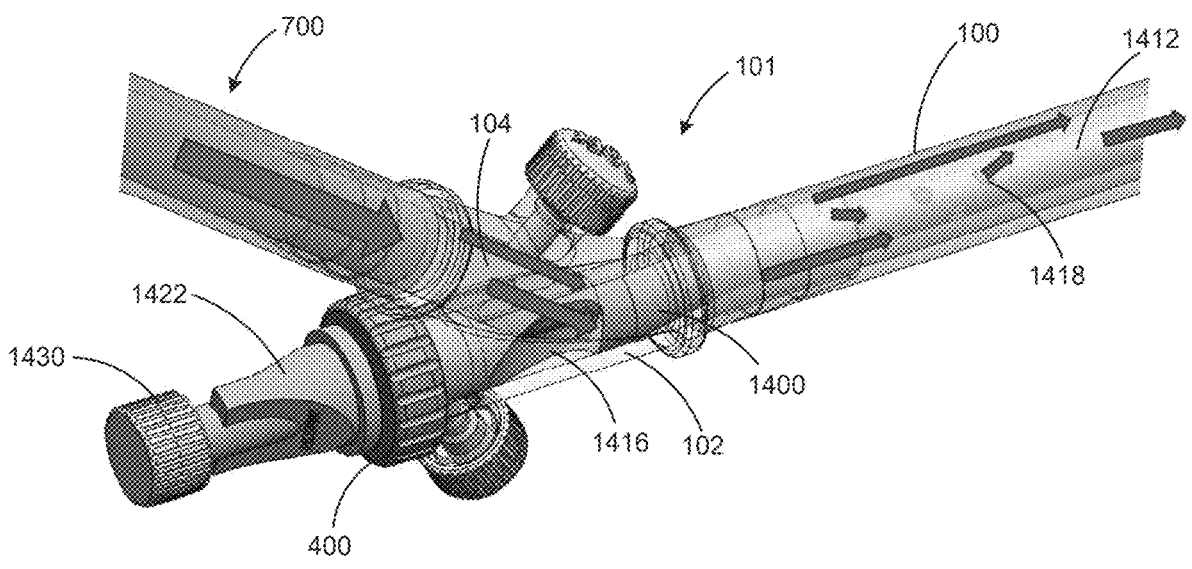

As described above, the amount of blood flow received from sidearm 104 and directed into the lumen of return cannula 1411 via inlet 1416 may be selectively adjusted by rotating extension cannula 1400, e.g., via handle portion 1422, relative to combination device 100 to vary the degree of alignment between the outlet of sidearm 104 and inlet 1416, as shown in FIG. 15H. Accordingly, as the degree of alignment between the outlet of sidearm 104 and inlet 1416 decreases via rotation of extension cannula 1400 relative to combination device 100, the degree of alignment between the outlet of sidearm 104 and gap 1415 increases, such that at least a portion of blood flow received from sidearm 104 will be directed into gap 1415, as shown in FIG. 15I.

Figures 16A, 16B:
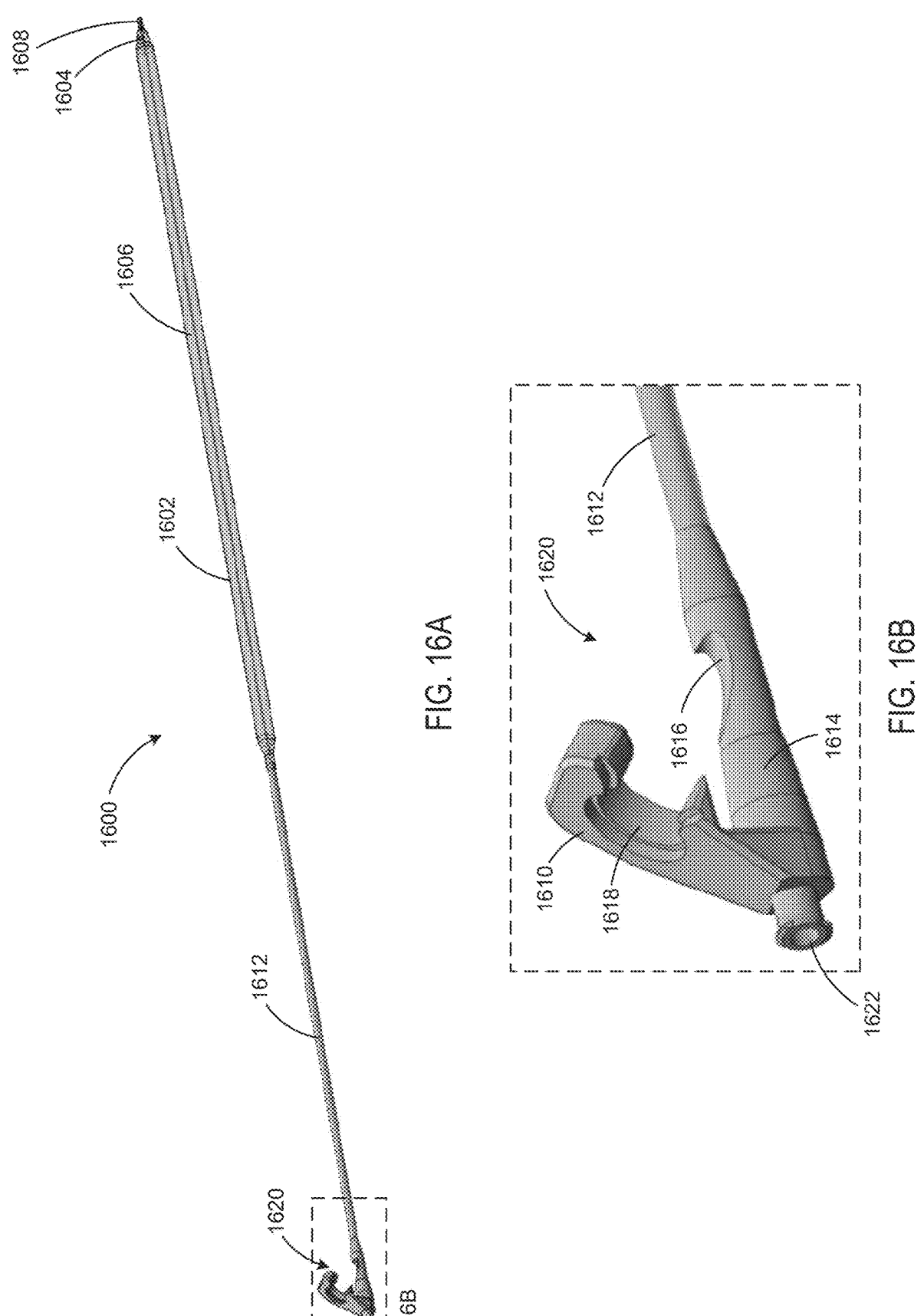
FIG. 16A illustrates another alternative exemplary expandable ECMO extension cannula for use with the combination device of FIG. 1A in accordance with some embodiments.
FIG. 16B illustrates an exemplary proximal region of the expandable ECMO extension cannula of FIG. 16A.

Referring now to FIGS. 16A to 16F, another exemplary expandable ECMO extension cannula for use with combination device 100 is provided. Extension cannula 1600 may be constructed similar to extension cannula 1400. For example, return cannula 1611 having distal portion 1612, proximal portion 1614, and inlet 1616, expandable conduit 1602 coupled to and extending distally from distal portion 1612 and having outlet vents 1604 at its distal region, distal tip 1608 coupled to the distal ends of expandable conduit 1602 and hypotube 1606 extending proximal towards proximal region 1620 of return cannula 1611, and opening 1622 in fluid communication with hypotube 1606 of extendable cannula 1600 correspond with return cannula 1411, expandable conduit 1402, distal tip 1408, hypotube 1406, and opening 1422 of extension cannula 1400. Extendable cannula 1600 differs from extendable cannula 1400 in that proximal region 1620 may include clamping arm 1610 coupled to, or integrally formed with, extendable cannula 1600. As shown in FIG. 16B, clamping arm 1610 may include receiving channel 1618 sized and shaped to releasably engage sidearm 104 of combination device 100 in a manner that automatically aligns inlet 1616 of return cannula 1611 with the outlet of sidearm 104. Thus, clamping arm 1610 may extend radially outward from the longitudinal axis of extendable cannula 1600 at angle such that sidearm 104 may be releasably received within receiving channel 1618 of clamping arm 1610 when extension cannula 1600 is completely inserted within combination device 100.

Figures 16C, 16D, 16E:
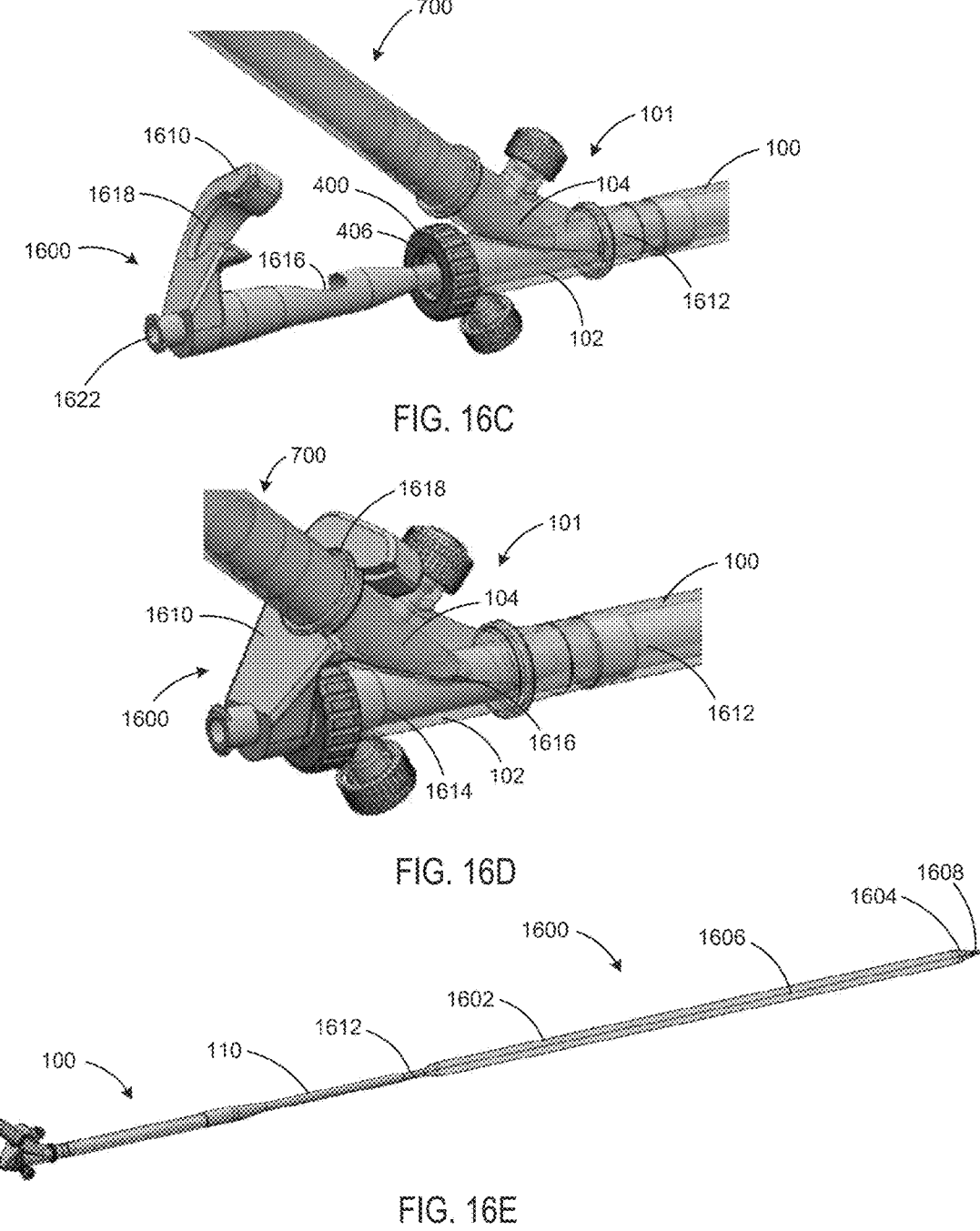
FIGS. 16C to 16E illustrate insertion of the expandable ECMO extension cannula of FIG. 16A within the combination device.
Figure 16F:
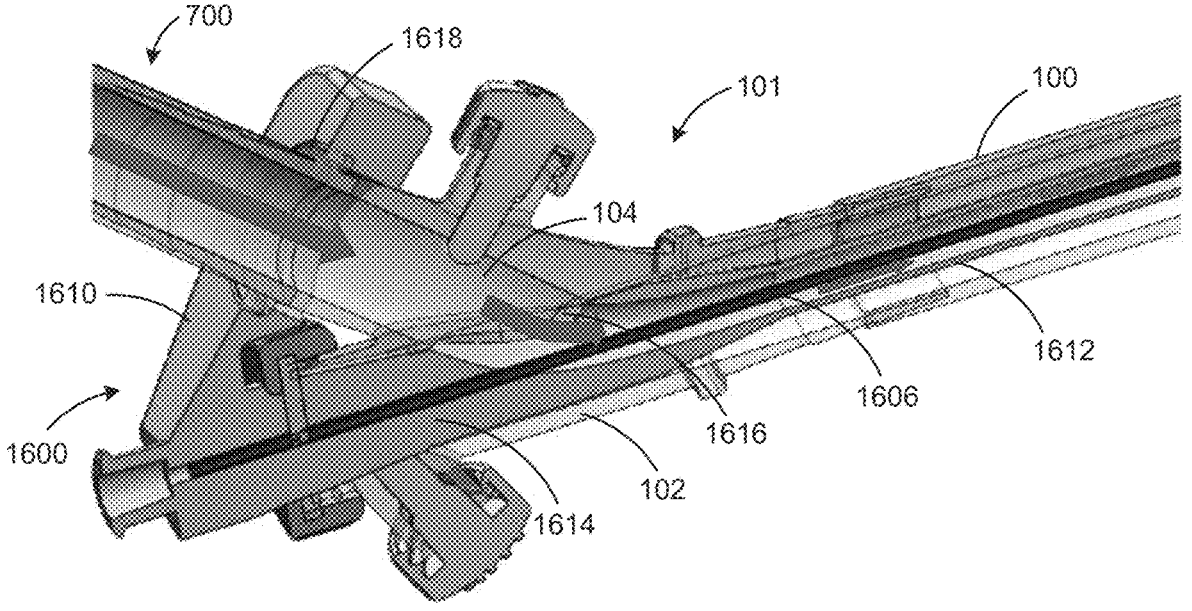
FIG. 16F illustrates blood flow through the combination device with the expandable ECMO extension cannula of FIG. 16A coupled thereto in accordance with some embodiments.

For example, FIG. 16C illustrates insertion of extension cannula 1600 into combination device 100. As shown in FIG. 16C, extension cannula 1600 may be inserted through hemostatic valve membrane 406 of hemostatic valve 400 and into the lumen of elongated shaft 110, e.g., via hypotube 1606 over the guidewire, in an orientation such that clamping arm 1610 is clear from sidearm 104, and/or optionally sidearm extender 700, as extension cannula 1600 is inserted into combination device 100. When extension cannula 1600 is completely inserted within combination device 100, clamping arm 1610 may be rotated to rotate extension cannula 1600 relative to combination device 100 until sidearm 104 is releasably received within receiving channel 1618 of clamping arm 1610, and accordingly, inlet 1616 is completely aligned with the outlet of sidearm 104, as shown in FIG. 16D. FIG. 16E illustrates extension cannula 1600 completely inserted within combination device 100, with sidearm 104 releasably received within receiving channel 1618 of clamping arm 1610, and FIG. 16F illustrates the blood flow path from sidearm 104 through inlet 1616 and into the lumen of return cannula 1611. In some embodiments, at least a proximal region of distal portion 1612 of return cannula 1611 may include a plurality of openings sized and shaped to permit blood flow between the lumen of return cannula 1611 and the space defined by the outer surface of distal portion 1612 of return cannula 1611 and the inner surface of elongated shaft 110, such that at least a portion of the blood flow received from sidearm 104 may flow through the openings into the space between the outer surface of distal portion 1612 and the inner surface of elongated shaft 110 and out outlet 111 of elongated shaft 110 of combination device 100.

Moreover, in some embodiments, like extension cannula 1400, the outer surface of return cannula 1611 may define a gap opposite from inlet 1616 that is spaced apart from and does not contact the inner surface of elongated shaft 110 when extension cannula 1600 is inserted into combination device 100, such that extension cannula 1600 may be selectively rotated relative to combination device 100 to adjust the amount of blood flow directed into the lumen of return cannula 1611, and accordingly, expandable conduit 1602, and the amount of blood flow directed into the gap, and accordingly, the space between the outer surface of distal portion 1612 and the inner surface of elongated shaft 110. Accordingly, in this embodiment, clamping arm 1610 may be rotatably coupled to the proximal end of extendable cannula 1600, such that extension cannula 1600 may be selectively rotated relative to combination device 100 while sidearm 104 is received within receiving channel 1618 of clamping arm 1610.

Figures 17A, 17B:
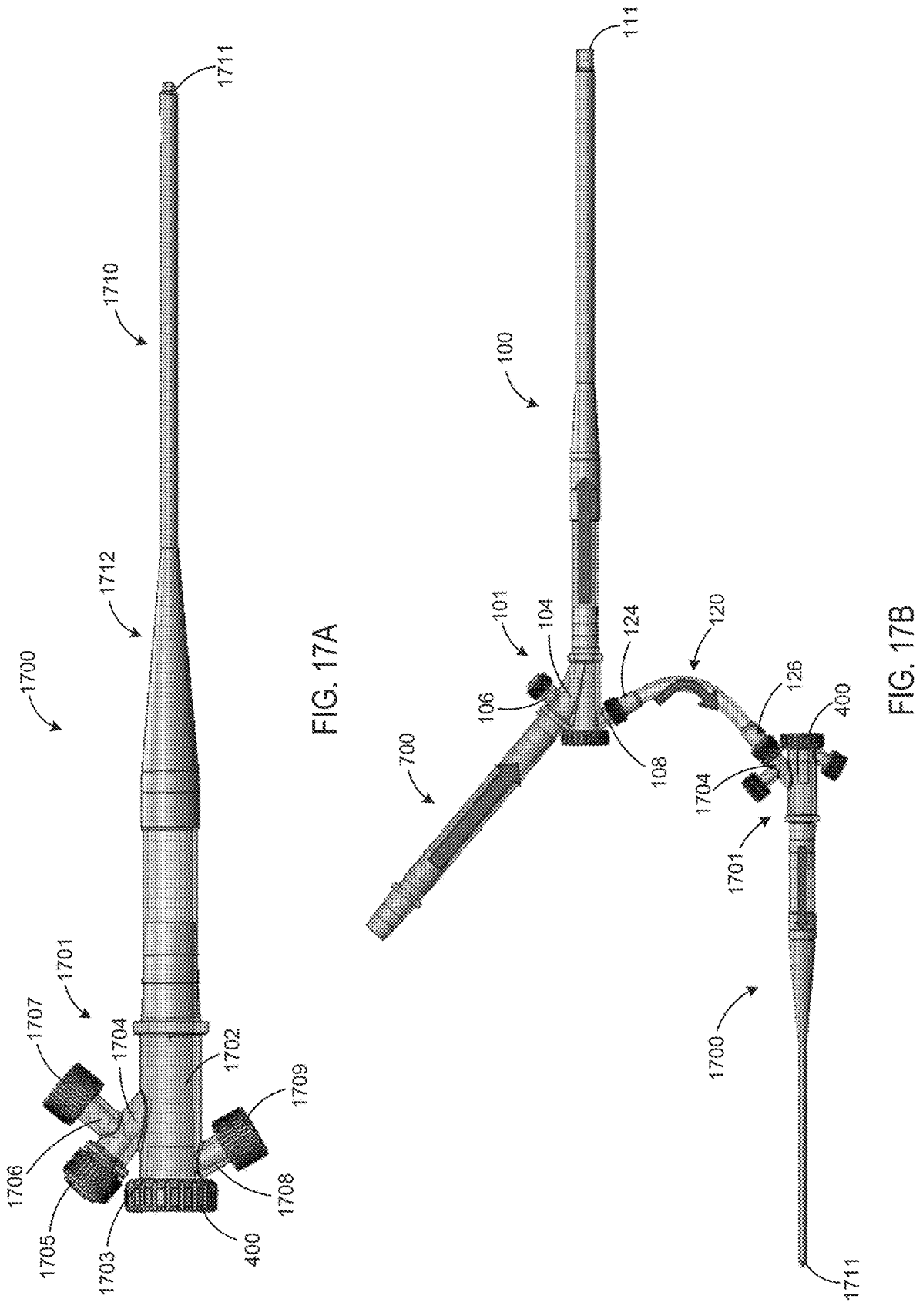
FIG. 17A illustrates an exemplary distal perfusion sheath and cannula combination device with an angled sidearm to direct blood flow and a collinear port to enable a medical procedure.
FIG. 17B illustrates blood flow through the combination device of FIG. 1A with the distal perfusion sheath and cannula combination device of FIG. 17A coupled thereto for systemic and distal perfusion in accordance with some embodiments.

Referring now to FIGS. 17A and 17B, an exemplary distal perfusion sheath and cannula combination device configured for perfusion of a patient's distal extremities is provided. Distal perfusion sheath and cannula combination device 1700 may be constructed similar to sheath and cannula combination device 100. For example, elongated shaft 1710 having outlet 1711 and transition region 1712 where the cross-sectional area of elongated shaft 1710 decreases from the proximal region to the distal region configured to be inserted into a patient's vasculature, and connector hub 1701 having collinear port 1702 having inlet 1703 configured to receive the interventional medical device therethrough, sidearm 1704 angled relative to the longitudinal axis of elongated shaft 1710 and fluidically coupled to elongated shaft 1710, first port 1708, e.g., a Luer port, fluidically coupled to the proximal region of elongated shaft 1710 and angled towards inlet 1703 of collinear port 1702 to permit fluid flow therethrough to washout stasis regions of blood within collinear port 1702, and second port 1706, e.g., a Luer port, fluidically coupled to sidearm 1702, of combination device 1700 corresponds to elongated shaft 110 and connector hub 101 of combination device 100. Accordingly, like combination device 100, combination device 1700 further may include various caps, plugs, and optionally obturators, as described herein, configured to be removably coupled to the inlets of combination device 1700, e.g., inlet 1703 of collinear port 1702, inlet 1705 of sidearm 1704, inlet 1709 of first port 1708, and inlet 1707 of second port 1706, as shown in FIG. 17A.

Combination device 1700 differs from combination device 100 in that the distal region of elongated shaft 1710 is sized and shaped to be inserted within an artery supplying blood to a distal limb of the patient, e.g., having a size between 4 Fr and 10 Fr, or preferably between 4 Fr and 8 Fr, and sidearm 1704 comprises a Luer connector having a size between 8 Fr and 14 Fr, or preferably between 8 Fr and 12 Fr, e.g., 10 Fr. Moreover, the distal region of elongated shaft 1710 configured for insertion into the patient's vasculature, e.g., the artery supplying blood to a distal limb of the patient, may have an overall shorter length, e.g., 4 to 8 cm, than the distal region of elongated shaft 110 configured for insertion into the patient's vasculature, e.g., the femoral artery. Combination device 1700 may be used as a standalone device for perfusion of the patient's distal extremities, e.g., via a connector tubing fluidically coupling sidearm 1704 to any arterial sheath or any other pump system beyond ECMO, or in conjunction with combination device 100, e.g., to provide distal perfusion of the patient's distal extremities while combination device 100 provides systemic perfusion.

For example, placement of combination device 100 within the patient's femoral artery for systemic perfusion may occlude the femoral artery, thereby occluding blood flow to the patient's distal extremities, which may lead to distal limb ischemia. Thus, by inserting combination device 100 into the patient's vasculature such that outlet 1711 is disposed within an artery supplying blood to a distal limb of the patient, and fluidically coupling combination device 100 to combination device 1700, e.g., via tubing 120 having first connector 124 removably and fluidically coupled to first port 108 and second connector 126 removably and fluidically coupled to sidearm 1704, as shown in FIG. 17B, at least a portion of oxygenated blood flow received by combination device 100 via sidearm 104, and optionally sidearm extender 700, will be redirected through first port 108 into tubing 120 and through sidearm 1704 into combination device 1700 for distal perfusion of the patient's distal extremities via outlet 1711, while at least a portion of the oxygenated blood flow received by combination device 100 via sidearm 104 is directed through combination device 100 for systemic perfusion of the patient's femoral artery via outlet 111. As will be understood by a person having ordinary skill in the art, first connector 124 may alternatively be removably and fluidically coupled to second port 106 to redirect at least a portion of oxygenated blood from sidearm 104 to sidearm 1704 of combination device 1700 via tubing 120. For example, when an interventional medical device such as an extension cannula, e.g., extension cannula 1300, 1400, 1600, is inserted through collinear port 102 into elongated shaft 110 of combination device 100, thereby blocking blood flow through first port 108, first connector 124 may be connected to second port 106.

When used as a standalone device without combination device 100, sidearm 1704 of combination device 1700 may be independently connected directly to an external pump, e.g., a centrifugal flow pump such as ECMO, a roller pump, or an axial flow pump, to displace blood from a donor sheath/cannula through the external pump and into sidearm 1704.

Moreover, like combination device 100, inlet 1703 of combination device 1700 may be removably coupled to a hemostatic valve, e.g., hemostatic valve 400, to thereby permit insertion of an interventional medical device therethrough and into the lumen of elongated shaft 1710 and out outlet 1711, thereby allowing diagnostic and/or interventional procedures involving the patient's lower limb such as, e.g., arteriography, thrombectomy, angioplasty, stenting, lithotripsy, rotational atherectomy, delivery of pressure, flow, or temperature sensors, blood sampling, etc., optionally during distal perfusion of the patient's distal extremities via sidearm 1704.

Figure 18:
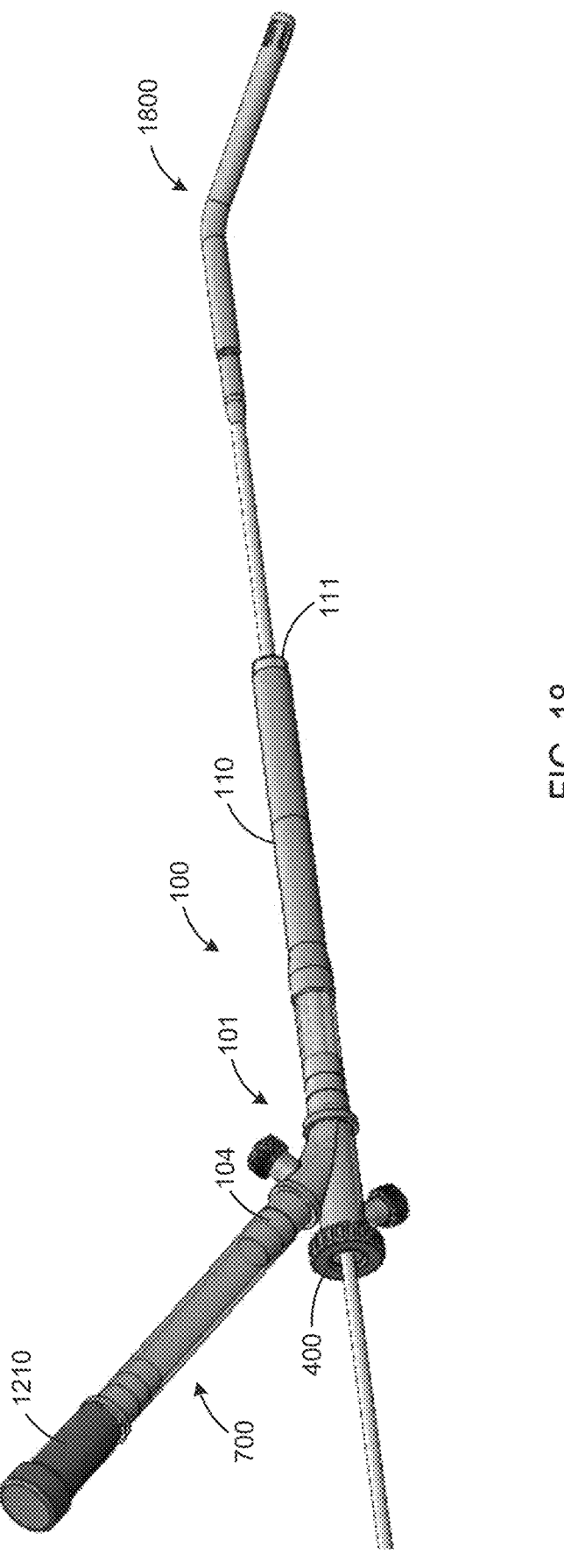
FIG. 18 illustrates the combination device of FIG. 1A with an exemplary percutaneous catheter-based heart pump device inserted therethrough in accordance with some embodiments.

Referring now to FIG. 18, combination device 100 is illustrated with heart pump device 1800, e.g., a catheter-based heart pump device, inserted therethrough. As described above, a trans-valvular rotary flow pump, e.g., an Impella® pump (made available by Abiomed, Inc. of Danvers, Massachusetts), may be inserted through and/or used in conjunction with combination device 100 to mitigate the effects of heart injury during system perfusion. Accordingly, the distal region of elongated shaft 110 may be sized and shaped to be inserted within an axillary artery of the patient for access to the patient's heart for placement of heart pump device 1800. For example, elongated shaft 110 may have a size of 32 Fr (8.6 mm inner diameter) to thereby accommodate a 21 Fr (7 mm outer diameter) Impella® pump. Combination device 100 may be sized and shaped to accommodate other percutaneous ventricular assist devices (pVADs) including, for example, pVADs made available by Supira Medical, Inc. of Los Gatos, California and/or by Magenta Medical Ltd. of Kadima, Israel.

Figure 19:
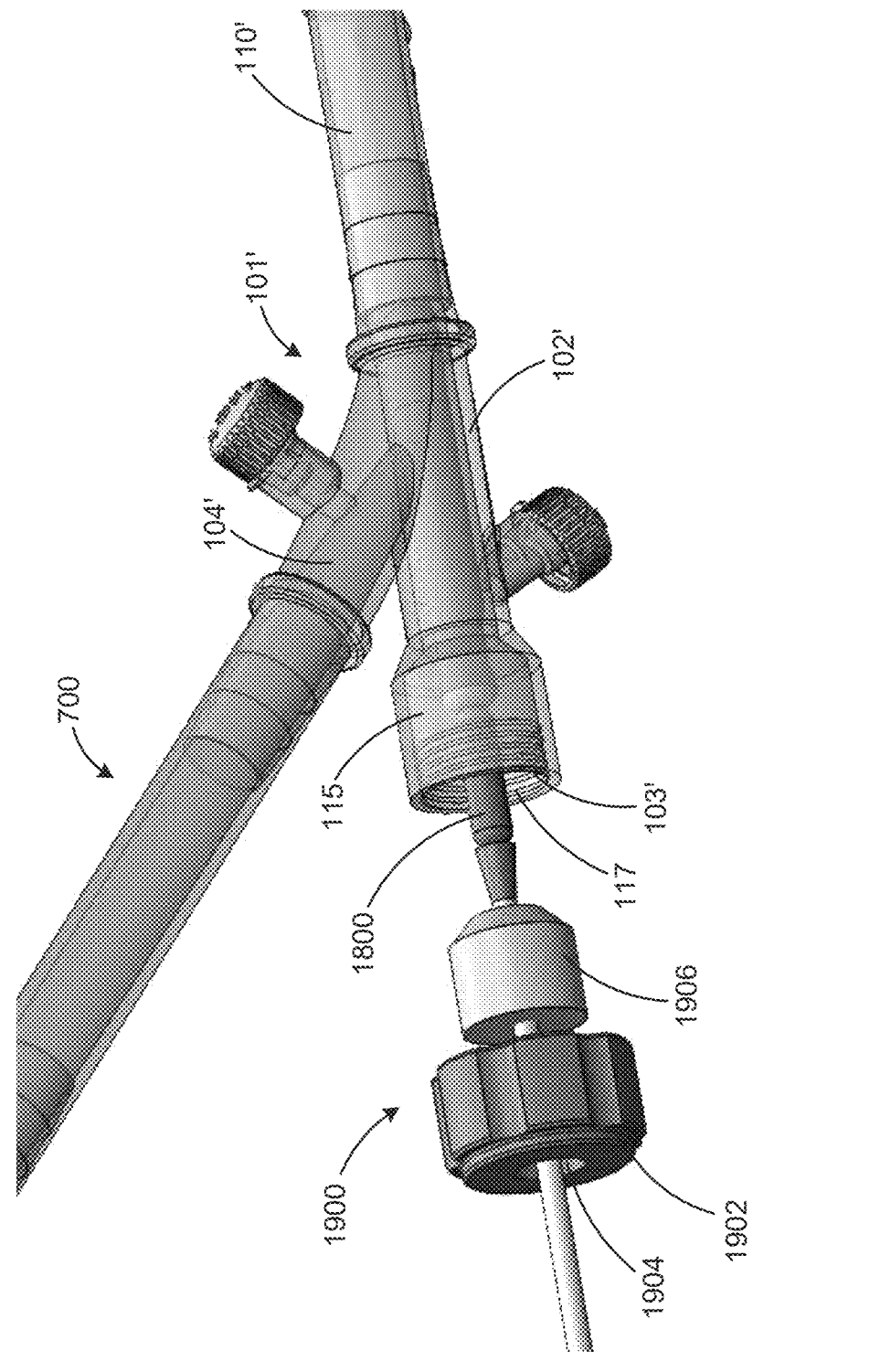
FIG. 19 illustrates an exemplary hemostatic plug for receiving a percutaneous catheter-based heart pump device for insertion into the combination device in accordance with some embodiments.

Referring now to FIG. 19, a hemostatic plug cap for preventing backflow of blood through the combination device during insertion of an interventional medical device such as a percutaneous ventricular assist device (pVAD) therein for long-term hemostasis in the sheath mode is provided. Connector hub 101' may be constructed similar to connector hub 101 of combination device 100, with similar components having like-prime reference numerals. For example, connector hub 101' includes collinear port 102' having inlet 103' in fluidic communication with elongated shaft 110', and sidearm 104' angled relative to and in fluidic communication with elongated shaft 110'. As shown in FIG. 19, collinear port 102' may include space 115 defined by inlet 103' and extending at least partially within collinear port 102', space 115 sized and shaped to sealingly receive hemostatic plug cap 1900 therein. Accordingly, space 115 is in fluidic communication with elongated shaft 110'.

Hemostatic plug cap 1900 may include cap portion 1902 configured to be removably coupled to inlet 103' of collinear port 102', e.g., via a threaded connection, and opening 1904 sized and shaped to permit insertion of a large bore interventional medical device, for example, catheter-based heart pump device 1800, e.g., a pVAD, therethrough. For example, cap portion 1902 may comprise a threaded mating surface configured to releasably engage with corresponding threaded mating surface 117 at inlet 103' of collinear port 102'. In addition, hemostatic plug cap 1900 may comprise a locking mechanism configured to stabilize the medical device therein. For example, hemostatic plug cap 1900 may be configured to house hemostatic plug 1906 sized and shaped to be sealingly receiving within space 115 of collinear port 102'. Hemostatic plug 1906 includes an opening for receiving device 1800 therethrough, which is configured to collapse onto the shaft of device 1800 when the device 1800 is inserted within the combination device to prevent backflow of blood across hemostatic plug 1906. In some embodiments, hemostatic plug 1906 may comprise a Tuohy valve. As will be understood by a person having ordinary skill in the art, any of the hemostatic caps/valves described herein may similarly include a locking mechanism configured to stabilize the medical device therein.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A sheath and cannula combination device for selectively directing blood flow and enabling an interventional medical procedure, the sheath and cannula combination device comprising:

an elongated shaft defining a longitudinal axis and comprising a distal region having a first outlet, a proximal region having a first inlet, and a first lumen extending between and fluidically coupling the first outlet and the first inlet along the longitudinal axis, the distal region configured to be in fluid communication with a patient's vasculature, the first lumen sized and shaped to permit insertion of an interventional medical device therethrough in a sheath mode for performing the interventional medical procedure;

a connector hub at the proximal region of the elongated shaft, the connector hub comprising a collinear port configured to receive the interventional medical device therethrough, a proximal end of the collinear port defining the first inlet of the elongated shaft;

a hemostatic valve configured to be removably coupled to the first inlet, the hemostatic valve comprising a locking mechanism configured to sealably receive the interventional medical device therethrough in the sheath mode;

a sidearm configured to be fluidically coupled to the first lumen at the proximal region of the elongated shaft, the sidearm angled relative to the longitudinal axis of the elongated shaft, the sidearm defining a second outlet, a second inlet, and a second lumen extending between the second inlet and the second outlet, the second lumen sized and shaped to direct the blood flow from the sidearm into the first lumen of the elongated shaft and out the first outlet in a cannula mode; and a collinear port cap configured to be removably coupled to the proximal end of the collinear port to seal the first inlet when the hemostatic valve has been removed from the first inlet, the collinear port cap comprising an obturator sized and shaped to be disposed within at least a portion of the first lumen to prevent pooling of blood within the at least the portion of the first lumen, a distal end of the obturator comprising a beveled geometry corresponding to a geometry of the second lumen of the sidearm such that the obturator does not obstruct the blood flow between the second lumen and the first lumen in the cannula mode.

2. The sheath and cannula combination device of claim 1, further comprising a first port fluidically coupled to the elongated shaft at the proximal region, the first port angled towards the collinear port to permit fluid flow therethrough to washout stasis regions of blood within the collinear port.

3. The sheath and cannula combination device of claim 2, further comprising a second port fluidically coupled to the second lumen of the sidearm, the second port configured to permit the blood flow between the second port and the second lumen.

4. The sheath and cannula combination device of claim 3, further comprising a tubing having a first end configured to be coupled to the second port, and a second end configured to be coupled to the first port, the tubing configured to redirect at least some of the blood flow from the second lumen through the tubing into the first lumen towards the collinear port to washout the stasis regions of blood within the collinear port in the cannula mode.

5. The sheath and cannula combination device of claim 3, wherein the second port is configured to be coupled to a perfusion cannula configured to redirect at least some of the blood flow from the second lumen through the perfusion cannula for perfusion of the patient's distal extremities in the cannula mode.

6. The sheath and cannula combination device of claim 2, further comprising a male-to-male connector having a first end configured to be fluidically coupled to the first port, and a second end configured to be fluidically coupled to a male end of a stopcock.

7. The sheath and cannula combination device of claim 1, wherein the second inlet of the sidearm is configured to be fluidically coupled to a cardiopulmonary bypass system.

8. The sheath and cannula combination device of claim 1, wherein the hemostatic valve comprises a cap portion comprising a threaded mating surface configured to be removably coupled to a corresponding threaded mating surface of the first inlet.

9. The sheath and cannula combination device of claim 1, wherein the hemostatic valve comprises one or more disc-shaped valve membranes.

10. The sheath and cannula combination device of claim 1, wherein the hemostatic valve comprises a duckbill valve membrane configured to seal the first inlet, a distal end of the duckbill valve membrane comprising a beveled geometry corresponding to the geometry of the second lumen such that the duckbill valve membrane does not obstruct fluid flow between the second lumen and the first lumen in the cannula mode.

11. The sheath and cannula combination device of claim 1, wherein the beveled geometry of the distal end of the obturator of the collinear port cap comprises a ramped and/or curved profile configured to facilitate smooth blood flow between the second lumen and the first lumen in the cannula mode.

12. The sheath and cannula combination device of claim 1, wherein the collinear port cap is configured to be removably coupled to the proximal end of the collinear port in a manner that auto-aligns the beveled geometry of the obturator with the second lumen of the sidearm.

13. The sheath and cannula combination device of claim 1, further comprising a sidearm cap configured to be removably coupled to a proximal end of the sidearm to seal the second inlet, the sidearm cap comprising an obturator sized and shaped to be disposed within the second lumen to prevent pooling of blood within the second lumen, a distal end of the obturator of the sidearm cap comprising a beveled geometry corresponding to a geometry of the first lumen of the elongated shaft such that the obturator of the sidearm cap does not obstruct the first lumen in the sheath mode.

14. The sheath and cannula combination device of claim 13, wherein the sidearm cap is configured to be removably coupled to the proximal end of the sidearm in a manner that auto-aligns the beveled geometry of the obturator of the sidearm cap with the first lumen of the elongated shaft.

15. The sheath and cannula combination device of claim 1, further comprising a sidearm extender having a proximal end comprising a third inlet configured to be fluidically coupled to a cardiopulmonary bypass system, a distal end comprising a third outlet configured to be fluidically coupled to the second inlet of the sidearm, and a third lumen extending between the third inlet and the third outlet, the third lumen sized and shaped to direct the blood flow from the sidearm extender through the sidearm and into the first lumen of the elongated shaft and out the first outlet in the cannula mode.

16. The sheath and cannula combination device of claim 15, wherein the sidearm extender comprises a one-way valve disposed within the third lumen.

17. The sheath and cannula combination device of claim 16, further comprising an actuator operatively coupled to the one-way valve, the actuator configured to be actuated to transition the one-way valve between an open state where the blood flow is permitted to flow through the third lumen in the cannula mode, and a closed state where the blood flow through the third lumen is prevented.

18. The sheath and cannula combination device of claim 15, wherein the sidearm extender comprises a clampable region disposed between the third inlet and the third outlet, the clampable region configured to be clamped to prevent the blood flow through the third lumen.

19. The sheath and cannula combination device of claim 1, wherein the elongated shaft comprises a connection portion at the first outlet configured to be removably coupled to an inlet of a return cannula configured to be positioned within the patient's vasculature to fluidically couple the first inlet and the second inlet and the patient's vasculature.

20. The sheath and cannula combination device of claim 1, wherein the distal region of the elongated shaft is configured to be inserted into an artery supplying blood to a distal limb of the patient, the distal region of the elongated shaft comprising a size between 4 Fr and 10 Fr, and wherein the sidearm comprises a Luer connector having a size between 8 Fr and 14 Fr.

21. The sheath and cannula combination device of claim 1, wherein the distal region of the elongated shaft is sized and shaped to be inserted into an axillary artery, and wherein the interventional medical device comprises a heart pump device such that the first lumen is sized and shaped to permit insertion of the heart pump device therethrough.

22. A system for selectively directing blood flow and enabling an interventional medical procedure, the system comprising:

the sheath and cannula combination device of claim 1, wherein the interventional medical device comprises an expandable extension cannula; and the expandable extension cannula comprising a proximal region comprising a return cannula configured to receive blood flow from an external pump, a distal region comprising a flexible conduit configured to transition between a collapsed insertion state and an expanded deployed state when in communication with the blood flow from the external pump, and a hypotube coupled to a distal end of the flexible conduit and configured to advance the flexible conduit through the collinear port of the connector hub into the first lumen of the elongated shaft and out of the first outlet of the elongated shaft, wherein the flexible conduit has a length selected so that when the first outlet of the elongated shaft is positioned at a location proximal of the patient's renal vessels, one or more outflow vents of the flexible conduit extend beyond the patient's renal vessels.

23. The system of claim 22, wherein the return cannula comprises an inlet in fluid communication with the one or more outflow vents of the flexible conduit, the inlet extending laterally along an outer surface of the return cannula and configured to be aligned with the second outlet of the sidearm to fluidically couple the sidearm and the expandable extension cannula and form a continuation of a blood flow path through the second lumen of the sidearm.

24. The system of claim 23, wherein the return cannula comprises a handle configured to selectively rotate the expandable extension cannula relative to the sheath and cannula combination device to vary a degree of alignment between the inlet of the return cannula and the second outlet of the sidearm to thereby vary an amount of the blood flow through the flexible conduit.

25. The system of claim 24, wherein the return cannula is configured such that, when the inlet of the return cannula and the second outlet of the sidearm are not completely aligned, at least a portion of the blood flow through the sidearm is directed to a space within the first lumen of the elongated shaft between the outer surface of the return cannula and an inner surface of the elongated shaft, the space in fluid communication with the first outlet of the elongated shaft.

26. The system of claim 23, wherein a distal portion of the return cannula has an outer diameter that is smaller than a diameter of the first lumen of the elongated shaft, the distal portion of the return cannula comprising one or more openings configured to fluidically couple a lumen of the return cannula with a space within the first lumen of the elongated shaft between the outer surface of the return cannula and an inner surface of the elongated shaft, the space in fluid communication with the first outlet of the elongated shaft.

27. The system of claim 23, wherein a proximal portion of the return cannula has an outer diameter that is substantially equal to a diameter of the first lumen of the elongated shaft.

28. The system of claim 23, wherein a proximal portion of the return cannula comprises a clamping arm extending radially outward at an angle relative to a longitudinal axis of the return cannula, the clamping arm comprising a receiving channel sized and shaped to releasably engage the sidearm in a manner that aligns the inlet of the return cannula with the second outlet of the sidearm.

29. A system for selectively directing blood flow and enabling an interventional medical procedure, the system comprising:

the sheath and cannula combination device of claim 1, further comprising a port fluidically coupled to the second lumen of the sidearm; and a distal perfusion sheath and cannula combination device comprising:

a second elongated shaft comprising a distal region having a third outlet, a proximal region having a third inlet collinear with the third outlet, and a third lumen extending between the third inlet and the third outlet along a longitudinal axis of the second elongated shaft, the distal region of the second elongated shaft configured to be inserted into an artery supplying blood to a distal limb of the patient, the third lumen comprising a diameter between 4 Fr and 10 Fr and configured to permit insertion of a second interventional medical device therethrough for performing the interventional medical procedure; and a second sidearm comprising a Luer connector having a size between 8 Fr and 14 Fr, the second sidearm angled relative to the longitudinal axis of the second elongated shaft and defining a fourth inlet, a fourth outlet, and a fourth lumen extending between the fourth inlet and the fourth outlet, the fourth lumen fluidically coupled to the third lumen at the proximal region of the second elongated shaft; and

a tubing having a first end configured to be coupled to the port, and a second end configured to be coupled to the Luer connector of the second sidearm, the tubing configured to redirect at least some of the blood flow from the second lumen through the tubing into the fourth lumen of the second sidearm and into the third lumen of the second elongated shaft and out the third outlet for perfusion of the patient's distal extremities.

30. The system of claim 29, wherein the distal perfusion sheath and cannula combination device further comprises:

a first port fluidically coupled to the third lumen at the proximal region of the second elongated shaft, the first port angled towards the third inlet to permit fluid flow therethrough to washout stasis regions of blood within the third lumen; and a second port fluidically coupled to the fourth lumen of the second sidearm.

* * * * *